US009505840B2

(12) United States Patent
Holz et al.

(10) Patent No.: US 9,505,840 B2
(45) Date of Patent: Nov. 29, 2016

(54) INHIBITION OF BONE RESORPTION WITH RANKL BINDING PEPTIDES

(75) Inventors: Josefin-Beate Holz, Munich (DE); Alex Hemeryck, Oostakker (BE)

(73) Assignee: Ablynx N.V., Zwijnaarde (BE)

( * ) Notice: Subject to any disclaimer, the term of this patent is extended or adjusted under 35 U.S.C. 154(b) by 101 days.

(21) Appl. No.: 14/122,307

(22) PCT Filed: May 29, 2012

(86) PCT No.: PCT/EP2012/059968
§ 371 (c)(1),
(2), (4) Date: Feb. 4, 2014

(87) PCT Pub. No.: WO2012/163887
PCT Pub. Date: Dec. 6, 2012

(65) Prior Publication Data
US 2014/0170167 A1    Jun. 19, 2014

Related U.S. Application Data

(60) Provisional application No. 61/491,066, filed on May 27, 2011.

(51) Int. Cl.
*A61K 39/00* (2006.01)
*A61K 39/395* (2006.01)
*C07K 16/28* (2006.01)
*C07K 16/24* (2006.01)

(52) U.S. Cl.
CPC ............ *C07K 16/28* (2013.01); *C07K 16/24* (2013.01); *A61K 2039/505* (2013.01); *A61K 2039/545* (2013.01); *C07K 2317/22* (2013.01); *C07K 2317/31* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 8,623,361 B2 | 1/2014 | Beirnaert et al. |
| 2004/0033535 A1 | 2/2004 | Boyle et al. |
| 2004/0213788 A1 | 10/2004 | Sweet et al. |
| 2010/0104568 A1 | 4/2010 | Beirnaert et al. |
| 2011/0002929 A1 | 1/2011 | Beirnaert et al. |
| 2014/0205601 A1 | 7/2014 | Beirnaert et al. |

FOREIGN PATENT DOCUMENTS

| CN | 101796072 A | 8/2010 |
| JP | 2004-520011 | 7/2004 |
| JP | 2008-540279 | 11/2008 |
| JP | 2009-515903 | 4/2009 |
| WO | WO 02/15846 A2 | 2/2002 |
| WO | WO 2004/041862 A2 | 5/2004 |
| WO | WO 2006/122786 A2 | 11/2006 |
| WO | WO 2006/122787 A1 | 11/2006 |
| WO | WO 2006/122825 A2 | 11/2006 |
| WO | WO 2007/042289 A2 | 4/2007 |
| WO | WO 2007/059136 A2 | 5/2007 |
| WO | WO 2008/142164 A2 | 11/2008 |
| WO | WO 2009/095235 A1 | 8/2009 |
| WO | WO 2010/097385 A1 | 9/2010 |
| WO | WO 2010/125187 A2 | 11/2010 |
| WO | WO 2011/026945 A1 | 3/2011 |

OTHER PUBLICATIONS

Office Action dated Mar. 7, 2013 for U.S. Appl. No. 12/599,892.
[No Author Listed], Press Release Ablynx reports positive phase I data for its anti-RANKL Nanobody—Ghent, Belgium, Sep. 20, 2010.
[Not Author Listed] Press Release Ablynx provides update on its ongoing phase I study for ALX-0141—Ghent, Belgium. Jan. 9, 2011.
Abdallah et al., Increased RANKL/OPG mRNA ratio in iliac bone biopsies from women with hip fractures. Calcif Tissue Int. Feb. 2005;76(2):90-7. Epub Nov. 18, 2004.
Anderson et al., A homologue of the TNF receptor and its ligand enhance T-cell growth and dendritic-cell function. Nature. Nov. 13, 1997;390(6656):175-9.
Baron et al., Denosumab and bisphosphonates: different mechanisms of action and effects. Bone. Apr. 1, 2011;48(4):677-92. doi: 10.1016/j.bone.2010.11.020. Epub Dec. 9, 2010.
Beirnaert, E. et al. "Competitive pharmacological and pharmacodynamic profile of ALX-0141, a format-engineered Nanobody® targeting human RANKL" (poster), American Society for Bone and Mineral Research (ASBMR), 31st Annual Meeting, Denver, Colorado, Sep. 11-15, 2009.
Bekker et al., A single-dose placebo-controlled study of AMG 162, a fully human monoclonal antibody to RANKL, in postmenopausal women. J Bone Miner Res. Jul. 2004;19(7):1059-66. Epub Mar. 1, 2004.
Bekker et al., The effect of a single dose of osteoprotegerin in postmenopausal women. J Bone Miner Res. Feb. 2001;16(2):348-60.
Bezerra et al., RANK, RANKL and osteoprotegerin in arthritic bone loss. Braz J Med Biol Res. Feb. 2005;38(2):161-70. Epub Feb. 15, 2005.
Body et al., A phase I study of AMGN-0007, a recombinant osteoprotegerin construct, in patients with multiple myeloma or breast carcinoma related bone metastases. Cancer. Feb. 1, 2003;97(3 Suppl):887-92.

(Continued)

*Primary Examiner* — Elizabeth C Kemmerer
(74) *Attorney, Agent, or Firm* — Wolf, Greenfield & Sacks, P.C.

(57) ABSTRACT

Methods are provided for inhibiting bone resorption and/or osteoclast activity. More specifically, methods are provided wherein polypeptides against RANK-L are administered to a subject less frequently and/or at lower dose, while still maintaining effective inhibition of bone resorption and/or osteoclast activity in the subject at unexpectedly prolonged periods of time, particularly in view of the doses administered.

8 Claims, 22 Drawing Sheets

(56) References Cited

OTHER PUBLICATIONS

Bridgeman et al., Denosumab for the reduction of bone loss in postmenopausal osteoporosis: a review. Clin Ther. Nov. 2011;33(11):1547-59. doi: 10.1016/j.clinthera.2011.10.008.

Brown et al., Opg, RANKL, and RANK in cancer metastasis: expression and regulation. Cancer Treat Res. 2004;118:149-72.

Byers, What can randomized controlled trials tell us about nutrition and cancer prevention? CA Cancer J Clin. Nov.-Dec. 1999;49(6):353-61.

Campagnuolo et al., Kinetics of bone protection by recombinant osteoprotegerin therapy in Lewis rats with adjuvant arthritis. Arthritis Rheum. Jul. 2002;46(7):1926-36.

Casset et al., A peptide mimetic of an anti-CD4 monoclonal antibody by rational design. Biochem Biophys Res Commun. Jul. 18, 2003;307(1):198-205.

Chen et al., Selection and analysis of an optimized anti-VEGF antibody: crystal structure of an affinity-matured Fab in complex with antigen. J Mol Biol. Nov. 5, 1999;293(4):865-81.

Coppieters et al., Formatted anti-tumor necrosis factor alpha VHH proteins derived from camelids show superior potency and targeting to inflamed joints in a murine model of collagen-induced arthritis. Arthritis Rheum. Jun. 2006;54(6):1856-66.

Crotti et al., Receptor activator NF-kappaB ligand (RANKL) expression in synovial tissue from patients with rheumatoid arthritis, spondyloarthropathy, osteoarthritis, and from normal patients: semiquantitative and quantitative analysis. Ann Rheum Dis. Dec. 2002;61(12):1047-54.

De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.

Desmyter, A. et al., Antigen specificity and high affinity binding provided by one single loop of a camel single-domain antibody. J Biol Chem Jul. 13, 2001;276(28):26285-90. Epub May 7, 2001.

Eghbali-Fatourechi et al., Role of RANK ligand in mediating increased bone resorption in early postmenopausal women. J Clin Invest. Apr. 2003;111(8):1221-30.

Garnero, P. et al., Short-term effects of new synthetic conjugated estrogens on biochemical markers of bone turnover. J Clin Pharmacol. Mar. 2002;42(3):290-6.

Gibbs, Nanobodies. Scientific American. Aug. 2005:79-83.

Granziero et al., Adoptive immunotherapy prevents prostate cancer in a transgenic animal model. Eur J Immunol. Apr. 1999;29(4):1127-38.

Hamers-Casterman et al., Naturally occurring antibodies devoid of light chains. Nature. Jun. 3, 1993;363(6428):446-8.

Harmsen et al., Llama heavy-chain V regions consist of at least four distinct subfamilies revealing novel sequence features. Mol Immunol. Aug. 2000;37(10):579-90.

Holliger et al., Engineered antibody fragments and the rise of single domains. Nat Biotechnol. Sep. 2005;23(9):1126-36.

Holm et al., Functional mapping and single chain construction of the anti-cytokeratin 8 monoclonal antibody TS1. Mol Immunol. Feb. 2007;44(6):1075-84. Epub Sep. 20, 2006.

Holt et al., Domain antibodies: proteins for therapy. Trends Biotechnol. Nov. 2003;21(11):484-90.

Hsu et al., Tumor necrosis factor receptor family member RANK mediates osteoclast differentiation and activation induced by osteoprotegerin ligand. Proc Natl Acad Sci U S A. Mar. 30, 1999;96(7):3540-5.

Jespers et al.,Crystal structure of HEL4, a soluble, refoldable human V(H) single domain with a germ-line scaffold. J Mol Biol. Apr. 2, 2004;337(4):893-903.

Johnell et al., Predictive value of BMD for hip and other fractures. J Bone Miner Res. Jul. 2005;20(7):1185-94. Epub Mar. 7, 2005. Erratum in: J Bone Miner Res. May 2007;22(5):774.

Johnson et al., The Kabat database and a bioinformatics example. Methods Mol Biol. 2004;248:11-25.

Jones et al., Role of RANKL and RANK in bone loss and arthritis. Ann Rheum Dis. Nov. 2002;61 Suppl 2:ii32-9.

Khosla, Minireview: the OPG/RANKL/RANK system. Endocrinology. Dec. 2001;142(12):5050-5.

Kong et al., OPGL is a key regulator of osteoclastogenesis, lymphocyte development and lymph-node organogenesis. Nature. Jan. 28, 1999;397(6717):315-23.

Kostenuik, Osteoprotegerin and RANKL regulate bone resorption, density, geometry and strength. Curr Opin Pharmacol. Dec. 2005;5(6):618-25. Epub Sep. 26, 2005.

Lacey et al., Osteoprotegerin ligand is a cytokine that regulates osteoclast differentiation and activation. Cell. Apr. 17, 1998;93(2):165-76.

Lamminmaki et al., Crystal structure of a recombinant anti estradiol Fab fragment in complex with 17beta-estradiol. J Biol Chem. Sep. 28, 2001;276(39):36687-94. Epub Jul. 12, 2001.

Lewiecki, RANK ligand inhibition with denosumab for the management of osteoporosis. Expert Opin Biol Ther. Oct. 2006;6(10):1041-50.

Lewiecki, Treatment of osteoporosis with denosumab. Maturitas. Jun. 2010;66(2):182-6. doi: 10.1016/j.maturitas.2010.02.008. Epub Mar. 16, 2010.

Li et al., RANK is the intrinsic hematopoietic cell surface receptor that controls osteoclastogenesis and regulation of bone mass and calcium metabolism. Proc Natl Acad Sci U S A. Feb. 15, 2000;97(4):1566-71.

Lubberts et al., Increase in expression of receptor activator of nuclear factor kappaB at sites of bone erosion correlates with progression of inflammation in evolving collagen-induced arthritis. Arthritis Rheum. Nov. 2002;46(11):3055-64.

Lum et al., Evidence for a role of a tumor necrosis factor-alpha (TNF-alpha)—converting enzyme-like protease in shedding of TRANCE, a TNF family member involved in osteoclastogenesis and dendritic cell survival. J Biol Chem. May 7, 1999;274(19):13613-8.

MacCallum et al., Antibody-antigen interactions: contact analysis and binding site topography. J Mol Biol. Oct. 11, 1996;262(5):732-45.

Martin, Protein Sequence and Structure Analysis of Antibody Variable Domains. Antibody Eng. 2010;2:33-51.

McClung et al., Denosumab in postmenopausal women with low bone mineral density. N Engl J Med. Feb. 23, 2006;354(8):821-31.

McClung, Inhibition of RANKL as a treatment for osteoporosis: preclinical and early clinical studies. Curr Osteoporos Rep. Mar. 2006;4(1):28-33.

Miller, Denosumab: anti-RANKL antibody. Curr Osteoporos Rep. Mar. 2009;7(1):18-22.

Muyldermans et al., Unique single-domain antigen binding fragments derived from naturally occurring camel heavy-chain antibodies. J Mol Recognit. Mar.-Apr. 1999;12(2):131-40.

Muyldermans, Single domain camel antibodies: current status. Reviews Molecular Biotechnology. Jun. 2001;74(4):277-302.

Nagai et al., Cancer cells responsible for humoral hypercalcemia express mRNA encoding a secreted form of ODF/TRANCE that induces osteoclast formation. Biochem Biophys Res Commun. Mar. 16, 2000;269(2):532-6.

Niida et al , Gamma-glutamyltranspeptidase stimulates receptor activator of nuclear factor-kappaB ligand expression independent of its enzymatic activity and serves as a pathological bone-resorbing factor. J Biol Chem. Feb. 13, 2004;279(7):5752-6. Epub Nov. 21, 2003.

Ohno et al., Antigen-binding specificities of antibodies are primarily determined by seven residues of VH. Proc Natl Acad Sci U S A. May 1985;82(9):2945-9.

Okada et al., Bone marrow metastatic myeloma cells promote osteoclastogenesis through RANKL on endothelial cells. Clin Exp Metastasis. 2003;20(7):639-46.

Padlan et al., Structure of an antibody-antigen complex: crystal structure of the HyHEL-10 Fab-lysozyme complex. Proc Natl Acad Sci U S A. Aug. 1989;86(15):5938-42.

Panka et al., Variable region framework differences result in decreased or increased affinity of variant anti-digoxin antibodies. Proc Natl Acad Sci U S A. May 1988;85(9):3080-4.

(56) References Cited

OTHER PUBLICATIONS

Paul, Fundamental Immunology. Third Edition. 1993;242.
Peterson, A PK/PD Model developed in cynomolgus monkeys predicts concentrations and effects of AMG 162, a fully human monoclonal antibody against RANKL, in healthy postmenopausal women. Annual meeting Baltimore. Nov. 2004.
Queen et al., A humanized antibody that binds to the interleukin 2 receptor. Proc Natl Acad Sci U S A. Dec. 1989;86(24):10029-33.
Reddy, Etiology of Paget's disease and osteoclast abnormalities. J Cell Biochem. Nov. 1, 2004;93(4):688-96.
Riechmann et al., Single domain antibodies: comparison of camel VH and camelised human VH domains. J Immunol Methods. Dec. 10, 1999;231(1-2):25-38.
Roitt et al., Molecules which recognize antigen. Immunology. 1989; 2nd ed:5.1-5.11.
Van De Wetering De Rooij et al., Safety, pharmacokinetics and efficacy of anti-RANKL Nanobody ALX-0141 in healthy postmenopausal women. Abstract EULAR conference: May 25-28, 2011.
Roovers et al., Efficient inhibition of EGFR signaling and of tumour growth by antagonistic anti-EGFR Nanobodies. Cancer Immunol Immunother. Mar. 2007;56(3):303-317.
Rudikoff et al., Single amino acid substitution altering antigen-binding specificity. Proc Natl Acad Sci U S A. Mar. 1982;79(6):1979-83.
Silence et al., ALX-0081 Nanobody™, an Engineered Bivalent Anti-Thrombotic Drug Candidate with Improved Efficacy and Safety as Compared to the Marketed Drugs. Blood. ASH Annual Meeting Abstracts. Nov. 16, 2006 16;108(11):269A. Abstract #896.
Simonet et al., Osteoprotegerin: a novel secreted protein involved in the regulation of bone density. Cell. Apr. 18, 1997;89(2):309-19.
Singer et al., Genes and Genomes. 1998;1: 131-7, 256-7.
Singer, M. S. et al., "NTx: A New Tool to Track and Treat Osteoporosis," Orthopedics Technology Spotlight; *Medcompare*™http://www.medcompare.com/spotlight.asp?spotlightid=181 Accessed on Jun. 28, 2011, 2 pages.
Stilgren et al., Skeletal changes in osteoprotegerin and receptor activator of nuclear factor-kappab ligand mRNA levels in primary hyperparathyroidism: effect of parathyroidectomy and association with bone metabolism. Bone. Jul. 2004;35(1):256-65.
Sugimoto, [Anti-RANKL monoclonal antibody Denosumab (AMG162)]. Clin Calcium. Jan. 2011;21(1):46-51. doi: CliCa11014651. Abstract only.
Sugimoto, [Osteoporosis treatment by anti-RANKL antibody]. Clin Calcium. Aug. 2011;21(8):1209-15. doi: CliCa110812091215. Abstract only.
Tsangari et al., Increased expression of IL-6 and RANK mRNA in human trabecular bone from fragility fracture of the femoral neck. Bone. Jul. 2004;35(1):334-42.
Vajdos et al., Comprehensive functional maps of the antigen-binding site of an anti-ErbB2 antibody obtained with shotgun scanning mutagenesis. J Mol Biol. Jul. 5, 2001;320(2):415-28.
Vu et al., Comparison of llama VH sequences from conventional and heavy chain antibodies. Mol Immunol. Nov.-Dec. 1997;34(16-17):1121-31.
Ward et al., Binding activities of a repertoire of single immunoglobulin variable domains secreted from *Escherichia coli*. Nature. Oct. 12, 1989;341(6242):544-6.
Wesolowski et al., Single domain antibodies: promising experimental and therapeutic tools in infection and immunity. Med Microbiol Immunol. Aug. 2009;198(3):157-74. doi: 10.1007/s00430-009-0116-7. Epub Jun. 16, 2009.
Wolfson, Ablynx makes nanobodies from llama bodies. Chem Biol. Dec. 2006;13(12):1243-4.
Wong et al., TRANCE is a novel ligand of the tumor necrosis factor receptor family that activates c-Jun N-terminal kinase in T cells. J Biol Chem. Oct. 3, 1997;272(40):25190-4.
Wu et al., Humanization of a murine monoclonal antibody by simultaneous optimization of framework and CDR residues. J Mol Biol. Nov. 19, 1999;294(1):151-62.
Yasuda et al., Osteoclast differentiation factor is a ligand for osteoprotegerin/osteoclastogenesis-inhibitory factor and is identical to TRANCE/RANKL. Proc Natl Acad Sci U S A. Mar. 31, 1998;95(7):3597-602.
Huang et al., Transforming growth factor beta peptide antagonists and their conversion to partial agonists. J Biol Chem. Oct. 24, 1997;272(43):27155-9.
LeFranc et al. IMGT unique numbering for immunoglobulin and T cell receptor variable domains and Ig superfamily V-like domains. Dev Comp Immunol. Jan. 2003;27(1):55-77.
Paul, Fv structure and diversity in three dimensions. Fundamental Immunology, 3rd Edition, 1993:292-295.
Tamura et al., Structural correlates of an anticarcinoma antibody: identification of specificity-determining residues (SDRs) and development of a minimally immunogenic antibody variant by retention of SDRs only. J Immunol. Feb. 1, 2000;164(3):1432-41.
Fillipovich et al., Biochemical principles of human life activities. VLADOS. 2005;49-50.

(a)

(b)

(a)

(b)

(d)

(e)

(f)

(a)

(c)

(d)

(e)

(f)

INHIBITION OF BONE RESORPTION WITH RANKL BINDING PEPTIDES

RELATED APPLICATIONS

This application is a national stage filing under 35 U.S.C. §371 of international application PCT/EP2012/059968, filed May 29, 2012, which was published under PCT Article 21(2) in English, and claims the benefit under 35 U.S.C. §119(e) of U.S. provisional application Ser. No. 61/491,066, filed May 27, 2011, the disclosures of which are incorporated by reference herein in their entireties.

FIELD OF THE INVENTION

The present invention relates to methods for inhibiting bone resorption and/or osteoclast activity for prolonged periods of time using amino acid sequences that are directed against Receptor Activator of Nuclear factor Kappa B Ligand (RANK-L). More specifically, the present invention provides polypeptides directed against RANK-L at specific dose ranges for inhibiting RANK-L mediated bone resorption or osteoclast activity.

BACKGROUND OF THE INVENTION

Remodelling (turnover) of bone is the process by which the adult skeleton is continually being resorbed (removed) and formed (replaced). Bone remodeling involves the synthesis of bone matrix by osteoblasts and its resorption by osteoclast cells. Osteoclasts, derived from hematopoietic cells, are unique forms of tissue macrophages that have the capacity to resorb bone tissue. Osteoblasts are specialized fibroblasts that have the capacity of secreting bone collagen. There is an exquisite coordination among the activities of these bone cells that link the processes of bone formation and bone resorption.

Bone remodelling is controlled by a balance between RANK-L/RANK and the RANK-L decoy receptor OPG. RANK-L and its receptor RANK are essential for the development and activation of osteoclasts. OPG, a secreted protein, is an effective inhibitor of osteoclast maturation and osteoclasts activation. In normal bone homeostasis, RANK-L and OPG participate in a cytokine axis that tightly controls the generation of osteoclasts from monocyte precursors. RANK-L, expressed by osteoblasts and bone marrow stromal cells, binds to its functional receptor, RANK, to stimulate differentiation of osteoclasts from precursor cells and the proliferation and activity of mature osteoclasts. OPG, which is expressed by osteoblasts, stromal cells, dendritic cells, and megakaryocytes, limits this process by acting as a soluble decoy receptor for RANK-L.

The TNF family molecule RANK-L is encoded by a single gene (rankl) at human chromosome 13q14. RANK-L mRNA is expressed at highest levels in bone and bone marrow, as well as in lymphoid tissues (lymph node, thymus, spleen, fetal liver, and Peyer's patches) (Anderson et al. 1997, Nature 390: 175-179; Wong et al. 1997, J. Biol. Chem. 272: 25190-25194; Lacey et al. 1998, Cell 93: 165-176; Yasuda et al. 1998, Proc. Natl. Acad. Sci. USA 95: 3597-3602). Alternative splicing of RANK-L mRNA allows expression as a type II transmembrane glycoprotein of either 316 or 270 amino acids or as a soluble ligand of 243 amino acids (Kong et al. 1999, Nature 397: 315-323; Nagai et al. 2000, Biochem Biophys. Res. Commun. 269: 532-536). In addition, RANK-L can be released from its membrane bound state by metalloproteinases, including TNF-alpha convertase (Lum et al. 1999, J. Biol. Chem. 274: 13613-13618). All four isoforms of RANK-L associate into trimeric molecules capable of triggering osteoclastogenesis.

RANK (receptor activator of NFkappaB; also known as TRANCE-R, ODAR, or TNFRSF11A), expressed on preosteoclastic cells, is the sole receptor on these cells for RANK-L (Li et al. 2000, Proc. Natl. Acad. Sci. USA 97: 1566-1571). RANK activation by RANK-L is followed by its interaction with TNF receptor-associated (TRAF) family members, activation of nuclear factor (NF)-kappaB and c-Fos, JNK, c-src, and the serine/threonine kinase Akt/PKB (Anderson et al. 1997, Nature 390: 175-179; Hsu et al. 1999, Proc. Acad. Sci. USA 96: 3540-3545).

OPG (osteoprotegerin; "protector of the bone"; also known as osteoclastogenesis inhibitory factor (OCIF)) is a soluble, 110-kDa, disulfide-linked, homodimeric glycoprotein produced and released by activated osteoblast cells (Simonet et al. 1997, Cell 89: 309-319) with homology to the TNF receptor family, that functions as a decoy receptor for RANK-L and competes with RANK for RANK-L binding. Consequently, OPG is an effective inhibitor of osteoclast maturation and osteoclast activation (Simonet et al. 1997, Cell 89: 309-319; Lacey et al. 1998, Cell 93: 165-176; Kong et al. 1999, Nature 397: 315-323), thereby reducing bone resorption.

A more detailed overview of the OPG/RANK-L/RANK system as the mediator of bone formation and destruction is presented in Khosla, (2001 Endocrinology 142: 5050-5055), Holstead Jones et al. (2002, Ann. Rheum. Dis. 61 (Suppl II): ii32-ii39), Bezerra et al. (2005, Brazilian J. Med. Biol. Res. 38: 161-170) and McClung (2006, Current Osteoporosis Reports 4: 28-33).

Several bone disorders occur when there is an imbalance between the resorption and formation components of bone remodeling activity (uncoupling of bone homeostasis). Imbalances between osteoclast and osteoblast activities can arise from a wide variety of hormonal changes or perturbations of inflammatory and growth factors, such as e.g. an altered balance between OPG and RANK-L. When bone resorption is greater than bone formation, there is a net loss of bone over time. This can eventually result in low bone mass (osteopenia) or osteoporosis. When bone formation exceeds resorption, there is a net increase in bone mass (osteopetrosis).

Excessive bone loss or destruction due to higher RANK-L, lower OPG or both has been implicated in many disease states, including post-menopausal osteoporosis (Eghbali-Fatourechi et al. 2003, Journal of Clinical Investigation 111: 1221-1230; Tsangari et al. 2004, Bone 35: 334-342; Abdallah et al. 2005, Calcified Tissue International 76: 90-97).

Pharmacological agents to decrease risk of fracture have been available for more than ten years. Anticatabolic drugs (oestrogens, bisphosphonates, calcitonin and selective oestrogen receptor modulators) decrease bone resorption, while anabolic agents, such as recombinant human parathyroid hormone (PTH), increase bone formation and bone size. The bisphosphonate class of drugs is the one most often used for the treatment of osteoporosis. Although this drug class is generally very safe, oral dosing is complex and has been associated with gastrointestinal adverse events in a small percentage of clinical practice patients. Clinical trials are evaluating increasing intervals of intravenous bisphosphonate dosing.

The recent discovery of the OPG/RANK-L/RANK system as pivotal regulatory factors in the pathogenesis of bone diseases and disorders like osteoporosis provides unique targets for therapeutic agents. In laboratory animals and in humans, administering forms of OPG markedly inhibited osteoclast activity and improved bone strength (Bekker et al. 2001, J. Bone Miner. Res. 16: 348-360; Campagnuolo et al. 2002, Arthritis Rheum. 46: 1926-1936; Bezerra et al. 2005, Brazilian J. Med. Biol. Res. 38: 161-170; McClung 2006, Current Osteoporosis Reports 4: 28-33). In early studies in humans, a fully human antibody against RANK-L (Denosumab) reduced bone turnover and improved bone density (Body et al. 2003, Cancer 97: 887-892; Bekker et al. 2004, J. Bone Miner. Res. 19: 1059-1066; McClung 2006, Current Osteoporosis Reports 4: 28-33; Lewiecki 2006, Expert Opin. Biol. Ther. 6: 1041-1050; McClung et al. 2006, N. Engl. J. Med. 354: 821-831). Such complete antibodies, however, face the drawbacks of full size antibodies such as high production costs, low stability, and their large size, which e.g. impedes their access to certain hidden epitopes.

SUMMARY OF THE INVENTION

The Applicant has discovered that the administration to human subjects of polypeptides as described herein that specifically bind RANKL (also referred to herein as "polypeptide(s) of the invention") provides an unexpectly sustained, prolonged effect on bone resorption and/or osteoclast activity in the human subjects as observed through changes in relevant biomarkers (such as CTX-1, NTX-1 TRACP5b, PINP, and/or BAP). For example, the change in one or more markers of bone metabolism and/or bone homeostasis can be measured for at least 30 days after administration. The change in the one or more markers of bone metabolism and/or bone homeostasis can persist for longer periods of time, such as at least 60 days, at least 90 days, at least 120 days, at least 150 days, at least 180 days, at least 210 days, at least 240 days, at least 270 days, at least 300 days, at least 330 days, or at least 360 days. This effect is also achieved rapidly, with the reductions in biomarkers observed, in some embodiments by 8 hours after administration of the polypeptide that specifically binds RANKL.

The unexpected sustained, prolonged effect on RANK-L mediated bone resorption and osteoclast activity was mainly caused by the much better potency ($IC_{50}$) of the polypeptide of the invention in vivo than what was predicted based on background art and preclinical information. Because of this better potency of the polypeptide of the invention, an unexpectedly sustained, prolonged effect on RANK-L mediated bone resorption and osteoclast activity in the human subjects was observed compared to what was assessed based on pre-clinical modelling. As a consequence, less therapeutic molecules (i.e. lower dose) need to be administered, or less frequent dosing of the therapeutic molecule need to be applied in order to obtain the same effect on RANK-L mediated bone resorption and osteoclast activity (observed through changes in relevant biomarkers such as CTX-1, NTX-1, TRACP5b, PINP, and/or BAP).

Therefore, the invention relates to the use of the polypeptides described herein to inhibit bone resorption and/or osteoclast activity in a subject for unexpectedly prolonged periods of time, particularly in view of the doses administered. The invention also provides for less frequent and/or lower dose administration to a subject of the polypeptides described herein, while still maintaining effective inhibition of bone resorption and/or osteoclast activity in the subject at unexpectedly prolonged periods of time, particularly in view of the doses administered. In particular, the invention provides pharmacologically active agents, compositions, methods and/or dosing schedules that have certain advantages compared to the agents, compositions, methods and/or dosing schedules that are currently used and/or known in the art, including the ability to dozes less frequently or to administer lower doses to obtain equivalent effects in inhibiting RANK-L mediated bone resorption and/or osteoclast activity.

According to one aspect of the invention, methods for inhibiting bone resorption or osteoclast activity in a subject are provided. The methods include administering to the subject a polypeptide that specifically binds Receptor Activator of Nuclear Factor kappa B Ligand (RANK-L) (also referred to as "polypeptide of the invention"). The amount of the polypeptide administered is effective to change one or more markers of bone metabolism and/or bone homeostasis for at least 30 days after administration. In some embodiments, the polypeptide is administered in an amount from about 0.01 mg/kg to about 10 mg/kg. In some embodiments, the markers of bone metabolism are selected from crosslinking telopeptide of type I collagen (CTX-1), N-terminal telopeptide of type I collagen (NTX-1), tartrate-resistant acid phosphatase isoform 5b (TRACP5b), N-terminal propeptide of type I procollagen (P1NP) and bone-specific alkaline phosphatase (BAP). In some embodiments, one or more of the CTX-1, NTX-1, TRACP5b, P1NP and BAP is/are measured using an ELISA assay specific for CTX-1, NTX-1, or TRACP5b; a radioimmunoassay specific for P1NP, or an immunoenzymetric assay specific for BAP, respectively.

According to another aspect of the invention, methods for inhibiting bone resorption or osteoclast activity in a subject are provided. The methods include administering to the subject a polypeptide that specifically binds Receptor Activator of Nuclear Factor kappa B Ligand (RANKL) (polypeptide of the invention). The amount of the polypeptide administered is effective to reduce serum level of crosslinking telopeptide of type I collagen (CTX-1) by at least 30%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least about 30 days after administration. In some embodiments, the polypeptide is administered in an amount of at least 0.003 mg/kg. In some embodiments, the polypeptide is administered in an amount from about 0.003 mg/kg to about 0.03 mg/kg. In other embodiments, the CTX-1 is reduced by at least 30%, compared to pre-treatment or normal levels, for about 30 days after administration, and the polypeptide is administered in an amount of less than or equal to 0.003 mg/kg.

In some embodiments, the CTX-1 is reduced by at least 30%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 60 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the CTX-1 is reduced by at least 30%, compared to pre-treatment or normal levels, for about 30 days after administration, and the polypeptide is administered in an amount of less than or equal to 0.01 mg/kg.

In some embodiments, the CTX-1 is reduced by at least 30%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 90 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the CTX-1 is reduced by at least 30%, compared to pre-treatment or normal levels, for about 90 days after administration, and the polypeptide is administered in an amount of less than or equal to 0.01 mg/kg.

In some embodiments, the CTX-1 is reduced by at least 30%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 120 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the CTX-1 is reduced by at least 30%, compared to pre-treatment or normal levels, for about 120 days after administration, and the polypeptide is administered in an amount of less than or equal to 0.01 mg/kg.

In some embodiments, the CTX-1 is reduced by at least 30%, compared to pre-treatment or normal levels, for at least 150 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 150 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the CTX-1 is reduced by at least 30%, compared to pre-treatment or normal levels, for about 150 days after administration, and the polypeptide is administered in an amount of less than or equal to 0.1 mg/kg.

In some embodiments, the CTX-1 is reduced by at least 30%, compared to pre-treatment or normal levels, for at least 180 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 180 days after administration. In some embodiments, the polypeptide is administered in an amount of at least 0.1 mg/kg. In some embodiments, the polypeptide is administered in an amount of at least 1 mg/kg. In certain embodiments, the polypeptide is administered in an amount from about 0.1 mg/kg to about 10 mg/kg. In certain embodiments, the polypeptide is administered in an amount from about 0.1 mg/kg to about 1 mg/kg. In other embodiments, the CTX-1 is reduced by at least 30%, compared to pre-treatment or normal levels, for about 180 days after administration, and the polypeptide is administered in an amount of less than or equal to 0.1 mg/kg. In other embodiments, the CTX-1 is reduced by at least 30%, compared to pre-treatment or normal levels, for about 180 days after administration, and the polypeptide is administered in an amount of less than or equal to 1 mg/kg.

In some embodiments, the CTX-1 is reduced by at least 30%, compared to pre-treatment or normal levels, for at least 210 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 210 days after administration. In some embodiments, the polypeptide is administered in an amount of at least 0.1 mg/kg. In some embodiments, the polypeptide is administered in an amount of at least 1 mg/kg. In certain embodiments, the polypeptide is administered in an amount from about 0.1 mg/kg to about 10 mg/kg. In certain embodiments, the polypeptide is administered in an amount from about 0.1 mg/kg to about 1 mg/kg. In other embodiments, the CTX-1 is reduced by at least 30%, compared to pre-treatment or normal levels, for about 210 days after administration, and the polypeptide is administered in an amount of less than or equal to 0.1 mg/kg. In other embodiments, the CTX-1 is reduced by at least 30%, compared to pre-treatment or normal levels, for about 210 days after administration, and the polypeptide is administered in an amount of less than or equal to 1 mg/kg.

In some embodiments, the CTX-1 is reduced by at least 30%, compared to pre-treatment or normal levels, for at least 270 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 30%, compared to pre-treatment or normal levels, and to maintain serum levels of CTX-1 at at least 30% for at least 270 days after administration. In some embodiments, the polypeptide is administered in an amount of at least 0.1 mg/kg. In some embodiments, the polypeptide is administered in an amount of at least 1 mg/kg. In certain embodiments, the polypeptide is administered in an amount from about 0.1 mg/kg to about 10 mg/kg. In certain embodiments, the polypeptide is administered in an amount from about 0.1 mg/kg to about 1 mg/kg. In other embodiments, the CTX-1 is reduced by at least 30%, compared to pre-treatment or normal levels, for about 270 days after administration, and the polypeptide is administered in an amount of less than or equal to 0.1 mg/kg. In other embodiments, the CTX-1 is reduced by at least 30%, compared to pre-treatment or normal levels, for about 270 days after administration, and the polypeptide is administered in an amount of less than or equal to 1 mg/kg.

According to another aspect of the invention, the amount of the polypeptide administered is effective to reduce serum level of cross-linking telopeptide of type I collagen (CTX-1) by at least 45%, compared to pre-treatment or normal levels, for at least about 30 days after administration. The invention thus also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least about 30 days after administration. In some embodiments, the polypeptide is administered in an amount of at least 0.01 mg/kg. In some embodiments, the polypeptide is administered in an amount from about 0.01 mg/kg to about 0.1 mg/kg. In some embodiments, the polypeptide is administered in an amount from about 0.01 mg/kg to about 3 mg/kg. In other embodiments, the CTX-1 is reduced by at least 45%, compared to pre-treatment or normal levels, for about 30 days after administration, and the polypeptide is administered in an amount of less than or equal to 0.01 mg/kg.

According to another aspect of the invention, the amount of the polypeptide administered is effective to reduce serum level of cross-linking telopeptide of type I collagen (CTX-1) by at least 45%, compared to pre-treatment or normal levels, for at least about 60 days after administration. The invention thus also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least about 60 days after administration. In some embodiments, the polypeptide is administered in an amount of at least 0.01 mg/kg. In some embodiments, the polypeptide is administered in an amount from about 0.01 mg/kg to about 0.1 mg/kg. In other embodiments, the CTX-1 is reduced by at least 45%, compared to pre-treatment or normal levels, for about 60 days after administration, and the polypeptide is administered in an amount of less than or equal to 0.01 mg/kg.

According to another aspect of the invention, the amount of the polypeptide administered is effective to reduce serum level of cross-linking telopeptide of type I collagen (CTX-1) by at least 45%, compared to pre-treatment or normal levels, for at least about 90 days after administration. The invention thus also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least about 90 days after administration. In some embodiments, the polypeptide is administered in an amount of at least 0.03 mg/kg. In some embodiments, the polypeptide is administered in an amount from about 0.03 mg/kg to about 0.3 mg/kg. In other embodiments, the CTX-1 is reduced by at least 45%, compared to pre-treatment or normal levels, for about 90 days after administration, and the polypeptide is administered in an amount of less than or equal to 0.03 mg/kg.

In some embodiments, the CTX-1 is reduced by at least 45%, compared to pre-treatment or normal levels, for about 30 days to 3 months after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least about 30 days to 3 months after administration. In certain embodiments, the polypeptide is administered in an amount from about 0.01 mg/kg to about 0.3 mg/kg. In some embodiments, the polypeptide is administered in an amount from about 0.03 mg/kg to about 0.3 mg/kg. In some embodiments, the CTX-1 is reduced by at least 45%, compared to pre-treatment or normal levels, for about 30 days after administration, and the polypeptide is administered in an amount from about 0.03 mg/kg to about 0.3 mg/kg. In other embodiments, the CTX-1 is reduced by at least 45%, compared to pre-treatment or normal levels, for about 30 days after administration, and the polypeptide is administered in an amount of less than or equal to 0.03 mg/kg.

According to another aspect of the invention, the amount of the polypeptide administered is effective to reduce serum level of cross-linking telopeptide of type I collagen (CTX-1) by at least 45%, compared to pre-treatment or normal levels, for at least about 120 days after administration. The invention thus also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least about 120 days after administration. In some embodiments, the polypeptide is administered in an amount of at least 0.1 mg/kg. In some embodiments, the polypeptide is administered in an amount from about 0.1 mg/kg to about 1 mg/kg. In other embodiments, the CTX-1 is reduced by at least 45%, compared to pre-treatment or normal levels, for about 120 days after administration, and the polypeptide is administered in an amount of less than or equal to 0.1 mg/kg.

In some embodiments, the CTX-1 is reduced by at least 45%, compared to pre-treatment or normal levels, for at least 150 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least 150 days after administration. In some embodiments, the polypeptide is administered in an amount of at least 1 mg/kg. In certain embodiments, the polypeptide is administered in an amount from about 1 mg/kg to about 10 mg/kg. In other embodiments, the CTX-1 is reduced by at least 45%, compared to pre-treatment or normal levels, for about 150 days after administration, and the polypeptide is administered in an amount of less than or equal to 1 mg/kg.

In some embodiments, the CTX-1 is reduced by at least 45%, compared to pre-treatment or normal levels, for at least 180 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at at least 45% for at least 180 days after administration. In some embodiments, the polypeptide is administered in an amount of at least 1 mg/kg. In certain embodiments, the polypeptide is administered in an amount from about 1 mg/kg to about 10 mg/kg. In other embodiments, the CTX-1 is reduced by at least 45%, compared to pre-treatment or normal levels, for about 180 days after administration, and the polypeptide is administered in an amount of less than or equal to 1 mg/kg.

In some embodiments, the CTX-1 is reduced by at least 45%, compared to pre-treatment or normal levels, for about 3 months to 6 months after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at least 45% for about 3 months to 6 months after administration. In some embodiments, the polypeptide is administered in an amount from about 0.3 mg/kg to about 1 mg/kg. In some embodiments, the CTX-1 is reduced by at least 45%, compared to pre-treatment or normal levels for about 3 months after administration, and the polypeptide is administered in an amount from about 0.3 mg/kg to about 1 mg/kg. In other embodiments, the CTX-1 is reduced by at least 45%, compared to pre-treatment or normal levels, for about 3 months after administration, and the polypeptide is administered in an amount of less than or equal to 0.3 mg/kg.

In some embodiments, the CTX-1 is reduced by at least 45%, compared to pre-treatment or normal levels, for at least 6 months to 1 year after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 45%, compared to pre-treatment or normal levels, and to maintain serum levels of CTX-1 at least 45% for about 6 months to 1 year after administration. In some embodiments, the polypeptide is administered in an amount from about 1 mg/kg to about 10 mg/kg. In some embodiments, the polypeptide is administered in an amount from about 1 mg/kg to about 3 mg/kg. In some embodiments, the CTX-1 is reduced by at least 45%, compared to pre-treatment or normal levels, for about 6 months after administration, and the polypeptide is administered in an amount from about 1 mg/kg to about 3 mg/kg. In other embodiments, the CTX-1 is reduced by at least 45%, compared to pre-treatment or normal levels, for about 6 months after administration, and the polypeptide is administered in an amount of less than or equal to 1 mg/kg.

In some embodiments, CTX-1 is reduced by at least 50%, compared to pre-treatment or normal levels, for at least 30 days after administration, such as for at least 60 days after administration, for at least 90 days after administration, for at least 120 days after administration, for at least 150 days after administration, for at least 180 days after administration, for times intermediate to these, or longer as described elsewhere herein and as shown in the examples and figures presented herein. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 50%, compared to pre-treatment or normal levels, and to maintain serum levels of CTX-1 at at least 50% for at least 60 days after administration, for at least 90 days after administration, for at least 120 days after administration, for at least 150 days after administration, for at least 180 days after administration, for times intermediate to these, or longer as described elsewhere herein and as shown in the examples and figures presented herein.

In some embodiments, CTX-1 is reduced by at least 60%, compared to pre-treatment or normal levels, for at least 30 days after administration, such as for at least 60 days after administration, for at least 90 days after administration, for at least 120 days after administration, for at least 150 days after administration, for times intermediate to these, or longer as described elsewhere herein and as shown in the examples and figures presented herein. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 60%, compared to pre-treatment or normal levels, and to maintain serum levels of CTX-1 at at least 60% for at least 60 days after administration, for at least 90 days after administration, for at least 120 days after administration, for at least 150 days after administration, for times intermediate to these, or longer as described elsewhere herein and as shown in the examples and figures presented herein.

In some embodiments, CTX-1 is reduced by at least 70%, compared to pre-treatment or normal levels, for at least 30 days after administration, such as for at least 60 days after administration, for at least 90 days after administration, for at least 120 days after administration, for times intermediate to these, or longer as described elsewhere herein and as shown in the examples and figures presented herein. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 70%, compared to pre-treatment or normal levels, and to maintain serum levels of CTX-1 at at least 70% for at least 60 days after administration, for at least 90 days after administration, for at least 120 days after administration, for times intermediate to these, or longer as described elsewhere herein and as shown in the examples and figures presented herein.

According to another aspect of the invention, the amount of the polypeptide administered is effective to reduce serum level of cross-linking telopeptide of type I collagen (CTX-1) by at least 70%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of CTX-1 by at least 70%, compared to pre-treatment or normal levels, and to maintain serum levels of CTX-1 at at least 70% for at least about 30 days after administration. In some embodiments, the polypeptide is administered in an amount of at least 0.03 mg/kg. In some embodiments, the polypeptide is administered in an amount from about 0.03 mg/kg to about 0.3 mg/kg. In other embodiments, the CTX-1 is reduced by at least 70%, compared to pre-treatment or normal levels, for about 30 days after administration, and the polypeptide is administered in an amount of less than or equal to 0.03 mg/kg.

In some embodiments, the CTX-1 is reduced by at least 70%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 70%, compared to pre-treatment or normal levels, and to maintain serum levels of CTX-1 at at least 70% for at least 60 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the CTX-1 is reduced by at least 70%, compared to pre-treatment or normal levels, for about 30 days after administration, and the polypeptide is administered in an amount of less than or equal to 0.1 mg/kg.

In some embodiments, the CTX-1 is reduced by at least 70%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 70%, compared to pre-treatment or normal levels, and to maintain serum levels of CTX-1 at at least 70% for at least 90 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the CTX-1 is reduced by at least 70%, compared to pre-treatment or normal levels, for about 90 days after administration, and the polypeptide is administered in an amount of less than or equal to 0.1 mg/kg.

In some embodiments, the CTX-1 is reduced by at least 70%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 70%, compared to pre-treatment or normal levels, and to maintain serum levels of CTX-1 at at least 70% for at least 120 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the CTX-1 is reduced by at least 70%, compared to pre-treatment or normal levels, for about 120 days after administration, and the polypeptide is administered in an amount of less than or equal to 0.1 mg/kg.

In some embodiments, CTX-1 is reduced by at least 80%, compared to pre-treatment or normal levels, for at least 30 days after administration, such as for at least 60 days after administration, for at least 90 days after administration, for times intermediate to these, or longer as described elsewhere herein and as shown in the examples and figures presented herein. Accordingly, the invention also relates to a polypeptide of the invention for inhibiting RANK-L mediated bone resorption and/or osteoclast activity, wherein the amount of the polypeptide administered is effective to reduce serum levels of CTX-1 by at least 80%, compared to pre-treatment or normal levels, and to maintain serum levels of CTX-1 at at least 80% for at least 60 days after administration, for at least 90 days after administration, for times intermediate to these, or longer as described elsewhere herein and as shown in the examples and figures presented herein. In some embodiments, the polypeptide is administered in an amount of at least 0.1 mg/kg. In certain embodiments, the polypeptide is administered in an amount from about 0.1 mg/kg to about 1 mg/kg. In other embodiments, the CTX-1 is reduced by at least 80%, compared to pre-treatment or normal levels, for about 90 days after administration, and the polypeptide is administered in an amount of less than or equal to 0.1 mg/kg. In other embodiments, the CTX-1 is reduced by at least 80%, compared to pre-treatment or normal levels, for about 90 days after administration, and the polypeptide is administered in an amount of less than or equal to 0.3 mg/kg.

According to another aspect of the invention, the amount of the polypeptide administered is effective to reduce serum level of cross-linking telopeptide of type I collagen (CTX-1) by at least 30%, compared to pre-treatment or normal levels, for about 60 days after administration, and wherein the amount of the polypeptide administered is less than or equal to about 0.003 mg/kg every month. The invention thus also provides a polypeptide of the invention for inhibiting RANK-L mediated bone resorption and/or osteoclast activity, wherein the polypeptide is administered in an amount less than or equal to about 0.003 mg/kg every month and wherein serum levels of CTX-1 are reduced by at least 30%, compared to pre-treatment or normal levels, and maintained at at least 30% for about 60 days after administration.

According to another aspect of the invention, the amount of the polypeptide administered is effective to reduce serum level of cross-linking telopeptide of type I collagen (CTX-1) by at least 30%, compared to pre-treatment or normal levels, for about 150 days after administration, and wherein the amount of the polypeptide administered is less than or equal to about 0.01 mg/kg every month. The invention thus also provides a polypeptide of the invention for inhibiting RANK-L mediated bone resorption and/or osteoclast activity, wherein the polypeptide is administered in an amount less than or equal to about 0.01 mg/kg every month and wherein serum levels of CTX-1 are reduced by at least 30%, compared to pre-treatment or normal levels, and maintained at at least 30% for about 150 days after administration.

According to another aspect of the invention, the amount of the polypeptide administered is effective to reduce serum level of cross-linking telopeptide of type I collagen (CTX-1) by at least 30%, compared to pre-treatment or normal levels, for about 90 days after administration, and wherein the amount of the polypeptide administered is less than or equal to about 0.03 mg/kg every month. The invention thus also provides a polypeptide of the invention for inhibiting RANK-L mediated bone resorption and/or osteoclast activity, wherein the polypeptide is administered in an amount less than or equal to about 0.03 mg/kg every month and wherein serum levels of CTX-1 are reduced by at least 30%, compared to pre-treatment or normal levels, and maintained at at least 30% for about 90 days after administration.

According to another aspect of the invention, the amount of the polypeptide administered is effective to reduce serum level of cross-linking telopeptide of type I collagen (CTX-1) by at least 30%, compared to pre-treatment or normal levels, for about 210 days after administration, and wherein the amount of the polypeptide administered is less than or equal to about 0.1 mg/kg every month. The invention thus also provides a polypeptide of the invention for inhibiting RANK-L mediated bone resorption and/or osteoclast activity, wherein the polypeptide is administered in an amount less than or equal to about 0.1 mg/kg every month and wherein serum levels of CTX-1 are reduced by at least 30%, compared to pre-treatment or normal levels, and maintained at at least 30% for about 210 days after administration.

According to another aspect of the invention, the amount of the polypeptide administered is effective to reduce serum level of cross-linking telopeptide of type I collagen (CTX-1) by at least 30%, compared to pre-treatment or normal levels, for about 210 days after administration, and wherein the amount of the polypeptide administered is less than or equal to about 0.3 mg/kg every month. The invention thus also provides a polypeptide of the invention for inhibiting RANK-L mediated bone resorption and/or osteoclast activity, wherein the polypeptide is administered in an amount less than or equal to about 0.3 mg/kg every month and wherein serum levels of CTX-1 are reduced by at least 30%, compared to pre-treatment or normal levels, and maintained at at least 30% for about 210 days after administration.

According to another aspect of the invention, the amount of the polypeptide administered is effective to reduce serum level of cross-linking telopeptide of type I collagen (CTX-1) by at least 30%, compared to pre-treatment or normal levels, for about 270 days after administration, and wherein the amount of the polypeptide administered is less than or equal to about 1 mg/kg every month. The invention thus also provides a polypeptide of the invention for inhibiting RANK-L mediated bone resorption and/or osteoclast activity, wherein the polypeptide is administered in an amount less than or equal to about 1 mg/kg every month and wherein serum levels of CTX-1 are reduced by at least 30%, compared to pre-treatment or normal levels, and maintained at at least 30% for about 270 days after administration.

In some embodiments, the amount of the polypeptide administered is effective to reduce serum level of cross-linking telopeptide of type I collagen (CTX-1) by at least 30% by 8 hours after administration.

In some embodiments, the amount of the polypeptide administered is effective to reduce serum level of cross-linking telopeptide of type I collagen (CTX-1) by at least 45% by 8 hours after administration.

In some embodiments, the amount of the polypeptide administered is effective to reduce serum level of cross-linking telopeptide of type I collagen (CTX-1) by at least 70% by 8 hours after administration.

In some embodiments, the polypeptide is administered as a single dose.

In some embodiments, the polypeptide is administered subcutaneously.

In some embodiments, bone resorption is inhibited in the subject as determined by ELISA assay for CTX-1.

In some embodiments, the subject has osteoporosis, for example a human subject, such as a female human subject, and in some particular embodiments a post-menopausal female human subject.

According to another aspect of the invention, methods for inhibiting bone resorption or osteoclast activity in a subject are provided. The methods include administering to the subject a polypeptide that specifically binds Receptor Activator of Nuclear Factor kappa B Ligand (RANKL) (polypeptide of the invention). The amount of the polypeptide administered is effective to reduce N-terminal telopeptide of type I collagen (NTX-1) by at least 30%, determined as ratio of NTX-1 to creatinine in urine, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce urine levels of N-terminal telopeptide of type I collagen (NTX-1) by at least 30%, compared to pre-treatment or normal levels, and to maintain urine levels of N-terminal telopeptide of type I collagen (NTX-1) at at least 30% for at least about 30 days after administration. In some embodiments, the polypeptide is administered in an amount of at least 0.01 mg/kg. In some embodiments, the polypeptide is administered in an amount from about 0.01 mg/kg to about 0.1 mg/kg. In other embodiments, the NTX-1 is reduced by at least 30%, compared to pre-treatment or normal levels, for about 30 days after administration, and the polypeptide is administered in an amount of less than or equal to 0.01 mg/kg.

In some embodiments, the NTX-1 is reduced by at least 30%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 30%, compared to pre-treatment or normal levels, and to maintain urine levels of NTX-1 at at least 30% for at least 60 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the NTX-1 is reduced by at least 30%, compared to pre-treatment or normal levels, for about 60 days after administration, and the polypeptide is administered in an amount of less than or equal to 0.01 mg/kg.

In some embodiments, the NTX-1 is reduced by at least 30%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 30%, compared to pre-treatment or normal levels, and to maintain urine levels of NTX-1 at at least 30% for at least 90 days after administration. In some embodiments, the polypeptide is administered in an amount of at least 0.03 mg/kg. In certain embodiments, the polypeptide is administered in an amount from about 0.03 mg/kg to about 0.3 mg/kg. In other embodiments, the NTX-1 is reduced by at least 30%, compared to pre-treatment or normal levels, for about 90 days after administration, and the polypeptide is administered in an amount of less than or equal to 0.03 mg/kg.

In some embodiments, the NTX-1 is reduced by at least 30%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 30%, compared to pre-treatment or normal levels, and to maintain urine levels of NTX-1 at at least 30% for at least 120 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the NTX-1 is reduced by at least 30%, compared to pre-treatment or normal levels, for about 120 days after administration, and the polypeptide is administered in an amount of less than or equal to 0.1 mg/kg.

In some embodiments, the NTX-1 is reduced by at least 30%, compared to pre-treatment or normal levels, for at least 180 days (or 6 months) after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 30%, compared to pre-treatment or normal levels, and to maintain urine levels of NTX-1 at at least 30% for at least 180 days (or 6 months) after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 30%, compared to pre-treatment or normal levels, for about 180 days (or 6 months) after administration, and the polypeptide is administered in an amount of less than or equal to 1 mg/kg.

In some embodiments, the NTX-1 is reduced by at least 30%, compared to pre-treatment or normal levels, for at least 10 months after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 30%, compared to pre-treatment or normal levels and to maintain urine levels of NTX-1 at at least 30% for at least 10 months after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 30%, compared to pre-treatment or normal levels, for about 10 months after administration, and the polypeptide is administered in an amount of less than or equal to 1 mg/kg.

In some embodiments, the NTX-1 is reduced by at least 30%, compared to pre-treatment or normal levels, for at least 12 months (or about 360 days) after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 30%, compared to pre-treatment or normal levels, and to maintain urine levels of NTX-1 at at least 30% for at least 12 months (or about 360 days) after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 30%, compared to pre-treatment or normal levels, for about 12 months (or about 360 days) after administration, and the polypeptide is administered in an amount of less than or equal to 1 mg/kg.

In some embodiments, the amount of the polypeptide administered is effective to reduce N-terminal telopeptide of type I collagen (NTX-1) by at least 45%, determined as ratio of NTX-1 to creatinine in urine, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at at least 45% for at least about 30 days after administration. In some embodiments, the polypeptide is administered in an amount of at least 0.01 mg/kg. In some embodiments, the polypeptide is administered in an amount from about 0.01 mg/kg to about 0.1 mg/kg. In some embodiments, the polypeptide is administered in an amount from about 0.01 mg/kg to about 3 mg/kg. In other embodiments, the NTX-1 is reduced by at least 45%, compared to pre-treatment or normal levels, for about 30 days after administration, and the polypeptide is administered in an amount of less than or equal to 0.01 mg/kg.

In some embodiments, the NTX-1 is reduced by at least 45%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at at least 45% for at least 60 days after administration. In some embodiments, the polypeptide is administered in an amount of at least 0.03 mg/kg. In certain embodiments, the polypeptide is administered in an amount from about 0.03 mg/kg to about 0.1 mg/kg. In other embodiments, the NTX-1 is reduced by at least 45%, compared to pre-treatment or normal levels, for about 60 days after administration, and the polypeptide is administered in an amount of less than or equal to 0.03 mg/kg.

In some embodiments, the NTX-1 is reduced by at least 45%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at at least 45% for at least 90 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the NTX-1 is reduced by at least 45%, compared to pre-treatment or normal levels, for about 90 days after administration, and the polypeptide is administered in an amount of less than or equal to 0.1 mg/kg.

In some embodiments, the NTX-1 is reduced by at least 45%, compared to pre-treatment or normal levels, for about 30 days to 3 months after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at at least 45% for at least about 30 days to 3 months after administration. In some embodiments, the polypeptide is administered in an amount from about 0.01 mg/kg to about 0.3 mg/kg. In some embodiments, the polypeptide is administered in an amount from about 0.03 mg/kg to about 0.3 mg/kg. In some embodiments, the NTX-1 is reduced by at least 45%, compared to pre-treatment or normal levels, for about 30 days after administration, and the polypeptide is administered in an amount from about 0.03 mg/kg to about 0.3 mg/kg. In other embodiments, the NTX-1 is reduced by at least 45%, compared to pre-treatment or normal levels, for about 30 days after administration, and the polypeptide is administered in an amount of less than or equal to 0.03 mg/kg.

In some embodiments, the NTX-1 is reduced by at least 45%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at at least 45% for at least 120 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the NTX-1 is reduced by at least 45%, compared to pre-treatment or normal levels, for about 120 days after administration, and the polypeptide is administered in an amount of less than or equal to 0.1 mg/kg.

In some embodiments, the NTX-1 is reduced by at least 45%, compared to pre-treatment or normal levels, for at least 150 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at at least 45% for at least 150 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the NTX-1 is reduced by at least 45%, compared to pre-treatment or normal levels, for about 150 days after administration, and the polypeptide is administered in an amount of less than or equal to 0.1 mg/kg.

In some embodiments, the NTX-1 is reduced by at least 45%, compared to pre-treatment or normal levels, for about 3 months to 6 months after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at least 45% for about 3 months to 6 months after administration. In some embodiments, the polypeptide is administered in an amount from about 0.3 mg/kg to about 1 mg/kg. In some embodiments, the NTX-1 is reduced by at least 45%, compared to pre-treatment or normal levels, for about 3 months after administration, and the polypeptide is administered in an amount from about 0.3 mg/kg to about 1 mg/kg. In other embodiments, the NTX-1 is reduced by at least 45%, compared to pre-treatment or normal levels, for about 3 months after administration, and the polypeptide is administered in an amount of less than or equal to 0.3 mg/kg.

In some embodiments, the NTX-1 is reduced by at least 45%, compared to pre-treatment or normal levels, for at least 180 days (or 6 months) after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at least 45% for at least 180 days (or 6 months) after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 45%, compared to pre-treatment or normal levels, for about 180 days (or 6 months) after administration, and the polypeptide is administered in an amount of less than or equal to 1 mg/kg.

In some embodiments, the NTX-1 is reduced by at least 45%, compared to pre-treatment or normal levels, for at least 210 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at least 45% for at least 210 days after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 45%, compared to pre-treatment or normal levels, for about 210 days after administration, and the polypeptide is administered in an amount of less than or equal to 1 mg/kg.

In some embodiments, the NTX-1 is reduced by at least 45%, compared to pre-treatment or normal levels, for at least 6 months to 1 year after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 45%, compared to pre-treatment or normal levels, and to maintain urine levels of NTX-1 at least 45% for about 6 months to 1 year after administration. In some embodiments, the polypeptide is administered in an amount from about 1 mg/kg to about 10 mg/kg. In some embodiments, the polypeptide is administered in an amount from about 1 mg/kg to about 3 mg/kg. In some embodiments, the NTX-1 is reduced by at least 45%, compared to pre-treatment or normal levels, for about 6 months after administration, and the polypeptide is administered in an amount from about 1 mg/kg to about 3 mg/kg. In other embodiments, the NTX-1 is reduced by at least 45%, compared to pre-treatment or normal levels, for about 6 months after administration, and the polypeptide is administered in an amount of less than or equal to 1 mg/kg.

In some embodiments, the amount of the polypeptide administered is effective to reduce N-terminal telopeptide of type I collagen (NTX-1) by at least 70%, determined as ratio of NTX-1 to creatinine in urine, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce urine levels of NTX-1 by at least 70%, compared to pre-treatment or normal levels, and to maintain urine levels of NTX-1 at at least 70% for at least about 30 days after administration. In some embodiments, the polypeptide is administered in an amount of at least 0.1 mg/kg. In some embodiments, the polypeptide is administered in an amount from about 0.1 mg/kg to about 1 mg/kg. In other embodiments, the NTX-1 is reduced by at least 70%, compared to pre-treatment or normal levels, for about 30 days after administration, and the polypeptide is administered in an amount of less than or equal to 0.1 mg/kg.

In some embodiments, the NTX-1 is reduced by at least 70%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 70%, compared to pre-treatment or normal levels, and to maintain urine levels of NTX-1 at at least 70% for at least 60 days after administration. In some embodiments, the polypeptide is administered in an amount of at least 0.3 mg/kg. In certain embodiments, the polypeptide is administered in an amount from about 0.3 mg/kg to about 3 mg/kg. In other embodiments, the NTX-1 is reduced by at least 70%, compared to pre-treatment or normal levels, for about 60 days after administration, and the polypeptide is administered in an amount of less than or equal to 0.3 mg/kg.

In some embodiments, the NTX-1 is reduced by at least 70%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 70%, compared to pre-treatment or normal levels, and to maintain urine levels of NTX-1 at at least 70% for at least 90 days after administration. In some embodiments, the polypeptide is administered in an amount of at least 0.3 mg/kg. In certain embodiments, the polypeptide is administered in an amount from about 0.3 mg/kg to about 3 mg/kg. In other embodiments, the NTX-1 is reduced by at least 70%, compared to pre-treatment or normal levels, for about 90 days after administration, and the polypeptide is administered in an amount of less than or equal to 0.3 mg/kg.

In some embodiments, the NTX-1 is reduced by at least 70%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 70%, compared to pre-treatment or normal levels, and to maintain urine levels of NTX-1 at least 70% for at least 120 days after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 70%, compared to pre-treatment or normal levels, for about 120 days after administration, and the polypeptide is administered in an amount of less than or equal to 1 mg/kg.

In some embodiments, the NTX-1 is reduced by at least 20%, compared to pre-treatment or normal levels, for at least 90 days after administration, such as for at least 120 days after administration, for at least 150 days after administration, for at least 180 days after administration, for times intermediate to these, or longer as described elsewhere herein and as shown in the examples and figures presented herein. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels, and to maintain urine levels of NTX-1 at at least 20% for at least 90 days after administration, for at least 120 days after administration, for at least 150 days after administration, for at least 180 days after administration, for times intermediate to these, or longer as described elsewhere herein and as shown in the examples and figures presented herein.

In some embodiments, the amount of the polypeptide administered is effective to reduce N-terminal telopeptide of type I collagen (NTX-1)-1) by at least 20%, determined as ratio of NTX-1 to creatinine in urine, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce urine levels of N-terminal telopeptide of type I collagen (NTX-1) by at least 200%, compared to pre-treatment or normal levels, and to maintain urine levels of N-terminal telopeptide of type I collagen (NTX-1) at at least 20% for at least about 30 days after administration. In some embodiments, the polypeptide is administered in an amount of at least 0.01 mg/kg. In some embodiments, the polypeptide is administered in an amount from about 0.01 mg/kg to about 0.1 mg/kg. In other embodiments, the NTX-1 is reduced by at least 30%, compared to pre-treatment or normal levels, for about 30 days after administration, and the polypeptide is administered in an amount of less than or equal to 0.01 mg/kg.

In some embodiments, the NTX-1 is reduced by at least 20%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels, and to maintain urine levels of NTX-1 at at least 20% for at least 60 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the NTX-1 is reduced by at least 20%, compared to pre-treatment or normal levels, for about 60 days after administration, and the polypeptide is administered in an amount of less than or equal to 0.01 mg/kg.

In some embodiments, the NTX-1 is reduced by at least 20%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels, and to maintain urine levels of NTX-1 at at least 20% for at least 90 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the NTX-1 is reduced by at least 20%, compared to pre-treatment or normal levels, for about 90 days after administration, and the polypeptide is administered in an amount of less than or equal to 0.01 mg/kg.

In some embodiments, the NTX-1 is reduced by at least 20%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels, and to maintain urine levels of NTX-1 at at least 20% for at least 120 days after administration. In some embodiments, the polypeptide is administered in an amount of at least 0.01 mg/kg. In certain embodiments, the polypeptide is administered in an amount from about 0.01 mg/kg to about 0.1 mg/kg. In other embodiments, the NTX-1 is reduced by at least 20%, compared to pre-treatment or normal levels, for about 120 days after administration, and the polypeptide is administered in an amount of less than or equal to 0.01 mg/kg.

In some embodiments, the NTX-1 is reduced by at least 20%, compared to pre-treatment or normal levels, for at least 180 days (or 6 months) after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels, and to maintain urine levels of NTX-1 at at least 20% for at least 180 days (or 6 months) after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the NTX-1 is reduced by at least 20%, compared to pre-treatment or normal levels, for about 180 days (or 6 months) after administration, and the polypeptide is administered in an amount of less than or equal to 0.1 mg/kg.

In some embodiments, the NTX-1 is reduced by at least 20%, compared to pre-treatment or normal levels, for at least 10 months after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels and to maintain urine levels of NTX-1 at at least 20% for at least 10 months after administration. In some embodiments, the polypeptide is administered in an amount of at least 1. Mg/kg. In certain embodiments, the polypeptide is administered in an amount from about 1 mg/kg to about 10 mg/kg. In other embodiments, the NTX-1 is reduced by at least 20%, compared to pre-treatment or normal levels, for about 10 months after administration, and the polypeptide is administered in an amount of less than or equal to 1 mg/kg.

In some embodiments, the NTX-1 is reduced by at least 20%, compared to pre-treatment or normal levels, for at least 12 months (or about 360 days) after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 20%, compared to pre-treatment or normal levels, and to maintain urine levels of NTX-1 at at least 20% for at least 12 months (or about 360 days) after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 20%, compared to pre-treatment or normal levels, for about 12 months (or about 360 days) after administration, and the polypeptide is administered in an amount of less than or equal to 1 mg/kg.

In some embodiments, the amount of the polypeptide administered is effective to reduce N-terminal telopeptide of type I collagen (NTX-1) by at least 80%, determined as ratio of NTX-1 to creatinine in urine, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce urine levels of NTX-1 by at least 80%, compared to pre-treatment or normal levels, and to maintain urine levels of NTX-1 at at least 80% for at least about 30 days after administration. In some embodiments, the polypeptide is administered in an amount of at least 0.3 mg/kg. In some embodiments, the polypeptide is administered in an amount from about 0.3 mg/kg to about 1 mg/kg. In some embodiments, the polypeptide is administered in an amount from about 0.3 mg/kg to about 3 mg/kg. In other embodiments, the NTX-1 is reduced by at least 80%, compared to pre-treatment or normal levels, for about 30 days after administration, and the polypeptide is administered in an amount of less than or equal to 0.3 mg/kg.

In some embodiments, the NTX-1 is reduced by at least 80%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 80%, compared to pre-treatment or normal levels, and to maintain urine levels of NTX-1 at at least 80% for at least 60 days after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 80%, compared to pre-treatment or normal levels, for about 60 days after administration, and the polypeptide is administered in an amount of less than or equal to 1 mg/kg.

In some embodiments, the NTX-1 is reduced by at least 80%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 80%, compared to pre-treatment or normal levels, and to maintain urine levels of NTX-1 at at least 80% for at least 90 days after administration. In some embodiments, the polypeptide is administered in an amount of at least 1 mg/kg. In certain embodiments, the polypeptide is administered in an amount from about 1 mg/kg to about 10 mg/kg. In other embodiments, the NTX-1 is reduced by at least 80%, compared to pre-treatment or normal levels, for about 90 days after administration, and the polypeptide is administered in an amount of less than or equal to 1 mg/kg.

In some embodiments, the NTX-1 is reduced by at least 80%, compared to pre-treatment or normal levels, for about 30 days to 3 months after administration. Accordingly, the invention also relates to a polypeptide of the invention for inhibiting RANK-L mediated bone resorption and/or osteoclast activity, wherein the amount of the polypeptide administered is effective to reduce urine levels of NTX-1 by at least 80%, compared to pre-treatment or normal levels, and to maintain urine levels of NTX-1 at at least 80% for at least about 30 days to 3 months after administration. In some embodiments, the polypeptide is administered in an amount from about 0.1 mg/kg to about 1 mg/kg. In some embodiments, the polypeptide is administered in an amount from about 0.3 mg/kg to about 1 mg/kg. In some embodiments, the NTX-1 is reduced by at least 80%, compared to pre-treatment or normal levels, for about 30 days after administration, and the polypeptide is administered in an amount from about 0.3 mg/kg to about 1 mg/kg.

In some embodiments, the ratio of NTX-1 to creatinine in urine in the subject is determined by ELISA assay for NTX-1.

In some embodiments, the amount of the polypeptide administered is effective to reduce urine levels of NTX-1 by at least 30% by 8 hours after administration.

In some embodiments, the amount of the polypeptide administered is effective to reduce urine levels of NTX-1 by at least 45% by 8 hours after administration.

In some embodiments, the amount of the polypeptide administered is effective to reduce urine levels of NTX-1 by at least 70% by 8 hours after administration.

In some embodiments, the polypeptide is administered as a single dose.

In some embodiments, the polypeptide is administered subcutaneously.

In some embodiments, the subject has osteoporosis, for example a human subject, such as a female human subject, and in some particular embodiments a post-menopausal female human subject.

According to another aspect of the invention, methods for inhibiting bone resorption or osteoclast activity in a subject are provided. The methods include administering to the subject a polypeptide that specifically binds Receptor Activator of Nuclear Factor kappa B Ligand (RANKL) (polypeptide of the invention). The amount of the polypeptide administered is effective to reduce serum level of tartrate-resistant acid phosphatase isoform 5b (TRACP5b) by at least 30%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of TRACP5b by at least 30%, compared to pre-treatment or normal levels, and to maintain serum levels of TRACP5b at at least 30% for at least about 30 days after administration. In some embodiments, the polypeptide is administered in an amount of at least 0.03 mg/kg. In some embodiments, the polypeptide is administered in an amount from about 0.03 mg/kg to about 0.3 mg/kg. In other embodiments, the TRACP5b is reduced by at least 30%, compared to pre-treatment or normal levels, for about 30 days after administration, and the polypeptide is administered in an amount of less than or equal to 0.03 mg/kg.

In some embodiments, the TRACP5b is reduced by at least 30%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce serum levels of TRACP5b by at least 30%, compared to pre-treatment or normal levels, and to maintain serum levels of TRACP5b at at least 30% for at least 60 days after administration. In some embodiments, the polypeptide is administered in an amount of at least 0.03 mg/kg. In certain embodiments, the polypeptide is administered in an amount from about 0.03 mg/kg to about 0.3 mg/kg. In other embodiments, the TRACP5b is reduced by at least 30%, compared to pre-treatment or normal levels, for about 60 days after administration, and the polypeptide is administered in an amount of less than or equal to 0.03 mg/kg.

In some embodiments, the TRACP5b is reduced by at least 30%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce serum levels of TRACP5b by at least 30%, compared to pre-treatment or normal levels, and to maintain serum levels of TRACP5b at at least 30% for at least 90 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the TRACP5b is reduced by at least 30%, compared to pre-treatment or normal levels, for about 90 days after administration, and the polypeptide is administered in an amount of less than or equal to 0.1 mg/kg.

In some embodiments, the TRACP5b is reduced by at least 30%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce serum levels of TRACP5b by at least 30%, compared to pre-treatment or normal levels, and to maintain serum levels of TRACP5b at at least 30% for at least 120 days after administration. In some embodiments, the polypeptide is administered in an amount of at least 0.3 mg/kg. In certain embodiments, the polypeptide is administered in an amount from about 0.3 mg/kg to about 3 mg/kg. In other embodiments, the TRACP5b is reduced by at least 30%, compared to pre-treatment or normal levels, for about 120 days after administration, and the polypeptide is administered in an amount of less than or equal to 0.3 mg/kg.

According to another aspect of the invention, the amount of the polypeptide administered is effective to reduce serum level of tartrate-resistant acid phosphatase isoform 5b (TRACP5b) by at least 45%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of TRACP5b by at least 45%, compared to pre-treatment or normal levels, and to maintain serum levels of TRACP5b at at least 45% for at least about 30 days after administration. In some embodiments, the polypeptide is administered in an amount of at least 0.1 mg/kg. In some embodiments, the polypeptide is administered in an amount from about 0.1 mg/kg to about 1 mg/kg. In other embodiments, the TRACP5b is reduced by at least 45%, compared to pre-treatment or normal levels, for about 30 days after administration, and the polypeptide is administered in an amount of less than or equal to 0.1 mg/kg.

In some embodiments, the TRACP5b is reduced by at least 45%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce serum levels of TRACP5b by at least 45%, compared to pre-treatment or normal levels, and to maintain serum levels of TRACP5b at at least 45% for at least 60 days after administration. In some embodiments, the polypeptide is administered in an amount of at least 0.3 mg/kg. In certain embodiments, the polypeptide is administered in an amount from about 0.3 mg/kg to about 3 mg/kg. In other embodiments, the TRACP5b is reduced by at least 45%, compared to pre-treatment or normal levels, for about 60 days after administration, and the polypeptide is administered in an amount of less than or equal to 0.3 mg/kg.

In some embodiments, the TRACP5b is reduced by at least 45%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce serum levels of TRACP5b by at least 45%, compared to pre-treatment or normal levels, and to maintain serum levels of TRACP5b at at least 45% for at least 90 days after administration. In some embodiments, the polypeptide is administered in an amount of at least 0.3 mg/kg. In certain embodiments, the polypeptide is administered in an amount from about 0.3 mg/kg to about 3 mg/kg. In other embodiments, the TRACP5b is reduced by at least 45%, compared to pre-treatment or normal levels, for about 90 days after administration, and the polypeptide is administered in an amount of less than or equal to 0.3 mg/kg.

In some embodiments, the polypeptide is administered as a single dose.

In some embodiments, the polypeptide is administered subcutaneously.

In some embodiments, bone resorption is inhibited in the subject as determined by ELISA assay for TRACP5b.

In some embodiments, the subject has osteoporosis, for example a human subject, such as a female human subject, and in some particular embodiments a post-menopausal female human subject.

According to another aspect of the invention, methods for inhibiting bone resorption or osteoclast activity in a subject are provided. The methods include administering to the subject a polypeptide that specifically binds Receptor Activator of Nuclear Factor kappa B Ligand (RANKL) (polypeptide of the invention). The amount of the polypeptide administered is effective to reduce serum level of N-terminal propeptide of type I procollagen (P1NP) by at least 30%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of P1NP by at least 30%, compared to pre-treatment or normal levels, and to maintain serum levels of P1NP at at least 30% for at least about 30 days after administration. In some embodiments, the polypeptide is administered in an amount of at least 0.003 mg/kg. In some embodiments, the polypeptide is administered in an amount from about 0.003 mg/kg to about 0.03 mg/kg. In other embodiments, the P1NP is reduced by at least 30%, compared to pre-treatment or normal levels, for about 30 days after administration, and the polypeptide is administered in an amount of less than or equal to 0.003 mg/kg.

In some embodiments, P1NP is reduced by at least 30%, compared to pre-treatment or normal levels, for at least 60 days after administration. The invention thus also relates to a polypeptide of the invention for inhibiting RANK-L mediated bone resorption and/or osteoclast activity, wherein the amount of the polypeptide administered is effective to reduce serum levels of P1NP by at least 30%, compared to pre-treatment or normal levels, and to maintain serum levels of P1NP at at least 30% for at least about 60 days after administration. In some embodiments, the polypeptide is administered in an amount of at least 0.003 mg/kg. In some embodiments, the polypeptide is administered in an amount from about 0.003 mg/kg to about 0.03 mg/kg. In other embodiments, the P1NP is reduced by at least 30%, compared to pre-treatment or normal levels, for about 60 days after administration, and the polypeptide is administered in an amount of less than or equal to 0.003 mg/kg.

In some embodiments, P1NP is reduced by at least 30%, compared to pre-treatment or normal levels, for at least 90 days after administration. The invention thus also relates to a polypeptide of the invention for inhibiting RANK-L mediated bone resorption and/or osteoclast activity, wherein the amount of the polypeptide administered is effective to reduce serum levels of P1NP by at least 30%, compared to pre-treatment or normal levels, and to maintain serum levels of P1NP at at least 30% for at least about 90 days after administration. In some embodiments, the polypeptide is administered in an amount of at least 0.01 mg/kg. In some embodiments, the polypeptide is administered in an amount from about 0.01 mg/kg to about 0.1 mg/kg. In other embodiments, the P1NP is reduced by at least 30%, compared to pre-treatment or normal levels, for about 90 days after administration, and the polypeptide is administered in an amount of less than or equal to 0.01 mg/kg.

In some embodiments, P1NP is reduced by at least 30%, compared to pre-treatment or normal levels, for at least 120 days after administration. The invention thus also relates to a polypeptide of the invention for inhibiting RANK-L mediated bone resorption and/or osteoclast activity, wherein the amount of the polypeptide administered is effective to reduce serum levels of P1NP by at least 30%, compared to pre-treatment or normal levels, and to maintain serum levels of P1NP at at least 30% for at least about 120 days after administration. In some embodiments, the polypeptide is administered in an amount of at least 0.01 mg/kg. In some embodiments, the polypeptide is administered in an amount from about 0.01 mg/kg to about 0.1 mg/kg. In other embodiments, the P1NP is reduced by at least 30%, compared to pre-treatment or normal levels, for about 120 days after administration, and the polypeptide is administered in an amount of less than or equal to 0.01 mg/kg.

According to another aspect of the invention, the amount of the polypeptide administered is effective to reduce serum level of N-terminal propeptide of type I procollagen (P1NP) by at least 45%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of P1NP by at least 45%, compared to pre-treatment or normal levels, and to maintain serum levels of P1NP at at least 45% for at least about 30 days after administration. In some embodiments, the polypeptide is administered in an amount of at least 0.03 mg/kg. In some embodiments, the polypeptide is administered in an amount from about 0.03 mg/kg to about 0.3 mg/kg. In other embodiments, the P1NP is reduced by at least 45%, compared to pre-treatment or normal levels, for about 30 days after administration, and the polypeptide is administered in an amount of less than or equal to 0.03 mg/kg.

In some embodiments, the P1NP is reduced by at least 45%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce serum levels of P1NP by at least 45%, compared to pre-treatment or normal levels, and to maintain serum levels of P1NP at at least 45% for at least 60 days after administration. In some embodiments, the polypeptide is administered in an amount of at least 0.03 mg/kg. In certain embodiments, the polypeptide is administered in an amount from about 0.03 mg/kg to about 0.3 mg/kg. In other embodiments, the P1NP is reduced by at least 45%, compared to pre-treatment or normal levels, for about 30 days after administration, and the polypeptide is administered in an amount of less than or equal to 0.03 mg/kg.

In some embodiments, the P1NP is reduced by at least 45%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce serum levels of P1NP by at least 45%, compared to pre-treatment or normal levels, and to maintain serum levels of P1NP at at least 45% for at least 90 days after administration. In some embodiments, the polypeptide is administered in an amount of at least 0.03 mg/kg. In certain embodiments, the polypeptide is administered in an amount from about 0.03 mg/kg to about 0.3 mg/kg. In other embodiments, the P1NP is reduced by at least 45%, compared to pre-treatment or normal levels, for about 90 days after administration, and the polypeptide is administered in an amount of less than or equal to 0.03 mg/kg.

In some embodiments, the P1NP is reduced by at least 45%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce serum levels of P1NP by at least 45%, compared to pre-treatment or normal levels, and to maintain serum levels of P1NP at at least 45% for at least 120 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the P1NP is reduced by at least 45%, compared to pre-treatment or normal levels, for about 120 days after administration, and the polypeptide is administered in an amount of less than or equal to 0.1 mg/kg.

According to another aspect of the invention, the amount of the polypeptide administered is effective to reduce serum level of N-terminal propeptide of type I procollagen (P1NP) by at least 70%, compared to pre-treatment or normal levels, for at least 30 days after administration. The invention thus also relates to a polypeptide of the invention for inhibiting RANK-L mediated bone resorption and/or osteoclast activity, wherein the amount of the polypeptide administered is effective to reduce serum levels of P1NP by at least 70%, compared to pre-treatment or normal levels, and to maintain serum levels of P1NP at at least 70% for at least about 30 days after administration. In some embodiments, the polypeptide is administered in an amount of at least 0.1 mg/kg. In some embodiments, the polypeptide is administered in an amount from about 0.1 mg/kg to about 1 mg/kg. In other embodiments, the P1NP is reduced by at least 70%, compared to pre-treatment or normal levels, for about 30 days after administration, and the polypeptide is administered in an amount of less than or equal to 0.1 mg/kg.

In some embodiments, the P1NP is reduced by at least 70%, compared to pre-treatment or normal levels, for at least 60 days after administration. Accordingly, the invention also relates to a polypeptide of the invention for inhibiting RANK-L mediated bone resorption and/or osteoclast activity, wherein the amount of the polypeptide administered is effective to reduce serum levels of P1NP by at least 70%, compared to pre-treatment or normal levels, and to maintain serum levels of P1NP at at least 70% for at least 60 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the P1NP is reduced by at least 70%, compared to pre-treatment or normal levels, for about 30 days after administration, and the polypeptide is administered in an amount of less than or equal to 0.1 mg/kg.

In some embodiments, the P1NP is reduced by at least 70%, compared to pre-treatment or normal levels, for at least 90 days after administration. Accordingly, the invention also relates to a polypeptide of the invention for inhibiting RANK-L mediated bone resorption and/or osteoclast activity, wherein the amount of the polypeptide administered is effective to reduce serum levels of P1NP by at least 70%, compared to pre-treatment or normal levels, and to maintain serum levels of P1NP at at least 70% for at least 90 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the P1NP is reduced by at least 70%, compared to pre-treatment or normal levels, for about 90 days after administration, and the polypeptide is administered in an amount of less than or equal to 0.1 mg/kg.

In some embodiments, the P1NP is reduced by at least 70%, compared to pre-treatment or normal levels, for at least 120 days after administration. Accordingly, the invention also relates to a polypeptide of the invention for inhibiting RANK-L mediated bone resorption and/or osteoclast activity, wherein the amount of the polypeptide administered is effective to reduce serum levels of P1NP by at least 70%, compared to pre-treatment or normal levels, and to maintain serum levels of P1NP at at least 70% for at least 120 days after administration. In some embodiments, the polypeptide is administered in an amount of at least 0.1 mg/kg. In certain embodiments, the polypeptide is administered in an amount from about 0.1 mg/kg to about 1 mg/kg. In other embodiments, the P1NP is reduced by at least 70%, compared to pre-treatment or normal levels, for about 120 days after administration, and the polypeptide is administered in an amount of less than or equal to 0.1 mg/kg.

In some embodiments, the polypeptide is administered as a single dose.

In some embodiments, the polypeptide is administered subcutaneously.

In some embodiments, bone resorption is inhibited in the subject as determined by radioimmunoassay for P1NP.

In some embodiments, the subject has osteoporosis, for example a human subject, such as a female human subject, and in some particular embodiments a post-menopausal female human subject.

The method of the present invention can be used for prevention and/or treatment of subjects that suffer bone diseases and/or disorders such as e.g. osteoporosis, including, but not limited to, primary osteoporosis, endocrine osteoporosis (including, but not limited to, hyperthyroidism, hyperparathyroidism, Cushing's syndrome, and acromegaly), hereditary and congenital forms of osteoporosis (including, but not limited to, osteogenesis imperfecta, homocystinuria, Menkes' syndrome, Riley-Day syndrome), osteoporosis due to immobilization of extremities, glucocorticoid-induced osteoporosis and post-menopausal osteoporosis.

In some embodiments, the polypeptide of the invention comprises one or more immunoglobulin single variable domains that specifically bind RANKL. In some embodiments, the polypeptide of the invention has an apparent $K_D$ for binding to recombinant soluble RANKL (sRANKL) of 0.01-0.05 nM, preferably about 0.04 nM, as determined by Biacore. In some embodiments, the immunoglobulin single variable domains comprise or consist of one or more VHH domains, one or more humanized VHH domains and/or one or more camelized VH domains. In some embodiments, the polypeptide comprises one or more domain antibodies that specifically bind RANKL, one or more amino acid sequences that specifically bind RANKL and that are suitable for use as a domain antibody, one or more single domain antibodies that specifically bind RANKL, one or more amino acid sequences that specifically bind RANKL and that are suitable for use as a single domain antibody, or one or more "dAb"s that specifically bind RANKL.

In some embodiments, the polypeptide is a multivalent construct comprising two or more immunoglobulin single variable domains that specifically bind RANKL. In some embodiments, the multivalent construct comprises two immunoglobulin single variable domains that specifically bind RANKL.

Preferred polypeptides of the invention are multivalent constructs that comprise or consist of one or more immunoglobulin single variable domains that consist of 4 framework regions (FR1 to FR4, respectively) and 3 complementarity determining regions (CDR1 to CDR3, respectively), in which: CDR1 consists of SYPMG (SEQ ID NO: 1), CDR2 consists of SITGSGGSTYYADSVKG (SEQ ID NO: 2) and CDR3 consists of YIRPDTYLSRDYRKY (SEQ ID NO:3).

In some embodiments, the polypeptide is a multivalent construct that comprises SEQ ID NO: 755 of US 2010/0104568 (EVQLVESGGGLVQPGGSLRLSCAASGFTFS-SYPMGWFRQAPGKGREFVSSITGSGGSTYYADSVK-

GRFTISRDNA KNTLYLQMNSLRPEDTAVYYCAAYIR-PDTYLSRDYRKYDYWGQGTLVTVSS; SEQ ID NO: 10).

In some embodiments, the polypeptide is a multivalent construct comprising or consisting of two or more immunoglobulin single variable domains as defined above. In some embodiments, the multivalent construct comprises or consists of two immunoglobulin single variable domains as defined above.

In some embodiments, the multivalent construct further comprises at least one half-life extension moiety. In some embodiments, the at least one half-life extension moiety specifically binds a serum protein. In some embodiments, the serum protein is serum albumin, and in particular human serum albumin, thyroxine-binding protein, (human) transferrin, fibrinogen, an immunoglobulin such as IgG, IgE or IgM, or one of the serum proteins listed in WO 04/003019.

In some embodiments, at least one half-life extension moiety comprises or consists of a immunoglobulin single variable domain. In some embodiments, the immunoglobulin single variable domain comprises or consists of a VHH domain, a humanized VHH domain or a camelized VH domain. In some embodiments, the at least one half-life extension moiety comprises a domain antibody, an amino acid sequence that is suitable for use as a domain antibody, a single domain antibody, an amino acid sequence that is suitable for use as a single domain antibody, or a "dAb".

A preferred immunoglobulin single variable domain that binds serum albumin comprises or consists of SEQ ID NO: 791 of US 2010/0104568 (SEQ ID NO: 14).

In some embodiments, the polypeptide of the invention is a multivalent construct that comprises or consists of SEQ ID NO: 759 of US 2010/0104568 (EVQLVESG- GGLVQPGG-SLRLSCAASGFTFSSYPMGWFRQAPGKGREFVS-SITGSGGSTYYADSVKGRFTISRDNA KNTLYLQ-MNSLRPEDTAVYYCAAYIRPDTYLSRDYRKYDYW-GQGTLVTVSSGGGGSGGGSEVQLVESGGGLVQPG NSLRLSCAASGFTFSSFGMSWVRQAPGKGLEWVSS-ISGSGSDTLYADSVKGRFTISRDNAKTTLYLQMNSL-RPEDT AVYYCTIGGSLSRSSQGTLVTVSSGGGGSG-GGSEVQLVESGGGLVQPGGSLRLSCAASGFTFSSYP-MGWFRQAPG KGREFVSSITGSGGSTYYADSVK-GRFTISRDNAKNTLYLQMNSLRPEDTAVYY-CAAYIRPDTYLSRDYRKYDYWGQG TLVTVSS; SEQ ID NO: 12).

In some embodiments, the polypeptide of the invention cross-blocks the binding of SEQ ID NO: 755 of US 2010/0104568 (SEQ ID NO: 10) or SEQ ID NO: 759 of US 2010/0104568 (SEQ ID NO: 12) to RANKL. In some embodiments, the polypeptide of the invention is cross-blocked from binding RANKL by SEQ ID NO: 755 of US 2010/0104568 (SEQ ID NO: 10) or SEQ ID NO: 759 of US 2010/0104568 (SEQ ID NO: 12).

In some embodiments, the at least one half-life extension moiety comprises one or more polyethylene glycol molecules.

In a preferred aspect, the polypeptide of the invention is SEQ ID NO: 12. Accordingly, the invention relates to a method for inhibiting bone resorption and/or osteoclast activity in a subject, said method comprising administering to the subject a polypeptide with SEQ ID NO: 12 in an amount from about 0.003 mg/kg to about 0.01 mg/kg every month, wherein CTX-1 levels in serum are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.003 mg/kg to about 0.01 mg/kg every month and wherein CTX-1 levels in serum are reduced by at least 30%, compared to pre-treatment or normal levels, and maintained (throughout the treatment period) at at least 30%.

In another preferred aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every month, wherein CTX-1 levels in serum are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every month and wherein CTX-1 levels in serum are reduced by at least 45%, compared to pre-treatment or normal levels, and maintained (throughout the treatment period) at at least 45%.

In another preferred aspect, the invention relates to a method for inhibiting bone resorption and/or osteoclast activity in a subject, said method comprising administering to the subject a polypeptide with SEQ ID NO: 12 in an amount from about 0.03 mg/kg to about 0.1 mg/kg every month, wherein CTX-1 levels in serum are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.03 mg/kg to about 0.1 mg/kg every month and wherein CTX-1 levels in serum are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every two months, wherein CTX-1 levels in serum are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every two months and wherein CTX-1 levels in serum are reduced by at least 30%, compared to pre-treatment or normal levels, and maintained (throughout the treatment period) at at least 30%.

In another preferred aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every two months, wherein CTX-1 levels in serum are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every two months and wherein CTX-1 levels in serum are reduced by at least 45%, compared to pre-treatment or normal levels, and maintained (throughout the treatment period) at at least 45%.

In another preferred aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every two months, wherein CTX-1 levels in serum are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every two months and wherein CTX-1 levels in serum are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every three months, wherein CTX-1 levels in serum are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every three months and wherein CTX-1 levels in serum are reduced by at least 30%, compared to pre-treatment or normal levels, and maintained (throughout the treatment period) at at least 30%.

In another preferred aspect, the invention relates to a method for inhibiting bone resorption and/or osteoclast activity in a subject, said method comprising administering to the subject a polypeptide with SEQ ID NO: 12 in an amount from about 0.03 mg/kg to about 0.1 mg/kg every three months, wherein CTX-1 levels in serum are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.03 mg/kg to about 0.1 mg/kg every three months and wherein CTX-1 levels in serum are reduced by at least 45%, compared to pre-treatment or normal levels, and maintained (throughout the treatment period) at at least 45%.

In another preferred aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every three months, wherein CTX-1 levels in serum are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every three months and wherein CTX-1 levels in serum are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every four months, wherein CTX-1 levels in serum are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every four months and wherein CTX-1 levels in serum are reduced by at least 30%, compared to pre-treatment or normal levels, and maintained (throughout the treatment period) at at least 30%.

In another preferred aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every four months, wherein CTX-1 levels in serum are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every four months and wherein CTX-1 levels in serum are reduced by at least 450%, compared to pre-treatment or normal levels, and maintained (throughout the treatment period) at at least 45%.

In another preferred aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every four months, wherein CTX-1 levels in serum are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every four months and wherein CTX-1 levels in serum are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every month, wherein NTX-1 levels, determined as ratio of NTX-1 to creatine in urine, are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every month and wherein NTX-1 levels in urine are reduced by at least 30%, compared to pre-treatment or normal levels, and maintained (throughout the treatment period) at at least 30%.

In another aspect, the invention relates to a method for inhibiting bone resorption and/or osteoclast activity in a subject, said method comprising administering to the subject a polypeptide with SEQ ID NO: 12 in an amount from about 0.01 mg/kg to about 0.03 mg/kg every month, wherein NTX-1 levels in urine are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.01 mg/kg to about 0.03 mg/kg every month and wherein NTX-1 levels in urine are reduced by at least 45%, compared to pre-treatment or normal levels, and maintained (throughout the treatment period) at at least 45%.

In another aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every month, wherein NTX-1 levels in urine are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every month and wherein NTX-1 levels in urine are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.03 mg/kg to about 0.1 mg/kg every two months, wherein NTX-1 levels in urine are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.03 mg/kg to about 0.1 mg/kg every two months and wherein NTX-1 levels in urine are reduced by at least 30%, compared to pre-treatment or normal levels, and maintained (throughout the treatment period) at at least 30%.

In another aspect, the invention relates to a method for inhibiting bone resorption and/or osteoclast activity in a subject, said method comprising administering to the subject a polypeptide with SEQ ID NO: 12 in an amount from about 0.03 mg/kg to about 0.1 mg/kg every two months, wherein NTX-1 levels in urine are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.03 mg/kg to about 0.1 mg/kg every two months and wherein NTX-1 levels in urine are reduced by at least 45%, compared to pre-treatment or normal levels, and maintained (throughout the treatment period) at at least 45%.

In another aspect, the invention relates to a method for inhibiting bone resorption and/or osteoclast activity in a subject, said method comprising administering to the subject a polypeptide with SEQ ID NO: 12 in an amount from about 0.3 mg/kg to about 1 mg/kg every two months, wherein NTX-1 levels in urine are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.3 mg/kg to about 1 mg/kg every two months and wherein NTX-1 levels in urine are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.03 mg/kg to about 0.1 mg/kg every three months, wherein NTX-1 levels in serum are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.03 mg/kg to about 0.1 mg/kg every three months and wherein NTX-1 levels in urine are reduced by at least 30%, compared to pre-treatment or normal levels, and maintained (throughout the treatment period) at at least 30%.

In another aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every three months, wherein NTX-1 levels in urine are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every three months and wherein NTX-1 levels in urine are reduced by at least 45%, compared to pre-treatment or normal levels, and maintained (throughout the treatment period) at at least 45%.

In another aspect, the invention relates to a method for inhibiting bone resorption and/or osteoclast activity in a subject, said method comprising administering to the subject a polypeptide with SEQ ID NO: 12 in an amount from about 0.3 mg/kg to about 1 mg/kg every three months, wherein NTX-1 levels in urine are reduced by at least 70%, compared to pre-treatment or normal levels, and maintained (throughout the treatment period) at at least 70%. The invention thus also relates to a polypeptide with SEQ ID NO: 12 for inhibiting bone resorption and/or osteoclast activity, wherein the polypeptide is administered in an amount from about 0.3 mg/kg to about 1 mg/kg every three months and wherein NTX-1 levels in urine are reduced by at least 70%, compared to pre-treatment or normal levels, and maintained (throughout the treatment period) at at least 70%.

In another preferred aspect, the invention relates to a method for inhibiting bone resorption and/or osteoclast activity in a subject, said method comprising administering to the subject a polypeptide with SEQ ID NO: 12 in an amount from about 0.03 mg/kg to about 0.1 mg/kg every four months, wherein NTX-1 levels in urine are reduced by at least 30%, compared to pre-treatment or normal levels, and maintained (throughout the treatment period) at at least 30%. The invention thus also relates to a polypeptide with SEQ ID NO: 12 for inhibiting bone resorption and/or osteoclast activity, wherein the polypeptide is administered in an amount from about 0.03 mg/kg to about 0.1 mg/kg every four months and wherein NTX-1 levels in urine are reduced by at least 30%, compared to pre-treatment or normal levels, and maintained (throughout the treatment period) at at least 30%.

In another aspect, the invention relates to a method for inhibiting bone resorption and/or osteoclast activity in a subject, said method comprising administering to the subject a polypeptide with SEQ ID NO: 12 in an amount from about 0.1 mg/kg to about 0.3 mg/kg every four months, wherein NTX-1 levels in urine are reduced by at least 45%, compared to pre-treatment or normal levels, and maintained (throughout the treatment period) at at least 45%. The invention thus also relates to a polypeptide with SEQ ID NO: 12 for inhibiting bone resorption and/or osteoclast activity, wherein the polypeptide is administered in an amount from about 0.1 mg/kg to about 0.3 mg/kg every four months and wherein NTX-1 levels in urine are reduced by at least 45%, compared to pre-treatment or normal levels, and maintained (throughout the treatment period) at at least 45%.

In another aspect, the invention relates to a method for inhibiting bone resorption and/or osteoclast activity in a subject, said method comprising administering to the subject a polypeptide with SEQ ID NO: 12 in an amount from about 1 mg/kg to about 3 mg/kg every four months, wherein NTX-1 levels in urine are reduced by at least 70%, compared to pre-treatment or normal levels, and maintained (throughout the treatment period) at at least 70%. The invention thus also relates to a polypeptide with SED ID NO: 12 for inhibiting bone resorption and/or osteoclast activity, wherein the polypeptide is administered in an amount from about 1 mg/kg to about 3 mg/kg every four months and wherein NTX-1 levels in urine are reduced by at least 70%, compared to pre-treatment or normal levels, and maintained (throughout the treatment period) at at least 70%.

DETAILED DESCRIPTION OF THE INVENTION

Methods of the Invention

The Applicant has discovered that the administration to human subjects of polypeptides as described herein that specifically bind RANKL provides an unexpectly sustained, prolonged effect on bone resorption and/or osteoclast activity in the human subjects as observed through changes in relevant biomarkers (such as CTX-1, NTX-1, TRACP5b and P1NP). Therefore, the invention relates to the use of the polypeptides described herein to inhibit bone resorption and/or osteoclast activity in a subject for unexpectedly prolonged periods of time, particularly in view of the doses administered. The invention also provides for less frequent and/or lower dose administration to a subject of the polypeptides described herein, while still maintaining effective inhibition of bone resorption and/or osteoclast activity in the subject at unexpectedly prolonged periods of time, particularly in view of the doses administered.

Various markers are available for measuring bone metabolism. In a preferred aspect, markers of bone metabolism are selected from C-terminal telopeptide of type I collagen (also referred to as cross-linking telopeptide of type I collagen) (CTX-1), N-terminal telopeptide of type I collagen (NTX-1) and/or, preferably, the ratio of NTX-1/creatinine (such as in urine), tartrate-resistant acid phosphatase isoform 5b (TRACP5b), N-terminal propeptide of type I procollagen (P1NP) and bone-specific alkaline phosphatase (BAP). These markers can be measured using standard methods known to and used by the skilled person, such as various immunologically based assays, including enzyme-linked immunosorbent assays (ELISA; also known as an enzyme immunoassay (EIA)), radioimmunoassays or immunoenzymetric assays. Chemical, colorimetric and enzymatic based assays also may be used when suitable.

For example, in some embodiments, one or more of CTX-1, NTX-1 and TRACP5b can be measured using an ELISA assay specific for CTX-1, NTX-1, or TRACP5b; P1NP can be measured using a radioimmunoassay specific for P1NP; BAP can be measured using an immunoenzymetric assay specific for BAP; and/or creatinine can be measured using a colorimetric assay (such as an improved Jaffe assay).

Cross-linking telopeptide of type 1 collagen (CTX-1) is a bone degradation product released as a result from osteoclast activity. A dose resulting in a clinically significant reduction, i.e. below 70% of baseline (i.e. more than 30% reduction compared to pre-treatment or normal levels), of CTX-1 is considered biologically active. This is based on a least significant change derived from data published by Christgau et al. 2000, Bone 26: 505-511). A dose resulting in this clinically significant reduction of the CTX-1 was considered biologically active.

Serum levels of CTX-1 can be determined by any method as described herein and/or known in the art. ELISA methods may include the C-telopeptide of type 1 collagen (CTX-1) ELISA kit (Biocomare; South San Francisco, Calif., USA), C-Telopeptide of Type I Collagen ELISA Kit (antibodies on line.com) and the CROSSLAPS® ELISA (Cat. No. AC-02F1; Immunodiagnosticsystems Inc., Boldon, Tyne & Wear, UK).

N-terminal telopeptide of type 1 collagen (NTX-1) is a degradation product of type I collagen, which is the organic major component of the extracellular matrix. Therefore NTX-1 is considered as a biomarker for bone resorption as a result of osteoclast activity. Since NTX-1 concentration in urine varies with urine volume, the ratio of NTX-1 to creatinine in urine was determined instead of the urine concentration of NTX-1, to correct for this variation. Urine levels of NTX-1 can be determined by any method as described herein and/or known in the art. ELISA methods may include the ELISA Kit for Cross Linked N-Telopeptide Of Type I Collagen (NTXI) (Biocomare; South San Francisco, Calif., USA) and the OSTEOMARK NTx Urine ELISA (Cat no. 9006; Inverness Medical, Wampole Laboratories, Princteon, N.J., USA). The test uses a monoclonal antibody and ELISA method with readout by spectrometry. Creatine levels can be determined e.g. with the EnzyChrom™ Creatine Assay Kit (BioAssay Systems, Hayward, Calif., USA), the Creatinine Assay Kit (Cell Biolabs, San Diego, Calif., USA) or the creatinine test (Cat. No. 03039070; Siemens Medical Solutions Diagnostics, Breda, Netherlands). Urine NTx levels are normalized with respect to urine creatinine. ELISA results are expressed in nM of bone collagen equivalents (nM BCE) per mM of creatinine.

Tartrate-resistant acid phosphatase (TRACP5b) is an enzyme derived from osteoclasts and is a measure for osteoclast numbers, and therefore considered as a biomarker for bone resorption. Serum levels of TRACP5b can be determined by any method as described herein and/or known in the art. ELISA methods may include the Human TartRate Resistant ACID Phosphatase 5b Elisa Kit (Life Sciences Advanced Technologies, Inc., St. Petersburg, Fla., USA), the Tartrate-resistant acid phosphatase-5b (Pacific Biomarkers, Inc. Seattle, Wash., USA), and the BONETRAP® Assay ELISA (Cat. no. SB-TR201A; Immunodiagnostic Systems Inc., Boldon, Tyne & Wear, UK).

Procollagen type 1 amino-terminal propeptide (P1NP) is released upon extracellular processing from newly synthesized pre procollagen prior to the incorporation of collagen into the bone and is considered as a biomarker for bone formation. Serum levels of P1NP can be determined by any method as described herein and/or known in the art. Assay methods may include the competitive RIA (UNIQ™ P1NP RIA; Cat. no. Q67034; Orion Diagnostica Oy, Espoo, Finland), the IDS-iSYS Intact amino-terminal propeptide of type I procollagen (Intact PINP) assay (Immunodiagnostic Systems Inc., Boldon, Tyne & Wear, UK), or the ELISA Kit for Procollagen I N-Terminal Propeptide (PINP) (Uscn Life Science Inc. Wuhan, China).

Bone specific alkaline phosphatase (BAP) is an enzyme that serves as a biomarker for active bone formation. Serum levels of BAP can be determined by any method as described herein and/or known in the art. Assay methods may include the Bone-specific alkaline phosphatase ELISA kit (antibodies-online Inc. Atlanta, Ga., USA), or the OSTASE® BAP Immunoenzymetric Assay (Cat. no. AC-20F1; Immunodiagnostic Systems Inc., Boldon, Tyne & Wear, UK).

Exemplary methods for inhibiting bone resorption or osteoclast activity in a subject include administering to the subject a polypeptide as described herein that specifically binds RANKL, wherein the amount of the polypeptide administered is effective to change one or more markers of bone metabolism and/or bone homeostasis, such as to reduce serum levels of cross-linking telopeptide of type I collagen (CTX-1), serum levels of procollagen type 1 amino-terminal propeptide (P1NP) and/or urine levels of NTX-1, by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration. Accordingly, the invention also relates to a polypeptide of the invention for inhibiting RANK-L mediated bone resorption and/or osteoclast activity, wherein the amount of the polypeptide administered is effective to reduce serum levels of CTX-1, and/or P1NP and/or levels of NTX-1 (as determined by the ratio if NTX-1 to creatine in urine) by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration. For example, the amount of the polypeptide administered is effective to change one or more markers of bone metabolism and/or bone homeostasis, such as to reduce serum level of CTX-1 and/or P1NP, and/or urine levels of NTX-1 by at least 30%, 31%, 32%, 33%, 34%, 35%, 36%, 37%, 38%, 39%, 40%, 41%, 42%, 43%, 44%, 45%, 46%, 47%, 48%, 59%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%.

In another aspect, the amount of the polypeptide administered is effective as to reduce serum level of tartrate-resistant acid phosphatase (TRACP5b) by at least 30%, more preferably at least 35%, more preferably at least 40%, more preferably at least 45%, more preferably at least 50%, such as least 55%, or at least 60%, compared to pre-treatment or normal levels, for at least about 30 days after administration. Accordingly, the invention also relates to a polypeptide of the invention for inhibiting RANK-L mediated bone resorption and/or osteoclast activity, wherein the amount of the polypeptide administered is effective to reduce serum levels of TRACP5b by at least 30%, more preferably at least 35%, more preferably at least 40%, more preferably at least 45%, more preferably at least 50%, such as at least 55%, or at least 60%, compared to pre-treatment or normal levels, for at least about 30 days after administration. For example, the amount of the polypeptide administered is effective to change TRACP5b by at least 30%, 31%, 32%, 33%, 34%, 35%, 36%, 37%, 38%, 39%, 40%, 41%, 42%, 43%, 44%, 45%, 46%, 47%, 48%, 59%, 50%, 51%, 52%, 53%, 54%, 55%, 56%, 57%, 58%, 59% or 60%.

In some embodiments, methods for inhibiting bone resorption or osteoclast activity in a subject are provided that include administering to the subject a polypeptide that specifically binds Receptor Activator of Nuclear Factor kappa B Ligand (RANKL), wherein the amount of the polypeptide administered is effective to change one or more markers of bone metabolism and/or bone homeostasis for at least 30 days after administration. Accordingly, the invention also relates to a polypeptide of the invention for inhibiting RANK-L mediated bone resorption and/or osteoclast activity, wherein the amount of the polypeptide administered is effective to change one or more markers of bone metabolism and/or bone homeostatis for at least 30 days. The change in the one or more markers of bone metabolism and/or bone homeostasis can persist for longer periods of time, such as at least 60 days, at least 90 days, at least 120 days, at least 150 days, at least 180 days, at least 210 days, at least 240 days, at least 270 days, at least 300 days, at least 330 days, or at least 360 days; for example (including the ends of each range) 30-60 days, 60-90 days, 90-120 days, 120-150 days, 150-180 days, 180-210 days, 210-240 days, 240-270 days, 270-300 days, 300-330 days, 330-360 days, 30-90 days, 60-120 days, 90-150 days, 120-180 days, 150-210 days, 180-240 days, 210-270 days, 240-300 days, 300-360 days, 30-120 days, 60-150 days, 90-180 days, 120-210 days, 150-240 days, 180-270 days, 210-300 days, 240-330 days, 270-360 days, 30-150 days, 60-180 days, 90-210 days, 120-240 days, 150-270 days, 180-300 days, 210-330 days, 240-360 days, 30-180 days, 60-210 days, 90-240 days, 120-270 days, 150-300 days, 180-330 days, 210-360 days, 30-210 days, 60-240 days, 90-270 days, 120-300 days, 150-330 days, 180-360 days, 30-240 days, 60-270 days, 90-300 days, 120-330 days, 150-360 days, 30-270 days, 60-300 days, 90-330 days, 120-360 days, 30-300 days, 60-330 days, 90-360 days, 30-330 days, 60-360 days, and 30-360 days; or for at least 1, 2, 3, 4, 5, 6, 7, 8, 9, 10, 11 or 12 months; for example 30 days-3 months, 1-3 months, 2-4 months, 3-5 months, 4-6 months, 5-7 months, 6-8 months, 7-9 months, 8-10 months, 9-11 months, 10-12 months, 1-4 months, 2-5 months, 3-6 months, 4-7 months, 5-8 months, 6-9 months, 7-10 months, 8-11 months, 9-12 months, 1-5 months, 2-6 months, 3-7 months, 4-8 months, 5-9 months, 6-10 months, 7-11 months, 8-12 months, 1-6 months, 2-7 months, 3-8 months, 4-9 months, 5-10 months, 6-11 months, 7-12 months, 1-7 months, 2-8 months, 3-9 months, 4-10 months, 5-11 months, 6-12 months, 1-8 months, 2-9 months, 3-10 months, 4-11 months, 5-12 months, 1-9 months, 2-10 months, 3-11 months, 4-12 months, 1-10 months, 2-11 months, 3-12 months, 1-11 months, 2-12 months, or 1-12 months.

In other embodiments, methods for inhibiting bone resorption or osteoclast activity in a subject are provided that include administering to the subject a polypeptide that specifically binds Receptor Activator of Nuclear Factor kappa B Ligand (RANKL), wherein the amount of the polypeptide administered is effective to reduce serum level of cross-linking telopeptide of type I collagen (CTX-1) for at least about 30 days after administration. Accordingly, the invention also relates to a polypeptide of the invention for inhibiting RANK-L mediated bone resorption and/or osteoclast activity, wherein the amount of the polypeptide administered is effective to reduce serum level of CTX-1 for at least about 30 days after administration. In some embodiments, the serum level of CTX-1 is reduced, compared to pre-treatment or normal levels, by 30%-80% or more, such as by at least 30%, 31%, 32%, 33%, 34%, 35%, 36%, 37%, 38%, 39%, 40%, 41%, 42%, 43%, 44%, 45%, 46%, 47, 48, 59, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80%. The reduction in the serum level of CTX-1 can persist for longer periods of time, such as at least 60 days, at least 90 days, at least 120 days, at least 150 days, at least 180 days, at least 210 days, at least 240 days, at least 270 days, at least 300 days, at least 330 days, or at least 360 days; for example (including the ends of each range) 30-60 days, 60-90 days, 90-120 days, 120-150 days, 150-180 days, 180-210 days, 210-240 days, 240-270 days, 270-300 days, 300-330 days, 330-360 days, 30-90 days, 60-120 days, 90-150 days, 120-180 days, 150-210 days, 180-240 days, 210-270 days, 240-300 days, 270-330 days, 300-360 days, 30-120 days, 60-150 days, 90-180 days, 120-210 days, 150-240 days, 180-270 days, 210-300 days, 240-330 days, 270-360 days, 30-150 days, 60-180 days, 90-210 days, 120-240 days, 150-270 days, 180-300 days, 210-330 days, 240-360 days, 30-180 days, 60-210 days, 90-240 days, 120-270 days, 150-300 days, 180-330 days, 210-360 days, 30-210 days, 60-240 days, 90-270 days, 120-300 days, 150-330 days, 180-360 days, 30-240 days, 60-270 days, 90-300 days, 120-330 days, 150-360 days, 30-270 days, 60-300 days, 90-330 days, 120-360 days, 30-300 days, 60-330 days, 90-360 days, 30-330 days, 60-360 days, and 30-360 days; or for at least 1, 2, 3, 4, 5, 6, 7, 8, 9, 10, 11 or 12 months; for example 30 days-3 months, 1-3 months, 2-4 months, 3-5 months, 4-6 months, 5-7 months, 6-8 months, 7-9 months, 8-10 months, 9-11 months, 10-12 months, 1-4 months, 2-5 months, 3-6 months, 4-7 months, 5-8 months, 6-9 months, 7-10 months, 8-11 months, 9-12 months, 1-5 months, 2-6 months, 3-7 months, 4-8 months, 5-9 months, 6-10 months, 7-11 months, 8-12 months, 1-6 months, 2-7 months, 3-8 months, 4-9 months, 5-10 months, 6-11 months, 7-12 months, 1-7 months, 2-8 months, 3-9 months, 4-10 months, 5-11 months, 6-12 months, 1-8 months, 2-9 months, 3-10 months, 4-11 months, 5-12 months, 1-9 months, 2-10 months, 3-11 months, 4-12 months, 1-10 months, 2-11 months, 3-12 months, 1-11 months, 2-12 months, or 1-12 months.

In certain embodiments, CTX-1 is reduced by at least 30%, compared to pre-treatment or normal levels, for up to 30, 60, 90, 120, 150, 180, 210, 240, 270 or 280 days after administration.

In certain embodiments, CTX-1 is reduced by at least 40%, compared to pre-treatment or normal levels, for up to 30, 60, 90, 120, 150, 180, 210, 240 or 270 days after administration.

In certain embodiments, CTX-1 is reduced by at least 45%, compared to pre-treatment or normal levels, for up to 30, 60, 90, 120, 150, 180, or 190 days after administration.

In certain embodiments, CTX-1 is reduced by at least 50%, compared to pre-treatment or normal levels, for up to 30, 60, 90, 120, 150 or 180 days after administration.

In certain embodiments, CTX-1 is reduced by at least 60%, compared to pre-treatment or normal levels, for up to 30, 60, 90, 120 or 150 days after administration.

In certain embodiments, CTX-1 is reduced by at least 70%, compared to pre-treatment or normal levels, for up to 30, 60, 90 or 120 days after administration.

In certain embodiments, CTX-1 is reduced by at least 80%, compared to pre-treatment or normal levels, for up to 30, 60 or 90 days after administration.

In other embodiments, methods for inhibiting bone resorption or osteoclast activity in a subject are provided that include administering to the subject a polypeptide that specifically binds Receptor Activator of Nuclear Factor kappa B Ligand (RANKL), wherein the amount of the polypeptide administered is effective to reduce the level of N-terminal telopeptide of type I collagen (NTX-1) for at least about 30 days after administration. Accordingly, the invention also relates to a polypeptide of the invention for inhibiting RANK-L mediated bone resorption and/or osteoclast activity, wherein the amount of the polypeptide administered is effective to reduce the urine level of NTX-1 for at least about 30 days after administration. In some embodiments, the level of NTX-1 is reduced, compared to pre-treatment or normal levels, by 30%-80% or more, such as by at least 30%, 31%, 32%, 33%, 34%, 35%, 36%, 37%, 38%, 39%, 40%, 41%, 42%, 43%, 44%, 45%, 46%, 47, 48, 59, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80%. The reduction in the level of NTX-1 can persist for longer periods of time, such as at least 60 days, at least 90 days, at least 120 days, at least 150 days, at least 180 days, at least 210 days, at least 240 days, at least 270 days, at least 300 days, at least 330 days, or at least 360 days; for example (including the ends of each range) 30-60 days, 60-90 days, 90-120 days, 120-150 days, 150-180 days, 180-210 days, 210-240 days, 240-270 days, 270-300 days, 300-330 days, 330-360 days, 30-90 days, 60-120 days, 90-150 days, 120-180 days, 150-210 days, 180-240 days, 210-270 days, 240-300 days, 270-330 days, 300-360 days, 30-120 days, 60-150 days, 90-180 days, 120-210 days, 150-240 days, 180-270 days, 210-300 days, 240-330 days, 270-360 days, 30-150 days, 60-180 days, 90-210 days, 120-240 days, 150-270 days, 180-300 days, 210-330 days, 240-360 days, 30-180 days, 60-210 days, 90-240 days, 120-270 days, 150-300 days, 180-330 days, 210-360 days, 30-210 days, 60-240 days, 90-270 days, 120-300 days, 150-330 days, 180-360 days, 30-240 days, 60-270 days, 90-300 days, 120-330 days, 150-360 days, 30-270 days, 60-300 days, 90-330 days, 120-360 days, 30-300 days, 60-330 days, 90-360 days, 30-330 days, 60-360 days, and 30-360 days; or for at least 1, 2, 3, 4, 5, 6, 7, 8, 9, 10, 11 or 12 months; for example 30 days-3 months, 1-3 months, 2-4 months, 3-5 months, 4-6 months, 5-7 months, 6-8 months, 7-9 months, 8-10 months, 9-11 months, 10-12 months, 1-4 months, 2-5 months, 3-6 months, 4-7 months, 5-8 months, 6-9 months, 7-10 months, 8-11 months, 9-12 months, 1-5 months, 2-6 months, 3-7 months, 4-8 months, 5-9 months, 6-10 months, 7-11 months, 8-12 months, 1-6 months, 2-7 months, 3-8 months, 4-9 months, 5-10 months, 6-11 months, 7-12 months, 1-7 months, 2-8 months, 3-9 months, 4-10 months, 5-11 months, 6-12 months, 1-8 months, 2-9 months, 3-10 months, 4-11 months, 5-12 months, 1-9 months, 2-10 months, 3-11 months, 4-12 months, 1-10 months, 2-11 months, 3-12 months, 1-11 months, 2-12 months, or 1-12 months.

In certain embodiments, NTX-1 is reduced by at least 30%, compared to pre-treatment or normal levels, for up to 30, 60, 90, 120, 150, 180, 210, 240, 270, 300, 330 or 360 days after administration.

In certain embodiments, NTX-1 is reduced by at least 40%, compared to pre-treatment or normal levels, for up to 30, 60, 90, 120, 150, 180, 210, 240, 270, 300, 330 or 360 days after administration.

In certain embodiments, NTX-1 is reduced by at least 45%, compared to pre-treatment or normal levels, for up to 30, 60, 90, 120, 150, 180, 210, 240 or 250 days after administration.

In certain embodiments, NTX-1 is reduced by at least 50%, compared to pre-treatment or normal levels, for up to 30, 60, 90, 120, 150, 180, 210 or 240 days after administration.

In certain embodiments, NTX-1 is reduced by at least 60%, compared to pre-treatment or normal levels, for up to 30, 60, 90, 120, 150, 180 or 210 days after administration.

In certain embodiments, NTX-1 is reduced by at least 70%, compared to pre-treatment or normal levels, for up to 30, 60, 90, 150 or 180 days after administration.

In certain embodiments, NTX-1 is reduced by at least 80%, compared to pre-treatment or normal levels, for up to 30, 60 or 90 days after administration.

In other embodiments, methods for inhibiting bone resorption or osteoclast activity in a subject are provided that include administering to the subject a polypeptide that specifically binds Receptor Activator of Nuclear Factor kappa B Ligand (RANKL), wherein the amount of the polypeptide administered is effective to reduce serum level of tartrate-resistant acid phosphatase (TRACP5b) for at least about 30 days after administration. Accordingly, the invention also relates to a polypeptide of the invention for inhibiting RANK-L mediated bone resorption and/or osteoclast activity, wherein the amount of the polypeptide administered is effective to reduce serum level of TRACP5b for at least about 30 days after administration. In some embodiments, the serum level of TRACP5b is reduced, compared to pre-treatment or normal levels, by 30%-80% or more, such as by at least 30%, 31%, 32%, 33%, 34%, 35%, 36%, 37%, 38%, 39%, 40%, 41%, 42%, 43%, 44%, 45%, 46%, 47, 48, 59, 50, 51, 52, 53, 54, 55, 56, 57, 58, 59 or 60%. The reduction in the serum level of TRACP5b can persist for longer periods of time, such as at least 60 days, at least 90 days, at least 120 days, at least 150 days, at least 180 days, at least 210 days; for example (including the ends of each range) 30-60 days, 60-90 days, 90-120 days, 120-150 days, 150-180 days, 180-210 days, 30-90 days, 60-120 days, 90-150 days, 120-180 days, 30-120 days, 60-150 days, 90-180 days, 120-210 days, 30-150 days, 60-180 days, 90-210 days, 30-180 days, 60-210 days, 30-210 days; or for at least 1, 2, 3, 4, 5, 6, 7, 8, 9, 10, 11 or 12 months; for example 30 days-3 months, 1-3 months, 2-4 months, 3-5 months, 4-6 months, 5-7 months, 1-4 months, 2-5 months, 3-6 months, 4-7 months, 1-5 months, 2-6 months, 3-7 months, 1-6 months, 2-7 months or 1-7 months.

In certain embodiments, TRACP5b is reduced by at least 30%, compared to pre-treatment or normal levels, for up to 30, 60, 90, 120, 150, 180, 210 days after administration.

In certain embodiments, TRACP5b is reduced by at least 40%, compared to pre-treatment or normal levels, for up to 30, 60, 90, 120, 150 days after administration.

In certain embodiments, TRACP5b is reduced by at least 45%, compared to pre-treatment or normal levels, for up to 30, 60, 90, 120, 150 days after administration.

In certain embodiments, TRACP5b is reduced by at least 50%, compared to pre-treatment or normal levels, for up to 30, 60 days after administration.

In certain embodiments, TRACP5b is reduced by at least 60%, compared to pre-treatment or normal levels, for up to 30 days after administration.

In other embodiments, methods for inhibiting bone resorption or osteoclast activity in a subject are provided that include administering to the subject a polypeptide that specifically binds Receptor Activator of Nuclear Factor kappa B Ligand (RANKL), wherein the amount of the polypeptide administered is effective to reduce serum level of procollagen type 1 amino-terminal propeptide (P1NP) for at least about 30 days after administration. Accordingly, the invention also relates to a polypeptide of the invention for inhibiting RANK-L mediated bone resorption and/or osteoclast activity, wherein the amount of the polypeptide administered is effective to reduce serum level of P1NP for at least about 30 days after administration. In some embodiments, the serum level of P1NP is reduced, compared to pre-treatment or normal levels, by 30%-80% or more, such as by at least 30%, 31%, 32%, 33%, 34%, 35%, 36%, 37%, 38%, 39%, 40%, 41%, 42%, 43%, 44%, 45%, 46%, 47, 48, 59, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80%. The reduction in the serum level of P1NP can persist for longer periods of time, such as at least 60 days, at least 90 days, at least 120 days, at least 150 days, at least 180 days, at least 210 days, at least 240 days, at least 270 days, at least 300 days, at least 330 days, or at least 360 days; for example (including the ends of each range) 30-60 days, 60-90 days, 90-120 days, 120-150 days, 150-180 days, 180-210 days, 210-240 days, 240-270 days, 270-300 days, 300-330 days, 330-360 days, 30-90 days, 60-120 days, 90-150 days, 120-180 days, 150-210 days, 180-240 days, 201-270 days, 240-300 days, 270-330 days, 300-360 days, 30-120 days, 60-150 days, 90-180 days, 120-210 days, 150-240 days, 180-270 days, 210-300 days, 240-330 days, 270-360 days, 30-150 days, 60-180 days, 90-210 days, 120-240 days, 150-270 days, 180-300 days, 210-330 days, 240-360 days, 30-180 days, 60-210 days, 90-240 days, 120-270 days, 150-300 days, 180-330 days, 210-360 days, 30-210 days, 60-240 days, 90-270 days, 120-300 days, 150-330 days, 180-360 days, 30-240 days, 60-270 days, 90-300 days, 120-330 days, 150-360 days, 30-270 days, 60-300 days, 90-330 days, 120-360 days, 30-300 days, 60-330 days, 90-360 days, 30-330 days, 60-360 days, and 30-360 days; or for at least 1, 2, 3, 4, 5, 6, 7, 8, 9, 10, 11 or 12 months; for example 30 days-3 months, 1-3 months, 2-4 months, 3-5 months, 4-6 months, 5-7 months, 6-8 months, 7-9 months, 8-10 months, 9-11 months, 10-12 months, 1-4 months, 2-5 months, 3-6 months, 4-7 months, 5-8 months, 6-9 months, 7-10 months, 8-11 months, 9-12 months, 1-5 months, 2-6 months, 3-7 months, 4-8 months, 5-9 months, 6-10 months, 7-11 months, 8-12 months, 1-6 months, 2-7 months, 3-8 months, 4-9 months, 5-10 months, 6-11 months, 7-12 months, 1-7 months, 2-8 months, 3-9 months, 4-10 months, 5-11 months, 6-12 months, 1-8 months, 2-9 months, 3-10 months, 4-11 months, 5-11 months, 1-9 months, 2-10 months, 3-11 months, 4-12 months, 1-10 months, 2-11 months, 3-12 months, 1-11 months, 2-12 months, or 1-12 months.

In certain embodiments, P1NP is reduced by at least 30%, compared to pre-treatment or normal levels, for up to 30, 60, 90, 120, 150, 180, 210, 240, 270 or 300 days after administration.

In certain embodiments, P1NP is reduced by at least 40%, compared to pre-treatment or normal levels, for up to 30, 60, 90, 120, 150, 180, 210, 240 or 270 days after administration.

In certain embodiments, P1NP is reduced by at least 45%, compared to pre-treatment or normal levels, for up to 30, 60, 90, 120, 150, 180, or 210 days after administration.

In certain embodiments, P1NP is reduced by at least 50%, compared to pre-treatment or normal levels, for up to 30, 60, 90, 120, 150, 180 or 210 days after administration.

In certain embodiments, P1NP is reduced by at least 60%, compared to pre-treatment or normal levels, for up to 30, 60, 90, 120, 150, 180 or 210 days after administration.

In certain embodiments, P1NP is reduced by at least 70%, compared to pre-treatment or normal levels, for up to 30, 60, 90, 120, 150 or 180 days after administration.

In certain embodiments, P1NP is reduced by at least 80%, compared to pre-treatment or normal levels, for up to 30, 60, 90 or 120 days after administration.

In some of the embodiments, the reduction in CTX-1 and/or NTX-1 is achieved by 8 hours after administration of the polypeptide, such as by 9, 10, 11, 12, 13, 14, 15, 16, 17, 18, 19, 20, 21, 22, 23 or 24 hours after administration of the polypeptide.

In some of the embodiments, the reduction in TRACP5b is achieved by 2 days after administration of the polypeptide, such as by 3, 4 or 5 days after administration of the polypeptide.

In some embodiments, to obtain the unexpected prolonged and sustained effects described herein, the polypeptide that specifically binds RANKL is administered in an amount from about 0.001 mg/kg to about 10 mg/kg. In some embodiments, dose ranges (inclusive of the values at the ends of each range) include 0.003-10 mg/kg, such as 0.003-3 mg/kg, 0.003-1 mg/kg, 0.003-0.3 mg/kg, 0.003-0.1 mg/kg, 0.003-0.03 mg/kg, 0.003-0.01 mg/kg, 0.01-10 mg/kg, 0.01-3 mg/kg, 0.01-1 mg/kg, 0.01-0.3 mg/kg, 0.01-0.1 mg/kg, 0.01-0.03 mg/kg, 0.03-10 mg/kg, 0.03-3 mg/kg, 0.03-1 mg/kg, 0.03-0.3 mg/kg, 0.03-0.1 mg/kg, 0.1-10 mg/kg, 0.1-3 mg/kg, 0.1-1 mg/kg, 0.1-0.3 mg/kg, 0.3-10 mg/kg, 0.3-3 mg/kg, 0.3-1 mg/kg, 1-10 mg/kg, 1-3 mg/kg, and 3-10 mg/kg. In some embodiments, specific doses include 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10 mg/kg.

The desired dose may conveniently be presented in a single dose or as divided doses administered at appropriate intervals, for example, as monthly doses, e.g. monthly dose (Q1M), two monthly dose (Q2M), three monthly dose (Q3M) or four monthly dose (Q4M), etc.

In a preferred aspect, the polypeptide of the invention is administered in an amount from about 0.003 mg/kg to about 0.03 mg/kg every month.

In another preferred aspect, the polypeptide of the invention is administered in an amount from about 0.01 mg/kg to about 0.1 mg/kg every two months.

In another preferred aspect, the polypeptide of the invention is administered in an amount from about 0.01 mg/kg to about 0.1 mg/kg every three months.

In another preferred aspect, the polypeptide of the invention is administered in an amount from about 0.01 mg/kg to about 0.1 mg/kg every three months.

Preferably the polypeptide of the invention is SEQ ID NO: 12.

Methods are provided for inhibiting bone resorption and/or osteoclast activity in a subject that include administering to the subject a polypeptide of the invention in an amount of about 0.003 mg/kg, wherein CTX-1 levels in serum are reduced by 30%, compared to pre-treatment or normal levels, and maintained at at least 30% for at least 30 days after administration.

In another specific aspect, a polypeptide of the invention is administered in an amount of about 0.01 mg/kg to 0.03 mg/kg, wherein CTX-1 levels in serum are reduced by 30%, compared to pre-treatment or normal levels, and maintained at at least 30% for at least 30 days after administration. In some embodiments, the serum level of CTX-1 is reduced by and maintained at at least 40%, such as at least 45%, at least 50%, more preferably at least 60% or even at least 70% or more, compared to pre-treatment or normal levels. In a specific aspect, the CTX-1 levels in serum are reduced by 30%, compared to pre-treatment or normal levels, and maintained at at least 30% for up to at least 60 days, at least 90 days, or at least 120 days after administration. In another specific aspect, the CTX-1 levels in serum are reduced by 45%, compared to pre-treatment or normal levels, and maintained at at least 45% for up to at least 60 days after administration.

In another specific aspect, a polypeptide of the invention is administered in an amount of about 0.1 mg/kg to 1 mg/kg or more, wherein CTX-1 levels in serum are reduced by 30%, compared to pre-treatment or normal levels, and maintained at at least 30% for at least 30 days after administration. In some embodiments, the serum level of CTX-1 is reduced by and maintained at at least 40%, such as at least 45%, at least 50%, more preferably at least 60%, at least 70% or even at least 80% or more, compared to pre-treatment or normal levels. In a specific aspect, the CTX-1 levels in serum are reduced by 30%, compared to pre-treatment or normal levels, and maintained at at least 30% for up to at least 60 days, at least 90 days, at least 120 days, at least 150 days, at least 210 days, or even at least 270 days after administration. In another specific aspect, the CTX-1 levels in serum are reduced by 45%, compared to pre-treatment or normal levels, and maintained at at least 45% for up to at least 60 days, at least 90 days, at least 120 days, or even at least 150 days after administration.

Methods are provided for inhibiting bone resorption and/or osteoclast activity in a subject that include administering to the subject a polypeptide of the invention in an amount of about 0.01 mg/kg to 0.03 mg/kg, wherein NTX-1 levels in urine are reduced by 30%, compared to pre-treatment or normal levels, and maintained at at least 30% for at least 30 days after administration. In some embodiments, the level of NTX-1 is reduced by and maintained at at least 40%, such as at least 45%, more preferably at least 50% or even at least 60% or more, compared to pre-treatment or normal levels. In a specific aspect, the NTX-1 levels in urine are reduced by 30%, compared to pre-treatment or normal levels, and maintained at at least 30% for up to at least 60 days, or at least 90 days after administration. In another specific aspect, the NTX-1 levels are reduced by 45%, compared to pre-treatment or normal levels, and maintained at at least 45% for up to at least 60 days after administration.

In another specific aspect, a polypeptide of the invention is administered in an amount of about 0.1 mg/kg to 1 mg/kg or more, wherein NTX-1 levels are reduced by 30%, compared to pre-treatment or normal levels, and maintained at at least 30% for at least 30 days after administration. In some embodiments, the level of NTX-1 is reduced by and maintained at at least 40%, such as at least 45%, at least 50%, more preferably at least 60%, or even at least 70% or more, compared to pre-treatment or normal levels. In a specific aspect, the NTX-1 levels in urine are reduced by 30%, compared to pre-treatment or normal levels, and maintained at at least 30% for up to at least 60 days, at least 90 days, at least 120 days, at least 150 days, at least 210 days, or even at least 270 days after administration. In another specific aspect, the NTX-1 levels in urine are reduced by 45%, compared to pre-treatment or normal levels, and maintained at at least 45% for up to at least 60 days, at least 90 days, at least 120 days, or even at least 150 days after administration.

Methods are provided for inhibiting bone resorption and/or osteoclast activity in a subject that include administering to the subject a polypeptide of the invention in an amount of about 0.003 mg/kg, wherein TRACP5b levels in serum are reduced by 30%, compared to pre-treatment or normal levels, and maintained at at least 30%.

In another specific aspect, a polypeptide of the invention is administered in an amount of about 0.01 mg/kg to 0.03 mg/kg, wherein TRACP5b levels in serum are reduced by 30%, compared to pre-treatment or normal levels, and maintained at at least 30% for at least 30 days after administration. In a specific aspect, the TRACP5b levels in serum are reduced by 30%, compared to pre-treatment or normal levels, and maintained at at least 30% for up to at least 60 days after administration.

In another specific aspect, a polypeptide of the invention is administered in an amount of about 0.1 mg/kg or more, wherein TRACP5b levels in serum are reduced by 30%, compared to pre-treatment or normal levels, and maintained at at least 30% for at least 30 days after administration. In some embodiments, the serum level of TRACP5b is reduced by and maintained at at least 40%, such as at least 45%, compared to pre-treatment or normal levels. In a specific aspect, the TRACP5b levels in serum are reduced by 30%, compared to pre-treatment or normal levels, and maintained at at least 30% for up to at least 60 days, or even at least 90 days after administration.

In another specific aspect, a polypeptide of the invention is administered in an amount of about 0.3 mg/kg to 1 mg/kg or more, wherein TRACP5b levels in serum are reduced by 30%, compared to pre-treatment or normal levels, and maintained at at least 30% for at least 30 days after administration. In some embodiments, the serum level of TRACP5b is reduced by and maintained at at least 40%, such as at least 45%, at least 50%, or even at least 60% or more, compared to pre-treatment or normal levels. In a specific aspect, the TRACP5b levels in serum are reduced by 30%, compared to pre-treatment or normal levels, and maintained at at least 30% for up to at least 60 days, at least 90 days, or even at least 120 days after administration. In another specific aspect, the TRACP5b levels in serum are reduced by 45%, compared to pre-treatment or normal levels, and maintained at at least 45% for up to at least 60 days, or even at least 90 days after administration.

Methods are provided for inhibiting bone resorption and/or osteoclast activity in a subject that include administering to the subject a polypeptide of the invention in an amount of about 0.003 mg/kg to about 0.01 mg/kg, wherein P1NP levels in serum are reduced by 30%, compared to pre-treatment or normal levels, and maintained at at least 30% for at least 30 days after administration. In some embodiments, the serum level of P1NP is reduced by and maintained at at least 40%, compared to pre-treatment or normal levels. In a specific aspect, the P1NP levels in serum are reduced by 30%, compared to pre-treatment or normal levels, and maintained at at least 30% for up to at least 60 days, or even at least 90 days, after administration.

In another specific aspect, a polypeptide of the invention is administered in an amount of about 0.03 mg/kg, wherein P1NP levels in serum are reduced by 30%, compared to pre-treatment or normal levels, and maintained at at least 30% for at least 30 days after administration. In some embodiments, the serum level of P1NP is reduced by and maintained at at least 40%, such as at least 45%, or more, compared to pre-treatment or normal levels. In a specific aspect, the P1NP levels in serum are reduced by 30%, compared to pre-treatment or normal levels, and maintained at at least 30% for up to at least 60 days, at least 90 days, at least 120 days, or even at least 150 days after administration. In another specific aspect, the P1NP levels in serum are reduced by 45%, compared to pre-treatment or normal levels, and maintained at at least 45% for up to at least 60 days, or even at least 90 days after administration.

In another specific aspect, a polypeptide of the invention is administered in an amount of about 0.1 mg/kg to 1 mg/kg or more, wherein P1NP levels in serum are reduced by 30%, compared to pre-treatment or normal levels, and maintained at at least 30% for at least 30 days after administration. In some embodiments, the serum level of P1NP is reduced by and maintained at at least 40%, such as at least 45%, at least 50%, more preferably at least 60%, at least 70% or even at least 80% or more, compared to pre-treatment or normal levels. In a specific aspect, the P1NP levels in serum are reduced by 30%, compared to pre-treatment or normal levels, and maintained at at least 30% for up to at least 60 days, at least 90 days, at least 120 days, at least 150 days, at least 210 days, or even at least 270 days after administration. In another specific aspect, the P1NP levels in serum are reduced by 45%, compared to pre-treatment or normal levels, and maintained at at least 45% for up to at least 60 days, at least 90 days, at least 120 days, or even at least 150 days after administration.

In a preferred aspect, the polypeptide of the invention is SEQ ID NO: 12.

Polypeptide of the Invention
Immunoglobulin Single Variable Domain

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acids or nucleotide sequences encoding the same, unless the context requires a more limited interpretation.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation. In contrast, the binding site of an immunoglobulin single variable domain is formed by a single VH or VL domain. Hence, the antigen binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

Generally, single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such single variable domains and fragments are most preferably such that they comprise an immunoglobulin fold or are capable of forming, under suitable conditions, an immunoglobulin fold. As such, the single variable domain may for example comprise a light chain variable domain sequence (e.g. a VL-sequence) or a suitable fragment thereof; or a heavy chain variable domain sequence (e.g. a VH-sequence or VHH sequence) or a suitable fragment thereof; as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a VH/VL interaction—to form a functional antigen binding domain).

In one embodiment of the invention, the immunoglobulin single variable domains are light chain variable domain sequences (e.g. a VL-sequence), or heavy chain variable domain sequences (e.g. a VH-sequence); more specifically, the immunoglobulin single variable domains can be heavy chain variable domain sequences that are derived from a conventional four-chain antibody or heavy chain variable domain sequences that are derived from a heavy chain antibody.

For example, the single variable domain or immunoglobulin single variable domain (or an amino acid sequence that is suitable for use as an immunoglobulin single variable domain) may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH sequence); other single variable domains, or any suitable fragment of any one thereof. For a general description of (single) domain antibodies, reference is also made to the prior art cited herein, as well as to EP 0368684. For the term "dAb's", reference is for example made to Ward et al. (1989, Nature 341 (6242): 544-6), to Holt et al. (2003, Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, single variable domains can be derived from certain species of shark (for example, the so-called "IgNAR domains", see for example WO 05/18629). In particular, the immunoglobulin single variable domain may be a Nanobody (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020,079 (page 16).

The amino acid sequence and structure of an immunoglobulin sequence, an immunoglobulin single variable domain and, in particular, a Nanobody can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively.

The total number of amino acid residues in an immunoglobulin single variable domain and, in particular, in a Nanobody can be in the region of 110-120, is preferably 112-115, and is most preferably 113. It should however be noted that parts, fragments, analogs or derivatives (as further described herein) of an immunoglobulin single variable domain and, in particular, of a Nanobody are not particularly limited as to their length and/or size, as long as such parts, fragments, analogs or derivatives meet the further requirements outlined herein and are also preferably suitable for the purposes described herein.

For a further description of VHH's and Nanobodies, reference is made to the review article by Muyldermans (2001, Reviews in Molecular Biotechnology 74: 277-302); as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101,985 and WO 08/142,164.

Thus, generally, a Nanobody can be further defined as an amino acid sequence as described in WO 08/142,164 (page 30, line 5 to page 31, line 7 and page 108, line 26 to page 140, line 15).

Thus, in the meaning of the present invention, the term "immunoglobulin single variable domain" or "single variable domain" comprises polypeptides which are derived from a non-human source, preferably a camelid, preferably a camel heavy chain antibody. They may be humanized, as previously described. Moreover, the term comprises polypeptides derived from non-camelid sources, e.g. mouse or human, which have been "camelized", as previously described.

The term "immunoglobulin single variable domain" encompasses immunoglobulin sequences of different origin, comprising mouse, rat, rabbit, donkey, human and camelid immunoglobulin sequences. It also includes fully human, humanized or chimeric immunoglobulin sequences. For example, it comprises camelid immunoglobulin sequences and humanized camelid immunoglobulin sequences, or camelized immunoglobulin single variable domains, e.g. camelized dAb as described by Ward et al (see for example WO 94/04678 and Davies and Riechmann (1994, FEBS 339: 285-290; 1995, Biotechnol. 13: 475-479; 1996, Prot. Eng. 9: 531-537).

However, it should be noted that the invention is not limited as to the origin of the immunoglobulin sequence used in the present invention (or of the nucleotide sequence used to express it), nor as to the way that the immunoglobulin sequence or nucleotide sequence is (or has been) generated or obtained. Thus, the immunoglobulin sequences of the invention may be naturally occurring amino acid sequences (from any suitable species) or synthetic or semi-synthetic amino acid sequences. In a specific but non-limiting aspect of the invention, the immunoglobulin sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized VHH sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences used in the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

Immunoglobulin single variable domains (and polypeptides comprising the same) that are directed against RANKL have been described in US 2010/0104568 and WO 08/142, 164. For example, preferred immunoglobulin single variable domains and/or Nanobodies against RANK-L may consist of 4 framework regions (FR1 to FR4 respectively) and 3 complementarity determining regions (CDR1 to CDR3 respectively), in which:

CDR1 is chosen from the group consisting of:
a) the amino acid sequence of SEQ ID NO: 1 (SEQ ID NO: 200 of US 2010/0104568);
b) amino acid sequences that have at least 80% amino acid identity with the amino acid sequence of SEQ ID NO: 1 (SEQ ID NO: 200 of US 2010/0104568);
c) amino acid sequences that have 3, 2, or 1 amino acid difference with the amino acid sequence of SEQ ID NO: 1 (SEQ ID NO: 200 of US 2010/0104568);
and/or
CDR2 is chosen from the group consisting of:
d) the amino acid sequence of SEQ ID NO 2 (SEQ ID NO: 324 of US 2010/0104568);
e) amino acid sequences that have at least 80% amino acid identity with the amino acid sequence of SEQ ID NO: 2 (SEQ ID NO: 324 of US 2010/0104568);
f) amino acid sequences that have 3, 2, or 1 amino acid difference with the amino acid sequence of SEQ ID NO: 2 (SEQ ID NO's: 324 of US 2010/0104568);
and/or
CDR3 is chosen from the group consisting of:
g) the amino acid sequence of SEQ ID NO: 3 (SEQ ID NO: 448 of US 2010/0104568);
h) amino acid sequences that have at least 80% amino acid identity with the amino acid sequence of SEQ ID NO: 3 (SEQ ID NO: 448 of US 2010/0104568);
i) amino acid sequences that have 3, 2, or 1 amino acid difference with the amino acid sequence of SEQ ID NO: 3 (SEQ ID NO: 448 of US 2010/0104568).

When an immunoglobulin single variable domain and/or Nanobody contains one or more amino acid sequences according to b) and/or c):
i) any amino acid substitution in such an amino acid sequence according to b) and/or c) is preferably, and compared to the corresponding amino acid sequence according to a), a conservative amino acid substitution, (as defined herein);
and/or
ii) the amino acid sequence according to b) and/or c) preferably only contains amino acid substitutions, and no amino acid deletions or insertions, compared to the corresponding amino acid sequence according to a);
and/or
iii) the amino acid sequence according to b) and/or c) may be an amino acid sequence that is derived from an amino acid sequence according to a) by means of affinity maturation using one or more techniques of affinity maturation known per se.

Similarly, when an immunoglobulin single variable domain and/or Nanobody contains one or more amino acid sequences according to e) and/or f):
i) any amino acid substitution in such an amino acid sequence according to e) and/or f) is preferably, and compared to the corresponding amino acid sequence according to d), a conservative amino acid substitution, (as defined herein);
and/or
ii) the amino acid sequence according to e) and/or f) preferably only contains amino acid substitutions, and no amino acid deletions or insertions, compared to the corresponding amino acid sequence according to d);
and/or
iii) the amino acid sequence according to e) and/or f) may be an amino acid sequence that is derived from an amino acid sequence according to d) by means of affinity maturation using one or more techniques of affinity maturation known per se.

Also, similarly, when an immunoglobulin single variable domain and/or Nanobody contains one or more amino acid sequences according to h) and/or i):
i) any amino acid substitution in such an amino acid sequence according to h) and/or i) is preferably, and compared to the corresponding amino acid sequence according to g), a conservative amino acid substitution, (as defined herein);
and/or
ii) the amino acid sequence according to h) and/or i) preferably only contains amino acid substitutions, and no amino acid deletions or insertions, compared to the corresponding amino acid sequence according to g);
and/or
iii) the amino acid sequence according to h) and/or i) may be an amino acid sequence that is derived from an amino acid sequence according to g) by means of affinity maturation using one or more techniques of affinity maturation known per se.

In one preferred, but non-limiting aspect, the immunoglobulin single variable domain and/or Nanobody may essentially consist of 4 framework regions (FR1 to FR4, respectively) and 3 complementarity determining regions (CDR1 to CDR3, respectively), in which the CDR sequences of said immunoglobulin single variable domain and/or Nanobody have at least 70% amino acid identity, preferably at least 80% amino acid identity, more preferably at least 90% amino acid identity, such as 95% amino acid identity or more or even essentially 100% amino acid identity with the CDR sequences of the amino acid sequence of SEQ ID NO: 4 (SEQ ID NO: 572 of US 2010/0104568). This degree of amino acid identity can for example be determined by determining the degree of amino acid identity (in a manner described herein) between said amino acid sequence and SEQ ID NO: 4 (SEQ ID NO: 572 of US 2010/0104568), in which the amino acid residues that form the framework regions are disregarded.

In another preferred, but non-limiting aspect, the CDR sequences have more than 80%, preferably more than 90%, more preferably more than 95%, such as 99% or more sequence identity with SEQ ID NO: 1, SEQ ID NO: 2 and/or SEQ ID NO: 3 (SEQ ID NO: 200, SEQ ID NO: 324 and/or SEQ ID NO:448 of US 2010/0104568).

In particular, such immunoglobulin single variable domain may be such that CDR1 is chosen from SEQ ID NO: 1; and/or CDR2 is chosen from SEQ ID NO: 2; and/or CDR3 is chosen from SEQ ID NO: 3. More preferably, the immunoglobulin single variable domain used in the polypeptide of the invention may essentially consist of 4 framework regions (FR1 to FR4, respectively) and 3 complementarity determining regions (CDR1 to CDR3, respectively), in which:

a) CDR1 is chosen from SEQ ID NO: 1;
b) CDR2 is chosen from SEQ ID NO: 2; and
c) CDR3 is chosen from SEQ ID NO: 3.

Preferred immunoglobulin single variable domains for use in the method of the invention include SEQ ID NO: 4 (SEQ ID NO: 572 of US 2010/0104568) and/or immunoglobulin single variable domains and/or Nanobodies chosen from the group consisting of amino acid sequences that have more than 80%, preferably more than 90%, more preferably more than 95%, such as 99% or more sequence identity with SEQ ID NO: 4.

Humanized immunoglobulin single variable domains and/or Nanobodies may be amino acid sequences that are as generally defined for immunoglobulin single variable domains and/or Nanobodies in the previous paragraphs, but in which at least one amino acid residue is present (and in particular, in at least one of the framework residues) that is and/or that corresponds to a humanizing substitution. Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring VHH sequence with the corresponding framework sequence of one or more closely related human VH sequences, after which one or more of the potentially useful humanizing substitutions (or combinations thereof) thus determined can be introduced into said VHH sequence (in any manner known per se, as further described herein) and the resulting humanized VHH sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person. Also, based on the foregoing, (the framework regions of) an immunoglobulin single variable domains and/or Nanobody may be partially humanized or fully humanized.

Thus, in one specific, but non-limiting aspect, the immunoglobulin single variable domain and/or Nanobody may be a humanized immunoglobulin single variable domain and/or Nanobody, which consists of 4 framework regions (FR1 to FR4 respectively) and 3 complementarity determining regions (CDR1 to CDR3 respectively), in which CDR1 to CDR3 are as defined herein and in which said humanized immunoglobulin single variable domain and/or Nanobody comprises at least one humanizing substitution (as defined herein), and in particular at least one humanizing substitution in at least one of its framework sequences (as defined herein).

Some particularly preferred humanized immunoglobulin single variable domains and/or Nanobodies are humanized variants of the Nanobody of SEQ ID NO: 4 (SEQ ID NO: 572 of US 2010/0104568).

Some preferred, but non-limiting examples of such humanized variants are the humanized Nanobodies of SEQ ID NO's: 5-11 (SEQ ID NO's: 750-756 of US 2010/0104568). Thus, the invention also relates to a humanized Nanobody with an amino acid sequence that is chosen from the group consisting of SEQ ID NO's: 5-11 or from the group consisting of amino acid sequences that have more than 80%, preferably more than 90%, more preferably more than 95%, such as 99% or more sequence identity with at least one of the amino acid sequences of SEQ ID NO's: 5-11 (in which amino acid sequences that are chosen from the latter group of amino acid sequences may contain a greater number or a smaller number of humanizing substitutions compared to the corresponding sequence of SEQ ID NO's: 5-11, as long as they retain at least one of the humanizing substitutions present in the corresponding sequence of SEQ ID NO's: 5-11) in which SEQ ID NO: 10 is particularly preferred.

In particular, the immunoglobulin single variable domains used in the method of the invention may be:

amino acid sequences that are directed against (as defined herein) RANK-L and that have at least 80%, preferably at least 85%, such as 90% or 95% or more sequence identity with the amino acid sequences of SEQ ID NO's: 4-11 (SEQ ID NO's: 572 and 750-756 of US 2010/0104568). These amino acid sequences may further be such that they neutralize binding of RANK to RANK-L; and/or compete with RANK for binding to RANK-L; and/or are directed against an interaction site on RANK-L (such as the RANK or OPG binding site);

amino acid sequences that cross-block the binding of at least one of the amino acid sequences of SEQ ID NO's: 4-11 (SEQ ID NO's: 572 and 750-756 of US 2010/0104568) to RANK-L and/or that compete with at least one of the amino acid sequences of SEQ ID NO's: 4-11 (SEQ ID NO's: 572 and 750-756 of US 2010/0104568) for binding to RANK-L. Again, these amino acid sequences may further be such that they neutralize binding of the cognate ligand to RANK-L; and/or compete with the cognate ligand for binding to RANK-L; and/or are directed against an interaction site (as defined herein) on RANK-L (such as the RANK or OPG binding site); which amino acid sequences may be as further described herein (and may for example be Nanobodies); as well as polypeptides of the invention that comprise one or more of such amino acid sequences (which may be as further described herein, and may for example be bispecific and/or biparatopic polypeptides as described herein), and nucleic acid sequences that encode such amino acid sequences and polypeptides. Such amino acid sequences and polypeptides do not include any naturally occurring ligands.

According to a non-limiting but preferred aspect of the invention, (the CDR sequences present in) the immunoglobulin single variable domain and/or Nanobody are such that:

the immunoglobulin single variable domain and/or Nanobody can bind to RANK-L with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^{-5}$ to $10^{-12}$ liter/moles or more, and preferably $10^{-7}$ to $10^{-12}$ liter/moles or more and more preferably $10^8$ to $10^{12}$ liter/moles);

and/or such that:

the immunoglobulin single variable domain and/or Nanobody can bind to RANK-L with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^8$ $M^{-1}s^{-1}$ and $10^7$ $M^{-1}s^{-1}$;

and/or such that they:

the immunoglobulin single variable domain and/or Nanobody can bind to RANK-L with a $k_{off}$-rate between $1s^{-1}$ ($t_{1/2}$=0.69 s) and $10^{-6}s^{-1}$ (providing a near irreversible complex with a $t_{1/2}$ of multiple days), preferably between $10^{-2}$ $s^{-1}$ and $10^{-6}s^{-1}$, more preferably between $10^{-3}$ $s^{-1}$ and $10^{-6}s^{-1}$, such as between $10^{-4}$ $s^{-1}$ and $10^{-6}s^{-1}$.

Preferably, (the CDR sequences present in) the immunoglobulin single variable domain and/or Nanobody are such that: a monovalent immunoglobulin single variable domain and/or Nanobody of the invention (or a polypeptide that contains only one immunoglobulin single variable domain or Nanobody of the invention) is preferably such that it will bind to RANK-L with an affinity less than 500 nM, preferably less than 200 nM, more preferably less than 10 nM, such as less than 500 pM.

Polypeptide of the Invention

The immunoglobulin single variable domains and Nanobodies for use in the method of the invention are preferably in essentially isolated form, or form part of a polypeptide (referred herein as "polypeptide of the invention"), which may comprise or essentially consist of one or more immunoglobulin single variable domains and/or Nanobodies and which may optionally further comprise one or more further amino acid sequences (all optionally linked via one or more suitable linkers). The term "immunoglobulin single variable domain" may also encompass such polypeptide of the invention. For example, and without limitation, the one or more immunoglobulin single variable domains and/or Nanobodies may be used as a binding unit in such a polypeptide, which may optionally contain one or more further amino acid sequences that can serve as a binding unit, so as to provide a monovalent, multivalent or multispecific polypeptide of the invention, respectively, all as described herein. Such polypeptides may also be in essentially isolated form.

Generally, polypeptides that comprise or essentially consist of a single immunoglobulin single variable domain or Nanobody will be referred to herein as "monovalent" polypeptides or as "monovalent constructs". Polypeptides that comprise or essentially consist of two or more immunoglobulin single variable domains and/or Nanobodies will be referred to herein as "multivalent" proteins or polypeptides or as "multivalent constructs".

According to one specific, but non-limiting aspect, a polypeptide of the invention comprises or essentially consists of at least two immunoglobulin single variable domains and/or Nanobodies, such as two or three immunoglobulin single variable domains and/or Nanobodies. As further described herein, such multivalent constructs can provide certain advantages compared to a polypeptide comprising or essentially consisting of a single immunoglobulin single variable domain or Nanobody, such as a much improved avidity for RANK-L. Such multivalent constructs will be clear to the skilled person based on the disclosure herein; some preferred, but non-limiting examples of such multivalent constructs are the constructs of SEQ ID NO's: 625, 631, 637, 640-645, 649, 655, 661, 667, 673, 676-681, 685, 691, 761, 772 and 766, of US 2010/0104568 (bivalent) and SEQ ID NO's: 697, 703, 709, 712-717, 721, 727, and 759 of US 2010/0104568 (trivalent).

According to another specific, but non-limiting aspect, a polypeptide of the invention comprises or essentially consists of at least one immunoglobulin single variable domain and/or Nanobody and at least one other binding unit (i.e. directed against another epitope, antigen, target, protein or polypeptide), which is preferably also a immunoglobulin single variable domain and/or Nanobody. Such polypeptides are also referred to herein as "multispecific polypeptides or as "multispecific constructs", and these may provide certain advantages compared to the corresponding monovalent immunoglobulin single variable domains and/or Nanobodies (as will become clear from the further discussion herein of some preferred, but-nonlimiting multispecific constructs). Such multispecific constructs will be clear to the skilled person based on the disclosure herein; some preferred, but non-limiting examples of such multispecific Nanobody constructs are the constructs of SEQ ID NO's: 697, 703, 709, 712-717, 721, 727, and 759 of US 2010/0104568.

In another aspect, the polypeptide of the invention may comprises or essentially consists of one or more immunoglobulin single variable domains and optionally further comprises one or more other groups, residues, moieties or binding units. As will become clear to the skilled person from the further disclosure herein, such further groups, residues, moieties, binding units or amino acid sequences may or may not provide further functionality to the immunoglobulin single variable domain (and/or to the polypeptide in which it is present) and may or may not modify the properties of the immunoglobulin variable domain.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more polypeptides of the invention so as to provide a "derivative" of an immunoglobulin single variable domain or polypeptide of the invention.

As further described herein, a polypeptide of the invention may contain two or more immunoglobulin single variable domains that are directed against RANK-L. Generally, such polypeptides will bind to RANK-L with increased avidity compared to a single immunoglobulin single variable domain. Such a polypeptide may for example comprise two immunoglobulin single variable domains that are directed against the same antigenic determinant, epitope, part, domain, subunit or confirmation (where applicable) of RANK-L (which may or may not be an interaction site); or comprise at least one "first" immunoglobulin single variable domain that is directed against a first antigenic determinant, epitope, part, domain, subunit or confirmation (where applicable) of RANK-L (which may or may not be an interaction site); and at least one "second" immunoglobulin single variable domain that is directed against a second antigenic determinant, epitope, part, domain, subunit or confirmation (where applicable) different from the first (and which again may or may not be an interaction site). Preferably, in such "biparatopic" polypeptides of the invention, at least one immunoglobulin single variable domain is directed against an interaction site (as defined herein), although the invention in its broadest sense is not limited thereto. Examples of polypeptides of the invention are further described e.g. in WO 08/142,164.

Thus, in one particular aspect, a polypeptide of the invention may comprise two or more immunoglobulin single variable domains that are directed against the binding site for RANK on RANK-L; or comprise at least one "first" immunoglobulin single variable domain that is directed against the binding site for RANK on RANK-L; and at least one "second" immunoglobulin single variable domain that is directed against a second antigenic determinant, epitope, part, domain, subunit or confirmation different from the first and which is not a binding site for RANK on RANK-L.

It is also within the scope of the invention that, a polypeptide of the invention can bind to two or three subunits of RANK-L. In a preferred, but non-limiting aspect, the polypeptides of the invention bind two or three subunits of the RANK-L trimer.

In particular, according to this preferred embodiment, the invention relates to a polypeptide that comprises or essentially consist of two or more immunoglobulin single variable domains and/or Nanobodies that are each directed against epitopes on RANK-L (and in particular on the RANK-L trimer) that lie in and/or form part of the receptor binding site(s) of the RANK-L trimer, wherein said immunoglobulin single variable domains and/or Nanobodies are linked to each other in such a way that the polypeptide is capable of simultaneously binding to two or more receptor binding sites on a single RANK-L trimer (in other words, is capable of intramolecular binding to at least two RANK-L receptor binding sites on a RANK-L trimer). In this embodiment, the two or more immunoglobulin single variable domains and/or Nanobodies are preferably as defined above and are most preferably Nanobodies (so that the polypeptide is a multivalent Nanobody construct). Also, in this embodiment, the two or more immunoglobulin single variable domains and/or Nanobodies may be the same or different; and may be directed against different epitopes within the RANK receptor binding site(s), but are preferably directed against the same epitope. Some preferred, but non-limiting constructs of this embodiment of the invention are SEQ ID NO's: 625, 631, 637, 640-645, 649, 655, 661, 667, 673, 676-681, 685, 691, 697, 703, 709, 712-717, 721, 727, 759, 761, 772 and 766 of US 2010/0104568.

In the compounds or constructs described above, the one or more immunoglobulin single variable domains and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

In a particular embodiment of the invention, the two or more immunoglobulin single variable domains and/or Nanobodies will usually be linked via one or more suitable linkers, which linkers are such that each immunoglobulin single variable domain and/or Nanobody can bind to a different receptor binding site on the same RANK-L trimer. Suitable linkers will inter alia depend on (the distance between) the epitopes on the RANK-L trimer to which the immunoglobulin single variable domains and/or Nanobodies bind, and will be clear to the skilled person based on the disclosure herein, optionally after some limited degree of routine experimentation. For example, when the two or more immunoglobulin single variable domains are (single) domain antibodies or Nanobodies, suitable linkers may be chosen from the linkers described herein, but with a linker length that is such that the two or more (single) domain antibodies or Nanobodies can each bind to a different receptor binding site on the same RANK-L trimer.

More preferably, in this preferred aspect, the linker or spacer is an amino acid sequence that preferably has a length of from 1 up to 50 or more amino acids, more preferably from 5 to 30 amino acids, such as about 9 to 20 amino acids.

In one preferred, but non-limiting embodiment, the linker essentially consists of glycine and serine residues (as further described below). For example, one suitable linker is the GS9 linker described in US 2010/0104568, which comprises 9 amino acid residues, the GS15 linker described in US 2010/0104568, which comprises 15 amino acid residues, the GS20 linker described in US 2010/0104568, which comprises 20 amino acid residues and the GS30 linker described in US 2010/0104568, which comprises 30 amino acid residues, or any other linker known in the art such as e.g. depicted in Table A-1.

TABLE A-1

Sequence listing of linkers

| Linker | SEQ ID NO: | Sequences |
|---|---|---|
| 5GS | 16 | GGGGS |
| 7GS | 17 | SGGSGGS |
| GS8 | 18 | GGGGSGGGS |
| 9GS | 19 | GGGGSGGGS |
| 10GS | 20 | GGGGSGGGGS |
| 15GS | 21 | GGGGSGGGGSGGGGS |
| 18GS | 22 | GGGGSGGGGSGGGGGGGS |
| 20GS | 23 | GGGGSGGGGSGGGGSGGGGS |
| 25GS | 24 | GGGGSGGGGSGGGGSGGGGSGGGGS |
| 30GS | 25 | GGGGSGGGGSGGGGSGGGGSGGGGSGGGGS |
| 35GS | 26 | GGGGSGGGGSGGGGSGGGGSGGGGSGGGGSGGGGS |
| G1 hinge | 27 | EPKSCDKTHTCPPCP |
| 9GS-G1 hinge | 28 | GGGGSGGGSEPKSCDKTHTCPPCP |
| Llama upper long hinge region | 29 | EPKTPKPQPAAA |
| G3 hinge | 30 | ELKTPLGDTTHTCPRCPEPKSCDTPPPCPRCP EPKSCDTPPPCPRCPEPKSCDTPPPCPRCP |
| Ala | 31 | AAA |

In another embodiment, the at least two immunoglobulin single variable domains and/or Nanobodies against RANK-L are linked to each other via another moiety (optionally via one or two linkers), such as another protein or polypeptide. In this embodiment, it may be desirable to have the preferred distance (i.e. as mentioned above) between the N-terminus and the C-terminus of the at least two anti-RANK-L immunoglobulin single variable domains and/or Nanobodies, for example such that the protein or polypeptide can still undergo intramolecular binding (as described herein) with a RANK-L trimer. In this embodiment, the at least two immunoglobulin single variable domains and/or Nanobodies may be linked directly to the other moiety, or using a suitable linker or spacer, again as long as the preferred distance and/or desired intramolecular binding can still be achieved. The moiety may be any suitable moiety which does not detract (too much) from the binding of the polypeptide to RANK-L and/or from the further desired biological or pharmacological properties of the polypeptide.

As such, the moiety may be essentially inactive or may be biologically active, and as such may or may not improve the desired properties of the polypeptide and/or may confer one or more additional desired properties to the polypeptide. For example, and without limitation, the moiety may improve the half-life of the polypeptide, and/or may reduce its immunogenicity or improve any other desired property. In one preferred embodiment, the moiety may be another immunoglobulin single variable domains and/or Nanobody (including but not limited to a third immunoglobulin single variable domains and/or Nanobody against RANK-L, although this is not necessary and usually less preferred), and in particular another immunoglobulin single variable domains and/or Nanobody that improves the half-life of the polypeptide, such as an immunoglobulin single variable domains and/or Nanobody that is directed against a serum protein, for example against human serum albumin. Some non-limiting examples of such constructs are the constructs of SEQ ID NO's: 697, 703, 709, 712-717, 721, 717 and 759 of US 2010/0104568.

In one specific aspect of the invention, a polypeptide may have an increased half-life compared to the corresponding polypeptide of the invention. Some preferred, but non-limiting examples of such polypeptides will become clear to the skilled person based on the further disclosure herein, and for example comprise polypeptides of the invention that have been chemically modified to increase the half-life thereof (for example, by means of pegylation); polypeptides of the invention that comprise at least one additional binding site for binding to a serum protein (such as serum albumin); or polypeptides of the invention that comprise at least one immunoglobulin single variable domain that is linked to at least one moiety (and in particular at least one amino acid sequence) that increases the half-life of the immunoglobulin single variable domain of the invention. Examples of polypeptides of the invention that comprise such half-life extending moieties will become clear to the skilled person based on the further disclosure herein; and for example include, without limitation, polypeptides in which the one or more immunoglobulin single variable domains are suitable linked to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an immunoglobulin single variable domain is linked to an Fc portion (such as a human Fc) or a suitable part or fragment thereof; or polypeptides in which the one or more immunoglobulin single variable domains are suitable linked to one or more small proteins or peptides that can bind to serum proteins (such as, without limitation, the proteins and peptides described in WO 91/01743, WO 01/45746, WO 02/076489. Reference is also made to the dAb's described in WO 03/002609 and WO 04/003019 and to Harmsen et al. (Vaccine 23: 4926-42, 2005); to EP 0368684, as well as to WO 08/028,977, WO 08/043,821, WO 08/043,822 by Ablynx N.V. and WO 08/068,280.

Generally, the immunoglobulin single variable domains and/or Nanobodies used in the method of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding immunoglobulin single variable domains and/or Nanobodies per se. For example, the immunoglobulin single variable domains and/or Nanobodies, compounds, constructs or polypeptides used in the method of the invention may have a half-life that is increased with more than 1 hours, preferably more than 2 hours, more preferably more than 6 hours, such as more than 12 hours, or even more than 24, 48 or 72 hours, compared to the corresponding immunoglobulin single variable domain and/or Nanobody per se.

In a preferred, but non-limiting aspect of the invention, such immunoglobulin single variable domains and/or Nanobodies, compound, constructs or polypeptides used in the method of the invention exhibit a serum half-life in human of at least about 12 hours, preferably at least 24 hours, more preferably at least 48 hours, even more preferably at least 72 hours or more. For example, compounds or polypeptides used in the method of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more or more than 14 days (such as about 14 to 19 days).

A preferred polypeptide of the invention comprises one or more immunoglobulin single variable domains against RANK-L, e.g. according to SEQ ID NO's: 4-11, in particular SEQ ID NO: 10, in combination with at least one binding domain or peptide suitable for extending serum half life (preferably T1/2β) of the construct. In these constructs, the "serum-albumin binding domain or peptide" may be any suitable serum-albumin binding peptide or binding domain capable of increasing the half-life (preferably T1/2β) of the construct (compared to the same construct without the serum-albumin binding peptide or binding domain). Specifically, the polypeptide sequence suitable for extending serum half life is a polypeptide sequence capable of binding to a serum protein with a long serum half life, such as serum albumin, transferring, IgG, etc, in particular serum albumin. Polypeptide sequences capable of binding to serum albumin have previously been described and may in particular be serum albumin binding peptides as described in WO 08/068, 280 by applicant (and in particular WO 09/127,691 and WO 2011/095545, both by applicant), or a serum albumin binding immunoglobulin single variable domains (such as a serum-albumin binding Nanobody; for example Alb-1 or a humanized version of Alb-1 such as Alb-8, for which reference is for example made to WO 06/122787 and Table A-2).

TABLE A-2

Preferred, but non-limiting examples of albumin-binding Nanobodies

ALB-1, SEQ ID NO: 13
AVQLVESGGGLVQPGNSLRLSCAASGFTFRSFGMSWVRQAPGKEPEWVSS
ISGSGSDTLYADSVKGRFTISRDNAKTTLYLQMNSLKPEDTAVYYCTIGG
SLSRSSQGTQVTVSS

ALB-8(humanized ALB-1), SEQ ID NO: 14
EVQLVESGGGLVQPGNSLRLSCAASGFTFSSFGMSWVRQAPGKGLEWVSS
ISGSGSDTLYADSVKGRFTISRDNAKTTLYLQMNSLRPEDTAVYYCTIGG
SLSRSSQGTLVTVSS TABLE A-2-continued Preferred, but non-limiting examples of albumin-binding Nanobodies ALB-2, SEQ ID NO: 15
AVQLVESGGGLVQGGGSLRLACAASERIFDLNLMGWYRQGPGNERELVAT
CITVGDSTNYADSVKGRFTISMDYTKQTVYLHMNSLRPEDTGLYYCKIRR
TWHSELWGQGTQVTVSS Preferred immunoglobulin single variable domains that bind serum albumin include SEQ ID NOs: 13-15. In some embodiments, the immunoglobulin single variable domain comprises or consists of SEQ ID NO: 14 (SEQ ID NO: 791 of US 2010/0104568).

Thus, in one embodiment, the invention relates to a multivalent multispecific construct comprising two or more immunoglobulin single variable domains and/or Nanobodies that are each directed against epitopes on RANK-L (e.g. on the RANK-L trimer) that lie in and/or form part of the receptor binding site, and that are linked to each other via at least one immunoglobulin single variable domains and/or Nanobody that provides for increased half-life (and optionally via one or more suitable linkers), such that said polypeptide, upon binding to a RANK-L trimer, is capable of inhibiting or reducing the RANK receptor binding and/or the signal transduction that is mediated by said RANK-L trimer. Such a polypeptide may be such that said firstmentioned two or more immunoglobulin single variable domains and/or Nanobodies can each bind to a different receptor binding site on a RANK-L trimer.

In particular, in this embodiment, the polypeptide may comprise a trivalent bispecific Nanobody, that comprises two Nanobodies that are each directed against epitopes on RANK-L (and in particular of the RANK-L trimer) that lie in and/or form part of the receptor binding site, in which said Nanobodies are linked to each other via a third Nanobody that provides for an increased half-life (e.g. a Nanobody that is directed to a serum protein such as human serum albumin), in which each of the firstmentioned two Nanobodies may be directly linked to said third Nanobody or via one or more suitable linkers, such that said polypeptide, upon binding to a RANK-L trimer, is capable of inhibiting or reducing the RANK receptor binding and/or the signal transduction that is mediated by said RANK-L trimer. Such a polypeptide may be such that said firstmentioned two Nanobodies can each bind to a different receptor binding site on a RANK-L trimer. Again, a particularly preferred Nanobody for use in this embodiment of the invention is presented in SEQ ID NO: 4 (SEQ ID NO: 572 of US 2010/0104568), as well as humanized and other variants thereof (such as e.g. SEQ ID NO: 10 (SEQ ID NO: 755 of US 2010/0104568)); and the Nanobodies directed against human serum albumin described herein. Are preferred, but non-limiting constructs of this embodiment of the invention is SEQ ID NO: 12 (SEQ ID NO: 759 of US 2010/0104568).

Other polypeptides according to this preferred aspect of the invention may for example be chosen from the group consisting of polypeptides that have more than 80%, preferably more than 90%, more preferably more than 95%, such as 99% or more "sequence identity" (as defined herein) with the polypeptide of SEQ ID NO: 12 (SEQ ID NO: 759 of US 2010/0104568), in which the Nanobodies comprised within said polypeptides are preferably as further defined herein.

The polypeptides (of the invention) administered in the methods of the invention, i.e., that specifically bind RANKL, in some embodiments have an apparent $K_D$ for binding to recombinant soluble RANKL (sRANKL), as determined by Biacore assay, of 0.005-0.1 nM, such as 0.005-0.05 nM, 0.01-0.1 nM, 0.01-0.05 nM, including the values at the ends of each range, such as 0.005 nM, 0.006 nM, 0.007 nM, 0.008 nM, 0.009 nM, 0.01 nM, 0.011 nM, 0.012 nM, 0.013 nM, 0.014 nM, 0.015 nM, 0.016 nM, 0.017 nM, 0.018 nM, 0.019 nM, 0.02 nM, 0.021 nM, 0.022 nM, 0.023 nM, 0.024 nM, 0.025 nM, 0.026 nM, 0.027 nM, 0.028 nM, 0.029 nM, 0.03 nM, 0.031 nM, 0.032 nM, 0.033 nM, 0.034 nM, 0.035 nM, 0.036 nM, 0.037 nM, 0.038 nM, 0.039 nM, 0.04 nM, 0.041 nM, 0.042 nM, 0.043 nM, 0.044 nM, 0.045 nM, 0.046 nM, 0.047 nM, 0.048 nM, 0.049 nM, 0.05 nM, 0.06 nM, 0.07 nM, 0.08 nM, 0.09 nM, or 0.1 nM, and preferably about 0.04 nM.

EC50 values for binding of the Nanobodies of the invention (and of polypeptides comprising the same) to RANK-L in, for example ELISA or FACS are preferably 1 µM to 1 pM, more preferably 1 nM to 1 pM and more preferably 100 pM to 1 pM. IC50 values for binding of the Nanobodies of the invention (and of polypeptides comprising the same) to RANK-L in, for example, AlphaScreen®, NF-kappaB assay or TRAP assay are preferably 1 µM to 1 pM, more preferably 1 nM to 1 pM and more preferably 100 pM to 1 pM (as described in WO 2008/142164).

In another aspect of the present invention, the polypeptides of the invention are preferably directed against an epitope on RANK-L that overlaps with the epitope of Denosumab or the epitope of SEQ ID NO: 755 of US 2010/0104568. Binding of the amino acid sequences and polypeptides of the invention to an epitope on RANK-L that overlaps with the epitope of Denosumab or the epitope of SEQ ID NO: 755 of US 2010/0104568 may inhibit and/or prevent binding of Denosumab or of SEQ ID NO: 755 of US 2010/0104568 to RANK-L. The polypeptides of the invention may therefore act as a competitive or as a non-competitive inhibitor of the binding of Denosumab or of SEQ ID NO: 755 of US 2010/0104568 to RANK-L (e.g. in ELISA, in AlphaScreen® assay, in TRAP assay and/or in NFkappaB assay).

Additional embodiments of polypeptides that are useful in the methods described herein are described in WO 08/142, 164, US 2010/0104568A1, and US 2011/0002929A1.

Although the use of immunoglobulin single variable domains and, in particular, Nanobodies as defined herein and of the polypeptides of the invention is much preferred, it will be clear that on the basis of the description herein, the skilled person will also be able to design and/or generate, in an analogous manner, other polypeptides and in particular (single) domain antibodies against RANK-L, as well as polypeptides comprising such (single) domain antibodies that can be used in the methods of the invention.

For example, it will also be clear to the skilled person that it may be possible to "graft" one or more of the CDR's mentioned above for the Nanobodies onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al. (2004, Protein Science 13: 1882-1891), Ewert et al. (2004, Methods 34(2): 184-199), Kettleborough et al. (1991, Protein Eng. 4(7): 773-783), O'Brien and Jones (2003, Methods Mol. Biol. 207: 81-100), Skerra J. (2000 Mol. Recognit. 13: 167-187), and Saerens et al. (2005, J. Mol. Biol. 352(3): 597-607), and the further references cited therein. For example, techniques known per se for grafting mouse or rat CDR's onto human frameworks and scaffolds can be used in an analogous manner to provide chimeric proteins comprising one or more of the CDR's of the Nanobodies described herein and one or more human framework regions or sequences.

Generally, in this aspect of the invention, the polypeptides used in the method of the invention may be any polypeptide that comprises at least one stretch of amino acid residues, in which said stretch of amino acid residues has an amino acid sequence that corresponds to the sequence of at least one of the CDR sequences described herein. Such a polypeptide may or may not comprise an immunoglobulin fold. For example, and without limitation, such a polypeptide may be a suitable fragment of an immunoglobulin sequence that comprises at least one such CDR sequence, but that is not large enough to form a (complete) immunoglobulin fold (reference is for example again made to the "Expedite fragments" described in WO 03/050531). Alternatively, such a polypeptide may be a suitable "protein scaffold" that comprises least one stretch of amino acid residues that corresponds to such a CDR sequence (i.e. as part of its antigen binding site). Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. 2005, Nat. Biotech, 23: 1257), and binding moieties based on DNA or RNA including but not limited to DNA or RNA aptamers (Ulrich et al. 2006, Comb. Chem. High Throughput Screen 9(8): 619-32).

The immunoglobulin single variable domains, Nanobodies, polypeptides and nucleic acids used in the method of the invention can be prepared in a manner known per se, as will be clear to the skilled person from the further description herein. For example, the immunoglobulin single variable domains, Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the immunoglobulin single variable domains, Nanobodies, polypeptides and nucleic acids include the methods and techniques described herein.

As will be clear to the skilled person, one particularly useful method for preparing an immunoglobulin single variable domains, Nanobody and/or a polypeptide of the invention generally comprises the steps of:
i) the expression, in a suitable host cell or host organism (also referred to herein as a "host of the invention") or in another suitable expression system of a nucleic acid that encodes said immunoglobulin single variable domains, Nanobody or polypeptide of the invention, optionally followed by:
ii) isolating and/or purifying the immunoglobulin single variable domains, Nanobody or polypeptide of the invention thus obtained.

In particular, such a method may comprise the steps of:
i) cultivating and/or maintaining a host under conditions that are such that said host expresses and/or produces at least one immunoglobulin single variable domains, Nanobody and/or polypeptide of the invention; optionally followed by:

ii) isolating and/or purifying the immunoglobulin single variable domains, Nanobody or polypeptide of the invention thus obtained.

According to one preferred, but non-limiting embodiment, the polypeptide of the invention is produced in a bacterial cell, in particular a bacterial cell suitable for large scale pharmaceutical production. According to another preferred, but non-limiting embodiment, the polypeptide of the invention is produced in a yeast cell, in particular a yeast cell suitable for large scale pharmaceutical production. According to yet another preferred, but non-limiting embodiment, the polypeptide of the invention is produced in a mammalian cell, in particular in a human cell or in a cell of a human cell line, and more in particular in a human cell or in a cell of a human cell line that is suitable for large scale pharmaceutical production.

For production on industrial scale, preferred heterologous hosts for the (industrial) production of Nanobodies or Nanobody-containing protein therapeutics include strains of *E. coli, Pichia pastoris, S. cerevisiae* that are suitable for large scale expression/production/fermentation, and in particular for large scale pharmaceutical expression/production/fermentation. Suitable examples of such strains will be clear to the skilled person.

Alternatively, mammalian cell lines, in particular Chinese hamster ovary (CHO) cells, can be used for large scale expression/production/fermentation, and in particular for large scale pharmaceutical expression/production/fermentation.

Subsequently, the polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds.

Thus, in a further aspect, the invention relates to a pharmaceutical composition that contains at least one polypeptide of the invention and at least one suitable carrier, diluent or excipient (i.e. suitable for pharmaceutical use), and optionally one or more further active substances, which when administered to a subject (e.g., a human, such as an osteoporosis patient, for example a post-menopausal female) inhibits bone resorption and/or osteoclast activity for prolonged periods of time and/or is effective to change one or more markers of bone metabolism and/or bone homeostasis, such as to reduce serum level of cross-linking telopeptide of type I collagen (CTX-1), by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration, such as 30 days to 3 months, 3 months to 6 months, or 6 months to 1 year.

Generally, polypeptides of the invention can be formulated and administered in any suitable manner known per se, for which reference is for example made to the general background art cited above (and in particular to WO 04/041862, WO 04/041863, WO 04/041865, WO 04/041867, WO 08/020,079 and WO 2011/026945) as well as to the standard handbooks, such as Remington's Pharmaceutical Sciences, 18th Ed., Mack Publishing Company, USA (1990) or Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

For example, the polypeptides of the invention may be formulated and administered in any manner known per se for conventional antibodies and antibody fragments (including scFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration).

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The polypeptides of the invention may also be administered subcutaneously, intravenously or intraperitoneally by infusion or injection. Solutions of the polypeptides of the invention or their salts can be prepared in water, optionally mixed with a nontoxic surfactant and/or one or more buffer components. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

The invention, however, also encompasses products obtainable by further processing of a liquid formulation, such as a frozen, lyophilized or spray dried product. Upon reconstitution, these solid products can become liquid formulations as described herein (but are not limited thereto). In its broadest sense, therefore, the term "formulation" encompasses both liquid and solid formulations. However, solid formulations are understood as derivable from the liquid formulations (e.g. by freezing, freeze-drying or spray-drying), and hence have characteristics that are defined by the features specified for liquid formulations herein. The invention does not exclude reconstitution that leads to a composition that deviates from the original composition before e.g. freeze- or spray drying.

Sterile injectable solutions are prepared by incorporating the polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Preferred formulation for parental administration of the polypeptides, immunoglobulin single variable domains and/or Nanobodies described herein are described in WO 2011/026945.

Generally, the concentration of the polypeptides of the invention in a liquid composition, such as an injectable or infusible preparation, or a lotion, will be from about 0.1-25 wt-%, preferably from about 0.5-10 wt-%, although the amounts are not limited to these ranges and may be higher or lower weight percentages depending on the need for higher or lower doses that can be administered in a volume that is suitable. The concentration in a semi-solid or solid composition such as a gel or a powder will be about 0.1-5 wt-%, preferably about 0.5-2.5 wt-%.

As demonstrated herein in the working examples, concentrations of 0.65 mg/mL, 2.17 mg/mL, 6.5 mg/mL, 21.7 mg/mL and 65 mg/mL have been used. It is expected that other concentrations having values between these concentrations (and also outside these values, i.e., higher or lower than these values) therefore also can be used. For example, concentrations of 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mg/mL can be used.

To obtain the unexpected prolonged and sustained effects described herein, the polypeptide of the invention is administered in an amount from about 0.003 mg/kg to about 10 mg/kg. Exemplary dose ranges (inclusive of the values at the ends of each range) include 0.003-10 mg/kg, such as 0.003-3 mg/kg, 0.003-1 mg/kg, 0.003-0.3 mg/kg, 0.003-0.1 mg/kg, 0.003-0.03 mg/kg, 0.003-0.01 mg/kg, 0.01-10 mg/kg, 0.01-3 mg/kg, 0.01-1 mg/kg, 0.01-0.3 mg/kg, 0.01-0.1 mg/kg, 0.01-0.03 mg/kg, 0.03-10 mg/kg, 0.03-3 mg/kg, 0.03-1 mg/kg, 0.03-0.3 mg/kg, 0.03-0.1 mg/kg, 0.1-10 mg/kg, 0.1-3 mg/kg, 0.1-1 mg/kg, 0.1-0.3 mg/kg, 0.3-10 mg/kg, 0.3-3 mg/kg, 0.3-1 mg/kg, 1-10 mg/kg, 1-3 mg/kg, and 3-10 mg/kg. Exemplary doses include 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10 mg/kg.

Necessary modifications in the given dosage ranges may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

Therapeutic Applications

The invention thus relates to a method for the prevention and/or treatment of at least one bone disease and/or disorder, said method comprising administering, to a subject in need thereof, a pharmaceutically active amount of a polypeptide of the invention, and/or of a pharmaceutical composition comprising the same. More in particular, the invention relates to the polypeptides described herein for use in therapy of bone diseases and/or disorders.

The methods and dosing schedules of the present invention can be used for the prevention and treatment of bone diseases and/or disorders. In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The invention relates to a method for the prevention and/or treatment of at least one disease and/or disorder that is associated with RANK-L, with its biological or pharmacological activity, and/or with the biological pathways or signalling in which RANK-L is involved, said method comprising administering, to a subject in need thereof, a pharmaceutically active amount of a polypeptide of the invention, and/or of a pharmaceutical composition comprising the same. In particular, the invention relates to a method for the prevention and/or treatment of at least one disease and/or disorder that can be treated by modulating RANK-L, its biological or pharmacological activity, and/or the biological pathways or signalling in which RANK-L is involved, said method comprising administering, to a subject in need thereof, a pharmaceutically active amount of a polypeptide of the invention, and/or of a pharmaceutical composition comprising the same. In particular, said pharmaceutically effective amount may be an amount that is effective to change one or more markers of bone metabolism and/or bone homeostasis, such as:

to reduce serum levels of cross-linking telopeptide of type I collagen (CTX-1), by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration;
  to reduce levels of N-terminal telopeptide of type I collagen (NTX-1), determined as ratio of NTX-1 to creatinine in urine, by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration;

to reduce serum levels of tartrate-resistant acid phosphatase isoform 5b (TRACP5b), by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration;

to reduce serum levels of N-terminal propeptide of type I procollagen (P1NP), by at least 30%, more preferably at least 35%, more preferably at least 40%, more preferably at least 45%, more preferably at least 50%, more preferably at least 55%, more preferably at least 60%, more preferably at least 65%, more preferably at least 70%, such as at least 75%, or even at least 80%, compared to pre-treatment or normal levels, for at least about 30 days after administration;

The subject to be treated may be a human being. As will be clear to the skilled person, the subject to be treated will in particular be a person suffering from, or at risk of, the diseases and/or disorders mentioned herein. For example, the subject may be a person suffering from, or at risk of, osteoporosis, and in particular a human female, more particularly a post-menopausal human female.

The methods and dosing schedules of the present invention can be used for the prevention and treatment of bone diseases and/or disorders with lower doses and/or less frequent dosing than with other therapeutics. Generally, "bone diseases and/or disorders" can be defined as diseases and/or disorders that can be prevented and/or treated, respectively, by suitably administering to a subject in need thereof (i.e. having the disease and/or disorder or at least one symptom thereof and/or at risk of attracting or developing the disease and/or disorder) of either a polypeptide of the invention or composition comprising the same (and in particular, of a pharmaceutically active amount thereof) and/or of a known active principle active against RANK-L or a biological pathway or mechanism in which RANK-L is involved (and in particular, of a pharmaceutically active amount thereof).

Bone diseases and/or disorders encompass diseases and/or disorders associated with the regulation of bone formation and resorption. Bone diseases and/or disorders characterized by a net bone loss (bone resorption exceeds bone formation) are also referred to as osteopenic disorders, including ostopenia, osteoporosis and osteolysis and are characterized by excessive and/or unwanted signaling mediated by RANK-L. The methods and dosing schedules of the present invention that modulate, and in particular inhibit and/or prevent for prolonged periods of time and/or at lower doses and/or by less frequent dosing, binding of RANK-L to RANK act as antagonist and will generally be used for the prevention and/or treatment of bone diseases and/or disorders characterized by net bone loss.

Examples of such bone diseases and/or disorders will be clear to the skilled person based on the disclosure herein, and for example include the following diseases and/or disorders: osteoporosis (McClung 2006, Current Osteoporosis Reports 4: 28-33), including, but not limited to, primary osteoporosis, endocrine osteoporosis (including, but not limited to, hyperthyroidism, hyperparathyroidism (Anandarajah and Schwarz 2006, J. Cell Biochem. 97: 226-232), Cushing's syndrome, and acromegaly), hereditary and congenital forms of osteoporosis (including, but not limited to, osteogenesis imperfecta, homocystinuria, Menkes' syndrome, Riley-Day syndrome), osteoporosis due to immobilization of extremities, glucocorticoid-induced osteoporosis (Locklin et al. 2001, Bone 28 (Suppl.): S80; McClung 2006, Current Osteoporosis Reports 4: 28-33; Anandarajah and Schwarz 2006, J. Cell Biochem. 97: 226-232) and post-menopausal osteoporosis (McClung 2006, Current Osteoporosis Reports 4: 28-33).

Also encompassed within the scope of the present invention is the prevention and/or treatment, using the methods and dosing schedules of the invention, of other diseases and/or disorders associated with an imbalance in the RANK-L/RANK/OPG pathway. Such diseases and/or disorders include but are not limited to osteoporosis.

Accordingly, some embodiments of the present invention provide use polypeptides that are directed against RANK-L, in particular against human RANK-L, for unexpectedly prolonged inhibition of bone resorption and/or osteoclast activity in a subject. In particular, some embodiments of the present invention provide use of such polypeptides for prophylactic, therapeutic and/or diagnostic use in a human being, and particularly for unexpectedly prolonged inhibition of bone resorption and/or osteoclast activity in a subject.

More in particular, some embodiments of the present invention provide use of such polypeptides for the prevention, prophylaxis, treatment, alleviation and/or diagnosis of one or more diseases, disorders or conditions associated with RANK-L and/or mediated by RANK-L (such as the diseases, disorders and conditions mentioned herein) in a human being, and particularly for unexpectedly prolonged inhibition of bone resorption and/or osteoclast activity in a subject, such as for treatment or prophylaxis of osteoporosis.

Some embodiments of the present invention provide such polypeptides for use in the preparation of pharmaceutical compositions for the prevention and/or treatment of one or more diseases, disorders or conditions associated with and/or mediated by RANK-L (such as the diseases, disorders and conditions mentioned herein) in a human being.

In another aspect, the invention relates to a polypeptide of the invention for prevention and/or treatment of at least one bone disease and/or disorder; and/or for use in one or more of the methods of treatment mentioned herein.

In another aspect, the invention relates to the use of a polypeptide of the invention in the preparation of a pharmaceutical composition for prevention and/or treatment of at least one bone disease and/or disorder; and/or for use in one or more of the methods of treatment mentioned herein.

In particular, the polypeptides of the invention may be used in combination with other pharmaceutically active compounds or principles that are or can be used for the prevention and/or treatment of the diseases and/or disorders cited herein, as a result of which a synergistic effect may or may not be obtained. Examples of such compounds and principles, as well as routes, methods and pharmaceutical formulations or compositions for administering them will be clear to the clinician.

In particular, the pharmaceutical composition of the invention may comprise one or more polypeptides of the invention and at least one additional therapeutic agent selected from a bone morphogenic factor, transforming growth factor-β (TGF-β), an interleukin-1 (IL-1) inhibitor, IL-1ra, Kineret™, a TNFα inhibitor, a soluble TNFα receptor, Enbrel™, an anti-TNFα antibody, Remicade™, a D2E7 antibody, a parathyroid hormone, an analog of a parathyroid hormone, a parathyroid hormone related protein, an analog of a parathyroid hormone related protein, a prostaglandin, a bisphosphonate, an alendronate, fluoride, calcium, a non-steroidal anti-inflammatory drug (NSAID), a COX-2 inhibitor, Celebrex™, Vioxx™, an immunosuppressant, methotrexate, leflunomide, a serine protease inhibitor, a secretory leukocyte protease inhibitor (SLPI), an IL-6 inhibitor, an antibody or Nanobody against IL-6, an IL-8 inhibitor, an antibody or Nanobody against IL-8, an IL-18 inhibitor, an IL-18 binding protein, an antibody or Nanobody against IL-18, an Interleukin-1 converting enzyme (ICE) modulator, a fibroblast growth factor (FGF), an FGF modulator, a PAF antagonist, a keratinocyte growth factor (KGF), a KGF-related molecule, a KGF modulator, a matrix metalloproteinase (MMP) modulator, a nitric oxide synthase (NOS) modulator, a modulator of glucocorticoid receptor, a modulator of glutamate receptor, a modulator of lipopolysaccharide (LPS) levels, a noradrenaline, a noradrenaline mimetic, and a noradrenaline modulator as described, for example, in US 2004/00335353

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

DEFINITIONS

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley &Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews: Presta (2006, Adv. Drug Deliv. Rev. 58 (5-6): 640-56); Levin and Weiss (2006, Mol. Biosyst. 2(1): 49-57); Irving et al. (2001, J. Immunol. Methods, 248(1-2): 31-45); Schmitz et al. (2000, Placenta, 21 Suppl. A: S106-12), Gonzales et al. (2005, Tumour Biol. 26(1): 31-43), which describe techniques for protein engineering, such as affinity maturation and other techniques for improving the specificity and other desired properties of proteins such as immunoglobulins.

A nucleic acid sequence or amino acid sequence is considered to be "(in) essentially isolated (form)"—for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the firstmentioned nucleotide sequence or amino acid sequence, respectively, but more usually this generally means that the firstmentioned nucleotide sequence or amino acid sequence comprises within its sequence a stretch of nucleotides or amino acid residues, respectively, that has the same nucleotide sequence or amino acid sequence, respectively, as the latter sequence, irrespective of how the firstmentioned sequence has actually been generated or obtained (which may for example be by any suitable method described herein). By means of a non-limiting example, when a Nanobody or polypeptide of the invention is said to comprise a CDR sequence, this may mean that said CDR sequence has been incorporated into the Nanobody or polypeptide of the invention, but more usually this generally means that the Nanobody or polypeptide of the invention contains within its sequence a stretch of amino acid residues with the same amino acid sequence as said CDR sequence, irrespective of how said Nanobody or polypeptide of the invention has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a Nanobody or polypeptide of the invention is said to comprise a CDR sequence or framework sequence, respectively, the CDR sequence and framework are preferably capable, in said Nanobody or polypeptide, of functioning as a CDR sequence or framework sequence, respectively. Also, when a nucleotide sequence is said to comprise another nucleotide sequence, the firstmentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

By "essentially consist of" is meant that the first mentioned nucleic acid sequence or amino acid sequence is exactly the same as the latter sequence or corresponds to the latter sequence which has a limited number of nucleic acids or amino acid residues, such as (encoding) 1-20 amino acid residues, for example (encoding) 1-10 amino acid residues and preferably (encoding) 1-6 amino acid residues, such as (encoding) 1, 2, 3, 4, 5 or 6 amino acid residues, added at the amino terminal end, at the carboxy terminal end, or at both the amino terminal end and the carboxy terminal end of the nucleic acid or amino acid sequence.

An amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

The term "specificity" refers to the number of different types of antigens or antigenic determinants to which a particular antigen-binding molecule or antigen-binding protein (such as a Nanobody or a polypeptide of the invention) can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule or antigen-binding protein (such as a Nanobody or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ M$^4$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g., of $10^{-2}$ mmoles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or M$^{-1}$). In the present specification, the stability of the interaction between two molecules (such as a Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$. The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $k_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}=0.69$ s). The affinity of a molecular interaction between two molecules can be measured via different techniques known per se, such as the well known surface plasmon resonance (SPR) biosensor technique (see for example Ober et al. 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (1985, J. Immunol. Methods, 77: 305-19). This method establishes a solution phase binding equilibrium measurement and avoids possible artefacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_{D\ ref}$ the $K_D$ of the reference molecule, is known, as well as the total concentration $c_{ref}$ of the reference molecule, the apparent $K_D$ for the interaction A-B can be obtained from following formula: $K_D=IC_{50}/(1+C_{ref}/K_{D\ ref})$. Note that if $C_{ref} \ll K_{D\ ref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

The half-life of a compound or polypeptide of the invention can generally be defined as the time taken for the serum concentration of the compound or polypeptide to be reduced by 50%, in vivo, for example due to degradation of compound or polypeptide and/or clearance or sequestration of the compound or polypeptide by natural mechanisms. The in vivo half-life of a compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatto*)) and baboon (*Papio ursinus*)) a suitable dose of the compound or polypeptide of the invention; collecting blood samples or other samples from said animal; determining the level or concentration of the compound or polypeptide of the invention in said blood sample; and calculating, from (a plot of) the data thus obtained, the time until the level or concentration of the compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

For the purposes of comparing two or more nucleotide sequences, the percentage of "sequence identity" between a first nucleotide sequence and a second nucleotide sequence is as defined in WO 08/142,164 on pages 58-60 point e) and g).

For the purposes of comparing two or more amino acid sequences, the percentage of "sequence identity" between a first amino acid sequence and a second amino acid sequence is as defined in WO 08/142,164 on pages 58-60, points f), g) and h.

The term "antigenic determinant" refers to the epitope on the antigen recognized by the antigen-binding molecule (such as a Nanobody or a polypeptide of the invention) and more in particular by the antigen-binding site of said molecule. The terms "antigenic determinant" and "epitope" may also be used interchangeably herein.

The terms "cross-block", "cross-blocked" and "cross-blocking" are used interchangeably herein and have the meaning as described on page 69-72, point s) of WO 08/142,164.

The amino acid residues of a Nanobody are numbered according to the general numbering for VH domains given by Kabat et al. ("Sequence of proteins of immunological interest", US Public Health Services, NIH Bethesda, Md., Publication No. 91), as applied to VHH domains from Camelids in the article of Riechmann and Muyldermans (2000, J. Immunol. Methods 240 (1-2): 185-195 (see for example FIG. 2 of this publication)); or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acid residues at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

A polypeptide of the invention is said to reduce levels of a marker (such as e.g. CTX-1, NTX-1, TRACP5b or P1NP) "by at least x %" or to reduce levels of a marker "by at least x % compared to pre-treatment or normal levels" if administration of the polypeptide of the invention to the subject results in a reduction of the levels of said marker of x % compared to the levels before the treatment or compared to normal levels. This means that the levels of the marker in the treated subject will be x % lower compared to the levels of the marker before treatment or compared to the normal levels of the marker. Thus, when the levels of the marker before treatment or the normal levels of the marker are set at 100%, the levels of the marker in the treated subject (reduced levels of the marker) will be 100%-x % of the levels before treatment or the normal levels of the marker. These levels of the marker in the treated subject are therefore also said to be "100%-x % of baseline". For example, if a polypeptide of the invention is said to "reduce serum levels of CTX-1 by at least 30%" or to "reduce serum levels of CTX-1 by at least 30% compared to pre-treatment or normal levels, the serum levels of CTX-1 in the treated subject will be 30% lower compared to the levels of CTX-1 before treatment or compared to the normal levels of CTX-1. Thus, when the levels of CTX-1 before treatment or the normal levels of CTX-1 are set at 100%, the levels of CTX-1 in the treated subject (reduced levels of CTX-1) will be 70% (100%-30%) of the CTX-1 levels before treatment or the normal levels of CTX-1. These levels of CTX-1 in the treated subject are therefore also said to be "70% of baseline".

A polypeptide of the invention is said to maintain levels of a marker (such as e.g. CTX-1, NTX-1, TRACP5b or P1NP) "at at least x %" if the reduced levels of the marker are maintained x % lower compared to the levels of the marker before treatment or compared to the normal levels of the marker. Accordingly, the levels of the marker are maintained at "100%-x % of baseline". For example a polypeptide of the invention is said to maintain serum levels of CTX-1 "at least 30%" if the reduced levels of serum CTX-1 are maintained 30% lower compared to the CTX-1 levels before treatment or compared to the normal levels of CTX-1. Accordingly, the levels of CTX-1 are maintained at "70% of baseline".

The Figures, and the Experimental Part/Examples are only given to further illustrate the invention and should not be interpreted or construed as limiting the scope of the invention and/or of the appended claims in any way, unless explicitly indicated otherwise herein.

The invention will now be further described by means of the following non-limiting examples and figures:

EXAMPLES

List of Abbreviations

Figure 1:
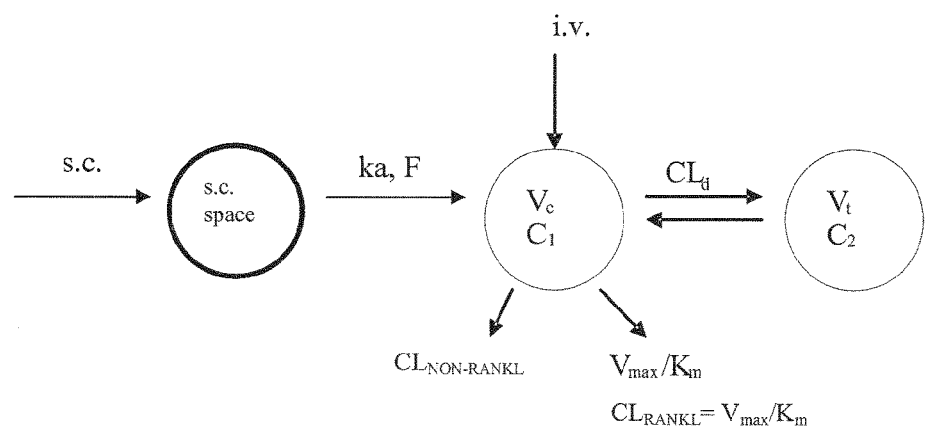
FIG. 1: Open two-compartmental pharmacokinetic model with linear and non-linear clearance from the central compartment. $CL_{NON-RANKL}$ is the linear non-RANKL mediated clearance, Vc the volume of the central compartment, Vt the volume of the peripheral compartment, CLd the inter-compartmental flow, and $CL_{RANKL}$ is the non-linear RANKL-mediated clearance ($V_{max}$ the maximum metabolic rate and $K_m$ the ALX-0141 concentration corresponding to 50% of $V_{max}$). The absorption rate constant and the bioavailability after s.c. administration are represented by Ica and F, respectively.

| Symbol | Unit | Definition |
|---|---|---|
| ADA | — | Anti-drug antibody |
| $AUC_{inf}$ | (ug · d/mL) | Area under the plasma drug concentration-time curve extrapolated to infinity |
| $AUC_{last}$ | (ug · d/mL) | Area from time zero to the last measurable concentration after dosing |
| BAP | — | Bone specific alkaline phsophatase |
| BED | mg/kg | biological effective dose |
| b.w. | — | Body weight |
| C | Amount/volume | ALX-0141 plasma concentration |
| CL | Volume/time*kg | Apparent total body clearance of the drug from serum |
| $CL_d$ | Volume/time*kg | Inter-compartmental flow |
| $CL_{RANKL}$ | Volume/time*kg | Non-linear RANKL-mediated clearance |
| $CL_{NON-RANKL}$ | Volume/time*kg | Linear non-RANKL mediated clearance |
| CTX-1 | — | C-terminal cross-linked telopeptide of type I collagen |
| D | Amount/kg | Dose |
| F | — | s.c. bioavailability |
| i.v. | — | Intravenous |
| F1 | — | Fraction of the dose absorbed with $k_{a1}$ |
| F2 | — | Fraction of the dose absorbed with $k_{a2}$ |
| $I_{max}$ | % | Maximum inhibition of serum CTX-1 ($1 < I_{max} < 0$) |
| $k_a$ | 1/time | Absorption rate constant (s.c. administration) |
| $k_{in}$ | Amount/volume*time | Zero-order synthesis rate |
| $k_{a1}$ | 1/time | Fast first order absorption rate constant (s.c. administration) |
| $k_{a2}$ | 1/time | Slow order absorption rate constant (s.c. administration) |
| $k_{out}$ | 1/time | First order elimination rate constant of serum CTX-1 |
| $K_m$ | Amount/volume | ALX-0141 concentration corresponding to 50% of $V_{max}$ ($CL_{RANKL}$). |
| $Lk_{in}$ | — | typical fractional dose effect on $k_{in}$ at the lower doses (0.003 and 0.01 mg/kg) |
| LLOQ | — | Lower limit of quantification |
| nadir | — | The lowes point in the curve |
| n | — | Concentration-response shape factor |
| NTX-1 | — | N-terminal telopeptide of type 1 collagen |
| P1NP | — | Procollagen type 1 amino-terminal propeptide |
| RANK(L) | — | Receptor activator for nuclear factor kappa B (ligand) |
| R | Amount/volume | (Pharmacodynamic) Response (i.e. serum CTX-1 level) |
| s.c. | — | Subcutaneous |
| $t_{1/2, terminal}$ | Time | Terminal elimination half-life calculated as $\ln(2)/\lambda_z$ |
| TRACP5b | — | Tartrate-resistant acid phosphatase |
| $V_c$ | Volume/kg | Apparent volume of the central or plasma compartment in a two-compartment model |
| $Vd_{ss}$ | Volume/kg | Apparent volume of distribution at steady state |
| $V_{max}$ | Amout/time | Maximum metabolic rate of $CL_{RANKL}$ |
| $V_t$ | Volume/kg | Apparent volume of the peripheral compartment in a two-compartment model |

Example 1

Toxicology Studies with ALX-0141

In a single dose toxicity study ALX-0141 was administered to male and female cynomolgus monkeys as single s.c. doses of 0, 0.02, 2, 20, and 50 mg/kg b.w ALX-0141 and a single i.v. bolus dose of 20 mg/kg. The sequence of ALX-0141 is depicted as SEQ ID NO: 12 (SEQ ID NO: 759 in US 2010/0104568).

Blood samples for pharmacokinetic (PK), anti-drug antibody (ADA), and pharmacodynamic (PD) analysis purposes were collected from all animals at pre-dose and at selected time points post-dose. Samples were analysed for PK, PD and ADA purposes using validated methods, with the exception of the CTX-1 determinations where a human commercial kit was used that was verified to be cross-reactive with cynomolgus monkey CTX-1.

In a repeated dose toxicity study, ALX-0141 was administered to male and female cynomolgus monkeys as s.c. doses of 0, 0.2, 2, 20, and 50 mg/kg b.w ALX-0141 at 6 occasions during 2 weeks (test days 1, 3, 5, 8, 10, and 12).

Toxicokinetic samples were taken up to study day 15 (i.e. 14 days after the first dose administration). Three groups (0, 2 and 50 mg/kg) included a recovery period, where additional 2 animals per sex were treated and sampling was performed over 99 days (i.e. up to 98 days post-dose).

Blood samples for PK, ADA, and PD purposes were collected from all animals at pre-dose and at selected time points post-dose. Samples were analyzed for PK, PD and ADA purposes using validated methods with the exception of the CTX-1 determinations where a human commercial kit was used, which was shown to be cross-reactive with cynomolgus monkey CTX-1.

Example 2

Preclinical Data

Pharmacokinetic (PK) and pharmacodynamic (PD) modeling was performed on data generated in a single dose toxicity study with ALX-0141 in the cynomolgus monkey as described in Example 1. Data from a 2-week repeated dose toxicity study were used to verify whether the single dose data could accurately predict the repeated dose pharmacokinetics (i.e. to verify time-dependency of ALX-0141 PK). Pharmacokinetic Modeling of Cynomolgus Monkey ALX-0141 Plasma Concentrations The non-linear pharmacokinetic behavior of ALX-0141 in the cynomolgus monkey was captured by fitting the data to an open two-compartmental pharmacokinetic model with linear and a non-linear clearance from the central compartment and first order absorption (s.c. application). The structural model is depicted in FIG. 1.

The linear clearance mechanism is likely related to the non-saturable, and non-RANKL mediated removal of ALX-0141 and corresponds to the slow and non-specific proteolytic degradation of ALX-0141. The non-linear and RANKL-mediated clearance process is a saturable clearance mechanism; most probably representing binding of ALX-0141 to membrane bound RANKL and subsequent internalization and clearance.

All available individual plasma concentration data after a single s.c. and i.v. dose with ALX-0141 were fitted simultaneously to the model (WinNonlin Professional Software Version 5.1 (Pharsight Corporation, Mountain View Calif., USA) using iterative re-weighting $(1/\hat{y}*\hat{y})$, where $\hat{y}$ is the predicted plasma concentration.

The estimated PK parameters of ALX-0141 in the cynomolgus monkey were estimated with sufficient precision and are listed in Table B-1.

An open two-compartmental pharmacokinetic model with parallel linear non RANKL-mediated clearance ($CL_{NON-RANKL}$) and non-linear saturable RANKL-mediated clearance ($CL_{RANKL}$) from the central compartment and first order absorption (s.c. application) was used to adequately describe the non-linear PK of ALX-0141 in the cynomolgus monkey.

At low ALX-0141 concentrations (C<<<$K_m$) the contribution of the $CL_{RANKL}$ Predominates, whereas at higher, RANKL-saturating plasma concentrations, the overall CL is mainly governed by the $CL_{NON-RANKL}$.

The estimated values of $CL_{RANKL}$ and $CL_{NON-RANKL}$ indicate that clearance via the RANKL-mediated component occurs more efficiently (about 5.6-fold) as compared to the non-RANKL-mediated pathway. The RANKL-mediated clearance is however readily saturated as indicated by the low $K_m$-value (0.149 µg/mL; 3.6 nM) of the $CL_{RANKL}$ pathway.

The estimated volume of distribution at steady-state suggests that ALX-0141 distributes outside the central compartment into the interstitial space of the tissues.

At ALX-0141 concentrations which saturate the RANKL-mediated pathway, the estimated half-life of ALX-0141 was 8.5 days, i.e. similar to that reported for cynomolgus monkey serum albumin.

The prominent role of the non-linear RANKL-mediated component of ALX-0141 in overall clearance explains the more than dose-proportional increase in exposure ($C_{max}$- and AUC-values) at the lower dose levels. At higher dose levels exposures increase dose-proportionally since the overall clearance is then mainly dictated by the linear non-RANKL mediated pathway.

ALX-0141 displayed time-independent pharmacokinetics since repeated dose pharmacokinetics could be adequately predicted on the basis of single dose data. In the monkey, the (single dose) s.c. absolute bioavailability of ALX-0141 was virtually complete (96%).

Semi-Mechanistic PK/PD Modeling (Cynomolgus Monkey ALX-0141 Plasma Concentrations and Serum CTX-1 Concentrations)

The effect of ALX-0141 administration on serum CTX-1 levels is considered indirect in nature since there is no direct relationship between achieved ALX-0141 plasma concentrations and effect on CTX-1 levels. Therefore, an indirect response model was employed to describe the pharmacological effect of i.v. and s.c. administered ALX-0141 on the physiological turnover of serum CTX-1.

The model is analogous to that previously employed for the anti-RANKL monoclonal antibody denosumab (Peterson M., Stouch B., Chen D. et al. 2004, A PK/PD Model Developed in cynomolgus Monkeys Predicts Concentrations and Effects of AMG 162, A Fully Human Monoclonal Antibody Against RANKL, in Healthy Postmenopausal Women. AAPS Annual Meeting, Baltimore, Md., Nov. 7-11, 2004; Abstract) and describes a drug response that results from the inhibition of the production of serum CTX-1. In this indirect response model, the rate of change of CTX-1 (Response, R) is described by:

$$\frac{dR}{dt} = k_{in} \cdot \left[1 - \frac{I_{max} \cdot C^n}{IC_{50}^n + C^n}\right] - k_{out} \cdot R$$

With $k_{in}$, the zero-order synthesis rate; R, the serum CTX-1 level, $I_{max}$, the maximum inhibition (1<$I_{max}$<0); C, the concentration of ALX-0141; n, the concentration-response shape factor; and $k_{out}$, the first order elimination rate constant of serum CTX-1.

All available individual serum CTX-1 data obtained after a single i.v. and s.c. dose were fitted simultaneously to the model (WinNonlin Professional Software Version 5.1, Pharsight Corporation, Mountain View Calif., USA) using the pharmacokinetic function as input function for the indirect response PK/PD model.

The pharmacodynamic effect of i.v. and s.c. administered ALX-0141 on the physiological turnover of serum CTX-1 in the monkey were adequately captured using a semi-mechanistic PK/PD model (indirect response model).

PK/PD modeling indicated that ALX-0141 was a potent inhibitor of serum CTX-1 production in the cynomolgus monkey ($IC_{50}$ of ca 22 ng/mL or 0.54 nM). In addition, ALX-0141 was able to almost completely inhibit the production of serum CTX-1 ($I_{max}$≈73%).

Example 3

Scaling to Human: Simulation of ALX-0141 PK/PD in Humans

The PK/PD model developed to describe the temporal profile of ALX-0141 concentrations and corresponding serum CTX-1 levels in the cynomolgus monkey was scaled to human to assist in the dose selection of the first in human study. A similar approach was previously successfully employed to simulate the human PK/PD of denosumab based on cynomolgus monkey data. (Peterson M., Stouch B., Chen D. et al. 2004, A PK/PD Model Developed in cynomolgus Monkeys Predicts Concentrations and Effects of AMG 162, A Fully Human Monoclonal Antibody Against RANKL, in Healthy Postmenopausal Women. AAPS Annual Meeting, Baltimore, Md., Nov. 7-11, 2004; Abstract).

To this end, the estimated $CL_{NON-RANKL}$/volumes of distribution (Vc and Vt), and absorption rate constant (ka) in the cynomolgus monkey were scaled to human using standard allometric equations (Boxenbaum H. 1984, Interspecies Pharmacokinetic Scaling and the Evolutionary-Comparative Pardigm. Drug Metab. Rev. 15(5&6): 1071-1121). For the $CL_{RANKL}$, the $K_m$-value was assumed to be similar between the cynomolgus monkey and man, whereas the $V_{max}$-value in humans was considered to be one third of that in the cynomolgus monkey since the metabolic rate for bone turnover is 3-fold slower in humans (FDA. 1994, Guidelines for preclinical and clinical evaluation of agents used in the prevention or treatment of postmenopausal osteoporosis).

Since the bioavailability cannot be scaled, predictions were performed using two reasonable values of F, i.e. 0.8 and 1.0. The PK parameters used for the simulation of the ALX-0141 plasma concentration-time profiles are listed in Table B-2.

To simulate the temporal profile of ALX-0141 concentrations in humans after s.c. administration, the scaled up pharmacokinetic parameters were combined with the previously described open two-compartmental pharmacokinetic model with a parallel linear non-RANKL-mediated clearance ($CL_{NON-RANKL}$) and a non-linear RANKL-mediated clearance ($CL_{RANKL}$) from the central compartment and first order absorption (s.c. application).

The predicted human ALX-0141 concentrations were subsequently used as input function for the indirect PK/PD response model (inhibition of synthesis) to predict the temporal serum CTX-1 profile in humans.

The baseline value of serum CTX-1 (RO) and the first order elimination rate constant ($k_{out}$) were taken from the literature (Glover S. J., Garnero P., Naylor K., Rogers A. and Eastell R. 2008, Establishing a reference range for bone turnover markers in young, healthy women. Bone 42: 623-630; Holford N, Pillai G, Kaila N, Collins W, Roy S, Cremers S, Trechsel U, Bouisset F, Steimer J-L. June 2006, PKPD model for cathepsin K inhibition with balicatib and changes in bone turnover biomarkers, in particular NTx. PAGE (Population Approach Group Europe), Bruges (B), 14-16). The maximum effect value ($I_{max}$) and the ALX-0141 concentration were assumed to be similar between cynomolgus monkeys and humans, whereas the concentration corresponding to half of the maximum effect ($IC_{50}$) was taken six-fold lower in humans relative to monkey. The latter is related to the effective concentration being 3-fold lower in humans compared to monkey as a result of differences in metabolic rate for bone turnover (3-fold slower in humans compared to monkeys) (FDA 1994, Guidelines for preclinical and clinical evaluation of agents used in the prevention or treatment of postmenopausal osteoporosis), in combination with a 2-fold greater affinity of ALX-0141 for binding to human RANKL versus cynomolgus monkey RANKL.

In Table B-3, the PD parameters used for the simulation of the ALX-0141 serum CTX-1 concentration-time profiles are listed.

Simulated PD profiles indicated a dose-dependent suppression of serum CTX-1 after a single s.c. dose with ALX-0141, consistent with the indirect response model describing inhibition of serum CTX-1 synthesis. Per this model, the suppression of serum CTX-1 would dependent on the dose of ALX-0141. The maximum degree of serum CTX-1 inhibition would increase with the administered dose up to its maximum effect ($I_{max}$)-value; a further increase in dose was not expected to further increase the effect but would prolong the time to return to baseline.

Example 4

Clinical Data 4.1 Methodology 4.1.1 Design

A double-blind, placebo-controlled, single ascending dose phase I study was performed in 1 cohort of 2 healthy postmenopausal female subjects receiving a single subcutaneous (s.c.) dose of ALX-0141 at 0.003 mg/kg or placebo (1 verum and 1 placebo) and 5 cohorts of 8 healthy postmenopausal female subjects receiving a single s.c. doses of ALX-0141 at 0.01, 0.03, 0.1, 0.3 and 1 mg/kg or placebo (6 verum and 2 placebo for each cohort). The day of treatment was Day 1 for purposes of calculating sample timing.

Plasma samples were collected at pre-dose, at 8, 12, 24, 48, 72, 96, 120 and 144 hours post-dose, once on Days 14, 30, 60 and at follow-up (Day 90) and, if applicable, at additional monthly follow-up visits to quantify the levels of the drug and of the biomarker CTX-1.

4.1.2 Procedures and Assessments

| | |
|---|---|
| Screening and each follow up visit: | Clinical laboratory (including calcium [Ca] and intact-parathyroid hormone [PTH]), 25-hydroxy Vitamin D in serum, vital signs, physical examination (at screening and first follow-up visit only), weight, 12-lead electrocardiogram (ECG), blood sampling for immunogenicity, PK and PD (blood sampling for immunogenicity, and blood and urine sampling for PD only at follow-up visit[s]); |
| At eligibility screening only: | Medical history, height, drug and alcohol screen, hepatitis B surface antigen (HBsAg), anti-hepatitis C virus (HCV) and anti-human immunodeficiency virus 1/2 (HIV 1/2); |
| Repeated upon admission: | Clinical laboratory (including Ca and intact-PTH), 25-hydroxy Vitamin D, weight, drug and alcohol screen, vital signs and ECG; |
| Observation period: | One period in clinic from −65 h (Day −3) before up to 144 h after drug administration on Day 1 and ambulatory visits on Day 14 ± 2, 30 ± 2, 60 ± 5 and 90 ± 5 (follow-up) and additional follow-up visits if necessary*; |
| Blood sampling: | For PK of ALX-0141 in plasma: pre-dose and 8 h and 12 h post-dose on Day 1, once in the morning on Days 2-7 and once on Days 14 ± 2, 30 ± 2, 60 ± 5 and 90 ± 5 (follow-up) and additional follow-up visits if necessary*; For PD of procollagen type I amino-terminal propeptide (P1NP), cross-linking telopeptide of type 1 collagen (CTX-1), bone specific alkaline phosphatase (BAP) and tartrate-resistant acid phosphatase (TRACP5b) in serum: at screening, once in the mornings on Days −2, −1, pre-dose and 8 h and 12 h post-dose on Day 1, and once in the morning on Days 2, 3, 4, 5, 6, 7, 14 ± 2, 30 ± 2, 60 ± 5 and 90 ± 5 (follow-up) and additional follow-up visits if necessary*; |
| Urine sampling: | For PD of CTX-1 and N-terminal telopeptide of type 1 collagen (NTX-1) and creatinine (under fasted conditions) in urine: once on Days −2, −1, 1 (pre-dose), 2, 3, 4, 5, 6, 7, 14 ± 2, 30 ± 2, 60 ± 5 and 90 ± 5 (follow-up) and additional follow-up visits if necessary*; |

| | |
|---|---|
| Safety assessments: | Adverse events (AEs) and local tolerability: throughout the study; vital signs and 12-lead ECG: pre-dose and 3, 6, and 9 h post-dose on Day 1, once in the morning on Days 2-7 and once on Days 14 ± 2, 30 ± 2, 60 ± 5 and 90 ± 5 (follow-up) and additional follow-up visits if necessary*; clinical laboratory (including Ca and intact-PTH), 25-hydroxy Vitamin D, immunophenotyping of white blood cells (WBC) to differentiate between B- and T-lymphocytes: once on Days 1, 2, 4, 6, 14 ± 2, 30 ± 2, 60 ± 5 and 90 ± 5 (follow-up) and additional follow-up visits if necessary*. |

*a monthly additional follow-up visit was conducted if CTX-1 levels had not returned to 70% of baseline level on Day 90 and were repeated until CTX-1 levels were back to 70% of baseline. On Day 420 CTX-1 levels of all subjects had returned to at least 70% of baseline level, and no additional follow up visits were required for any of the subjects.

4.1.3 Subjects

A total of 42 subjects were enrolled in this study. All subjects were healthy post-menopausal female volunteers. The post-menopausal female population is an anticipated target population for the medication.

Main Criteria for Inclusion

Age: maximum of 80 years, inclusive

Body Mass Index (BMI): 18-36 kg/m², inclusive

Gender: females

Subjects: healthy post-menopausal female volunteers

Study Medication

1. Active substance: ALX-0141, a trimeric construct of 41 kD, having two Nanobody building blocks targeting RANKL linked with a Nanobody targeting human serum albumin (HSA).
   Activity: anti-RANKL (anti-receptor activator of NFκB ligand)
   Indication: bone loss
   Strength: 0.65 mg/mL (Cohort 1), 2.17 mg/mL (Cohort 2), 6.5 mg/mL (Cohort 3)
   :21.7 mg/mL (Cohort 4) and 65 mg/mL (Cohorts 5 and 6)
   Dosage form: s.c. injection
2. Placebo: Visually matching medication Criteria for Evaluation PK: plasma ALX-0141 concentrations, PK parameters PD: P1NP, CTX-1, BAP and TRACP5b concentrations in serum and creatinine, CTX-1 and NTX-1 concentrations in urine Safety: AEs, local tolerability, vital signs, 12-lead ECG, clinical laboratory, physical examination, immunogenicity, 25-hydroxy Vitamin D in serum, immunophenotyping of WBC 4.1.4 Analyses The PD effects of ALX-0141 were explored by measuring CTX-1, TRACP5b, P1NP and BAP concentrations in serum and NTX-1/creatinine concentration ratios in urine. CTX-1, TRACP5b and NTX-1 are involved in bone resorption, whereas P1NP and BAP are involved in bone formation. Biomarker assays used were:

| | |
|---|---|
| CTX-1 | Serum CROSSLAPS ® ELISA (cat. no. AC-02F1; Immunodiagnostic Systems Inc., Boldon, Tyne & Wear, UK) |
| NTX-1 | OSTEOMARK NTx Urine ELISA (cat. no. 9006; Inverness Medical (Wampole Laboratories), Princeton, NJ) |
| TRACP5b | BONETRAP ® Assay ELISA (cat. no. SB-TR201A; Immunodiagnostic Systems Inc., Boldon, Tyne & Wear, UK) |
| P1NP | UNIQ ™ P1NP RIA (cat. no. Q67034; Orion Diagnostica Oy, Espoo, Finland) |
| BAP | OSTASE ® BAP Immunoenzymetric Assay (cat. no. AC-20F1; Immunodiagnostic Systems Inc., Boldon, Tyne & Wear, UK) |
| Creatinine | creatinine test (cat. No. 03039070; Siemens Medical Solutions Diagnostics, Breda, Netherlands). |

4.1.5 Statistics

Plasma concentrations of ALX-0141 and serum CTX-1 levels were modeled by non linear mixed effects modeling using NONMEM. Inter-individual variability (IIV) was set on each structural parameter and was calculated as the square root of the variance for the respective parameter x100. An exponential error model (additive in the log scale) was assumed for residual variability. The estimation method used within NONMEM was the FOCEI.

Data from 31 human post-menopausal female volunteers were used for this population analysis.

4.2 Pharmacokinetics 4.2.1 Concentration Data in Plasma

Figure 3:
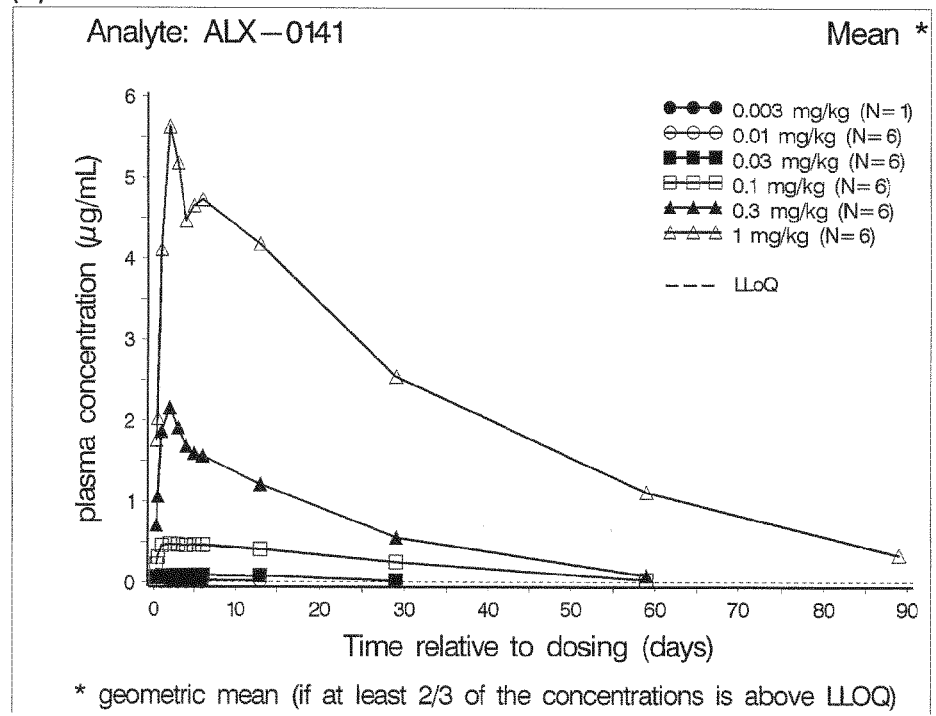
FIG. 3: Pharmacokinetics. Geometric mean plasma concentration versus time profiles of ALX-0141. (a) Linear scale; (b) Semi-logarithmic scale.
Figure 3:
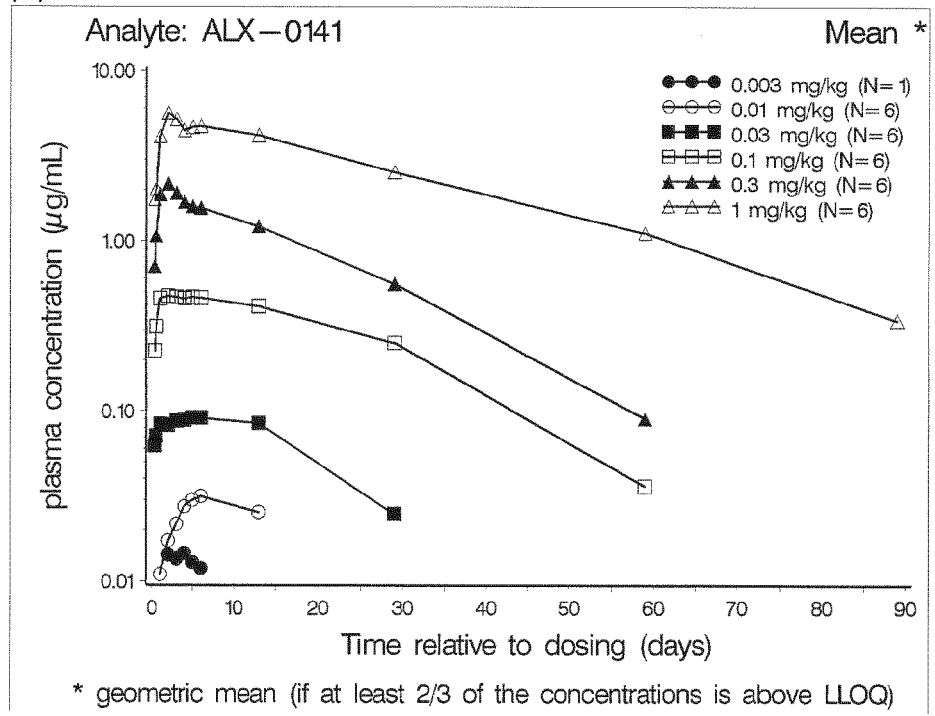

The drug concentration measurements of ALX-0141 were performed by a validated ELISA method. Geometric mean ALX-0141 plasma concentration-time profiles by treatment (linear and semi-logarithmic scale) are presented in FIG. 3.

Following s.c. administration of 0.003 mg/kg ALX-0141 (n=1), measurable plasma levels of ALX-0141 were observed from 48 h post-dose. On average, at the dose level of 0.01 mg/kg, ALX-0141 was measurable in plasma within 24 h. At dose levels of 0.03 mg/kg up to 1 mg/kg ALX-0141, ALX-0141 was measurable in plasma within 8 h. The geometric mean ALX-0141 plasma concentrations were found to increase gradually with maximum mean plasma concentrations being reached between 3 to 6 days post-dose at the dose levels ranging from 0.003 mg/kg to 0.03 mg/kg and between 1.5 to 2 days at the higher dose levels (0.1 mg/kg to 1 mg/kg). The mean plasma concentrations of ALX-0141 increased with increasing dose. After reaching the peak plasma concentration, mean plasma concentrations decreased very gradually. On average, at the highest dose levels, mean ALX-0141 plasma concentrations were still above LLOQ (0.0102 µg/mL) up to Day 60 (0.1 mg/kg and 0.3 mg/kg) or Day 90 (1 mg/kg). At the lower dose levels, ALX-0141 plasma concentrations were measurable up to Day 7 (0.003 mg/kg 1, n=1), Day 14 (0.01 mg/kg) or Day 30 (0.03 mg/kg).

4.2.1 Pharmacokinetic Parameters in Plasma

A summary of the ALX-0141 plasma PK parameters is presented in Table B-4.

The median $t_{max}$ ranged between 1.5 to 6 days post-dose and tended to be shorter (1.5 to 2 days) at the higher dose levels ranging from 0.1 mg/kg to 1 mg/kg compared to the lower dose levels ranging from 0.003 mg/kg to 0.03 mg/kg (3 to 6 days). The geometric mean half life could only be calculated reliably for the higher dosing groups (0.1 mg/kg, 0.3 mg/kg and 1 mg/kg ALX-0141) and was between 12.0 and 20.6 days. After a single s.c. dose administration of ALX-0141, the $C_{max}$, $AUC_{0-last}$ and $AUC_{0-inf}$ values increased with increasing doses. Over the dose range of 0.1 mg/kg up to 1 mg/kg, the $C_{max}$ and AUC values increased in a dose-proportional manner, whereas at the lower doses ranging from 0.01 mg/kg up to 0.1 mg/kg, it appeared that $C_{max}$ and $AUC_{0-last}$ increased somewhat more than dose-proportional.

4.2.3 Pharmacokinetic Analysis

Figure 2:
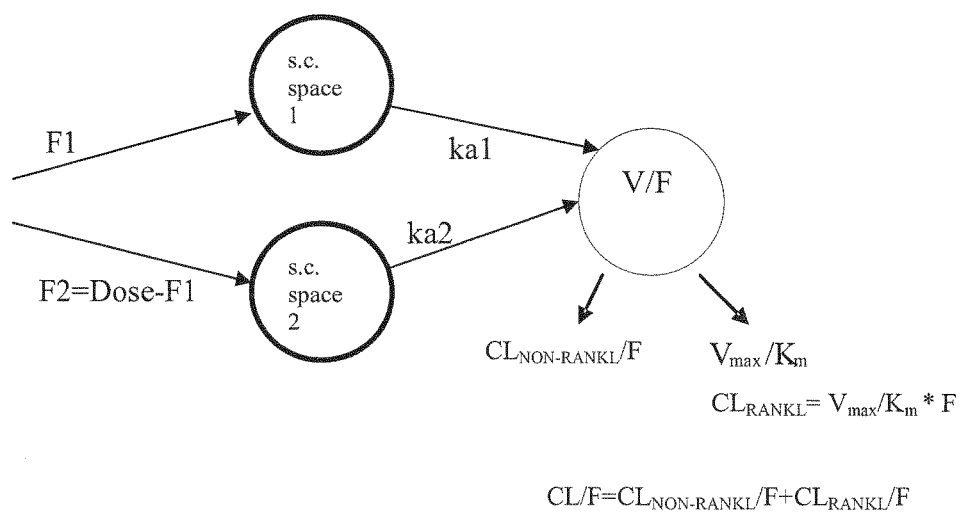
FIG. 2: Open mono-compartmental pharmacokinetic model with parallel first order absorption from the s.c. space and linear and non-linear clearance from the central compartment. $CL_{NON-RANK}/F$ is the linear non-RANKL mediated clearance corrected for s.c. bioavailability, V/F the volume of the central compartment corrected for s.c. bioavailability, F1 is the faction of the dose absorbed with $k_{a1}$, F2 is the fraction of the dose absorbed with $k_{a2}$ with $k_{a1}$ and $k_2$ being the respective fast and slow first order absorption rate constants, and $CL_{RANKL}/F$ is the non-linear RANKL-mediated clearance corrected for s.c. bioavailability ($V_{max}$ the maximum metabolic rate and $K_m$ the ALX-0141 concentration corresponding to 50% of $V_{max}$).

In healthy post-menopausal women, the pharmacokinetics of ALX-0141 were adequately characterized by an open mono-compartmental model with two first order absorption rates from the subcutaneous compartment, and a linear (non-target related) and non-linear (target related) clearance from the central compartment. The structural model is depicted in FIG. 2 and the PK parameter estimates are listed in Table B-5.

The target-mediated is ca. 4-fold more efficient than the non-RANKL-mediated pathway, but is readily saturated.

Body weight was a determining covariate on the volume of distribution.

Overall all the structural parameters of the final PK model were estimated with good precision (25.2% or less). The inter-Individual variability (IIV) was low to moderate for V (22.2%) and for F1 (36.5%). A larger inter-individual variability was found for $k_{a1}$ and $k_{a2}$ (170 and 144% respectively), for CL (53%) and for $K_m$ (135%). The standard deviation for residual error was estimated to 0.11 with a good precision (13.7%).

4.3 Pharmacodynamics

The PD effects of ALX-0141 were explored by measuring the serum concentrations of CTX-1, TRACP5b, P1NP and BAP, and urine NTX-1/creatinine ratios, which are involved in bone resorption and/or bone formation. Mean serum concentrations of CTX-1, TRACP5b, P1NP and BAP expressed as percentage of baseline are presented in FIGS. 4 and 6 (CTX-1), FIG. 8 (TRACP5b), FIG. 9 (P1NP) and FIG. 10 (BAP). Mean urine NTX-1/creatinine concentration ratios are presented in FIGS. 5 and 7. A summary of PD parameters is presented in Table B-6.

4.3.1 CTX-1

Figure 4:
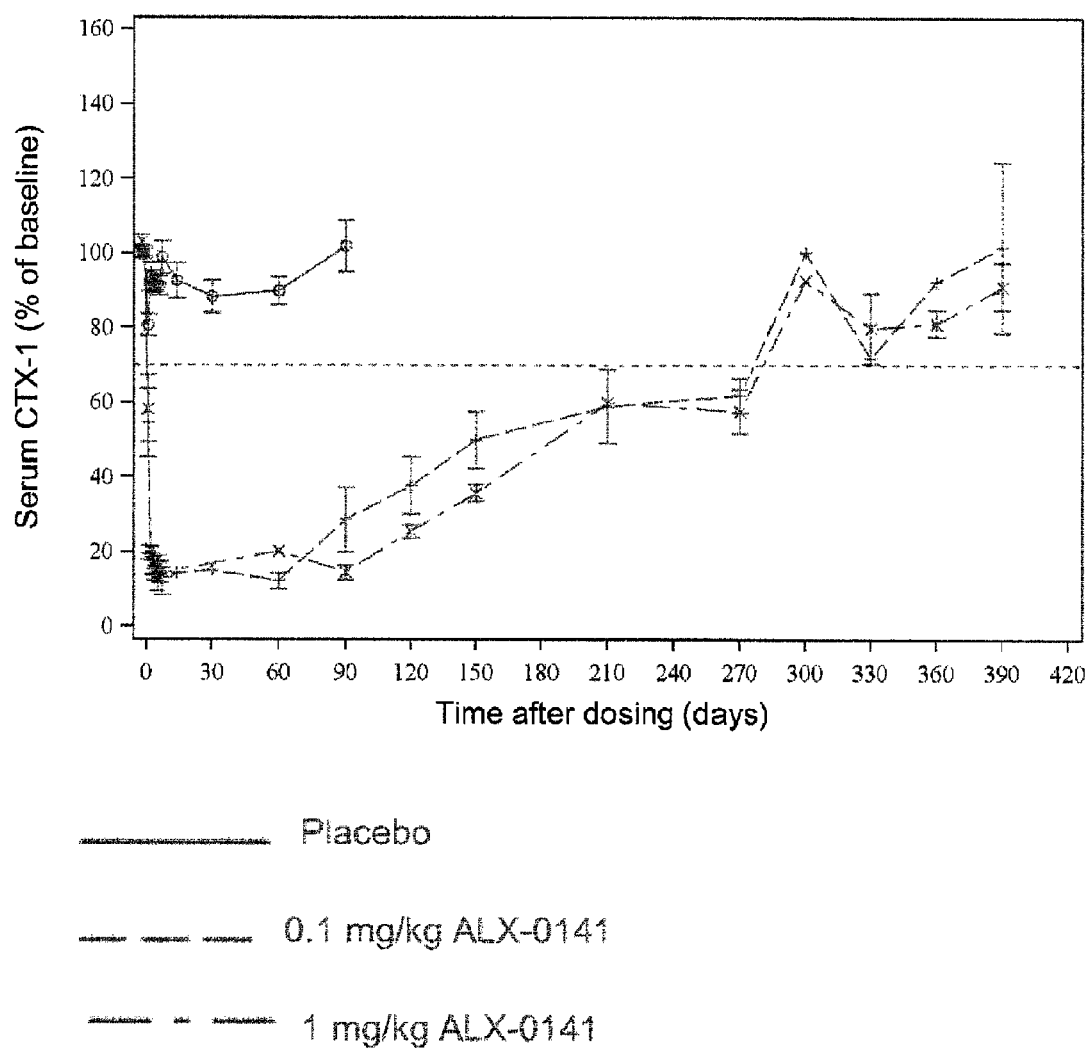
FIG. 4: Pharmacodynamics—changes in serum CTX-1. A rapid decrease in serum CTX-1 level was observed within 8 hours post-dose in ALX-0141 treated subjects. A dose-dependent, long-lasting inhibitory effect of ALX-0141 on serum CTX-1 level (% of baseline) is shown. Values are mean±SEM, n=11 for placebo, n=6 for each ALX-0141 treatment group.
Figure 6:
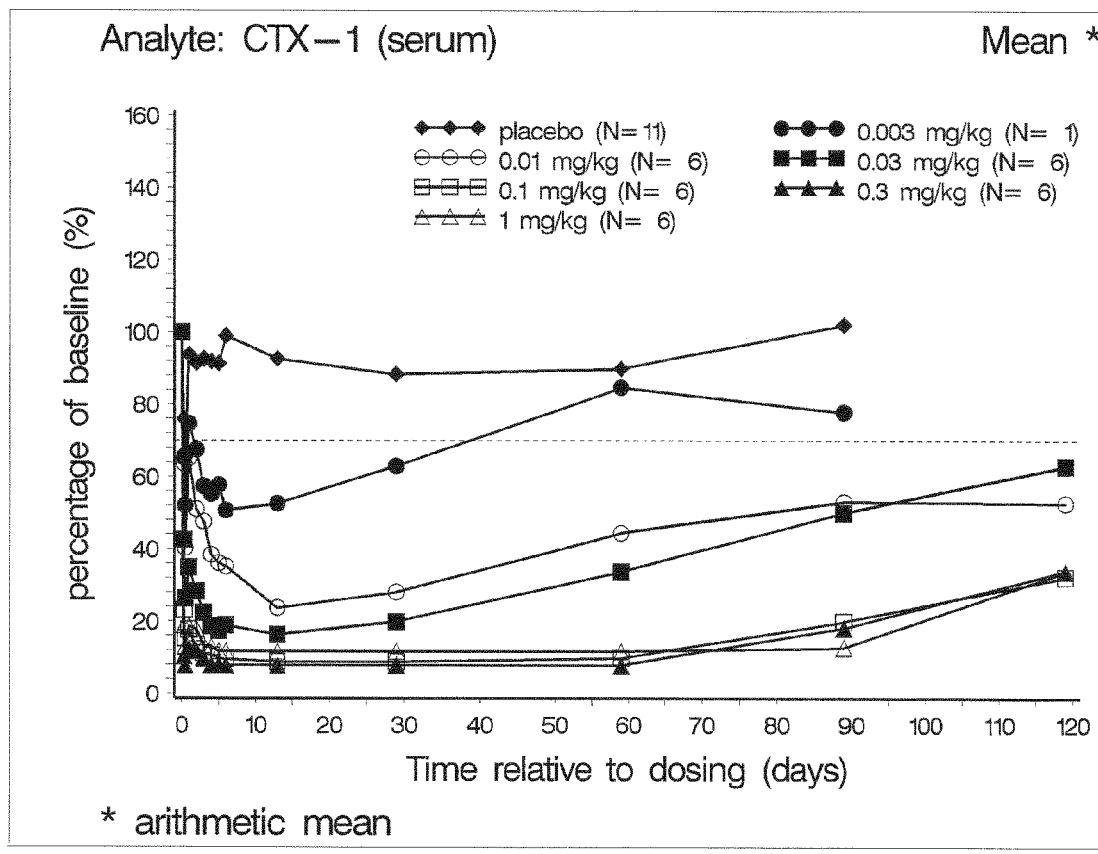
FIG. 6: Arithmetic mean CTX-1 serum concentration (% of baseline) after s.c. dosing with ALX-0141 or placebo in post-menopausal healthy female volunteers.

CTX-1 is a bone degradation product released as a result from osteoclast activity, and considered as a biomarker for bone resorption. Mean serum concentrations of CTX-1 (as % of baseline) after s.c. dosing with ALX-0141 or placebo in post-menopausal healthy female volunteers are shown in FIGS. 4 and 6. CTX-1 changes from baseline are shown in Table B-7.

After s.c. dosing with ALX-0141, a rapid decrease in CTX-1 was observed within 8 h post-dose (the first sampling time point) for all 6 dose levels tested. The mean nadir values for CTX-1 serum concentrations after treatment with ALX-0141 (active treatment) varied between 8.8% (0.3 mg/kg, N=6) and 50.7% (0.003 mg/kg, n=1) of baseline across the dose levels studied and decreased with increasing dose (FIG. 6). However, an almost maximum effect seemed to be reached at a dose level of 0.1 mg/kg or higher. In this study the dose level of 0.003 mg/kg can be considered as the BED. At the lowest 3 dose levels, the CTX-1 serum concentrations started to increase after a nadir had been reached and before Day 90, whereas at the highest 3 dose levels mean CTX-1 serum concentrations remained at a low level close to nadir up to Day 90 (0.1 mg/kg, 0.3 mg/kg, 1 mg/kg) and started to gradually increase thereafter. The ALX-0141 treated subject in Cohort 1 (0.003 mg/kg) showed a CTX-1 serum concentration close to baseline on Day 60, i.e. within the margin of baseline—30%. The mean CTX-1 values for the other ALX-0141 dose groups did not reach the 70% of baseline cut-off within the originally planned 90 days of follow-up. The low CTX-1 levels which persisted for more than 90 days in almost all ALX-0141-treated subjects and lasted for approximately 1 year in several subjects treated with 0.01 mg/kg or more, indicated a long-lasting PD effect upon a single s.c. ALX-0141 injection.

4.3.2 NTX-1

Figure 5:
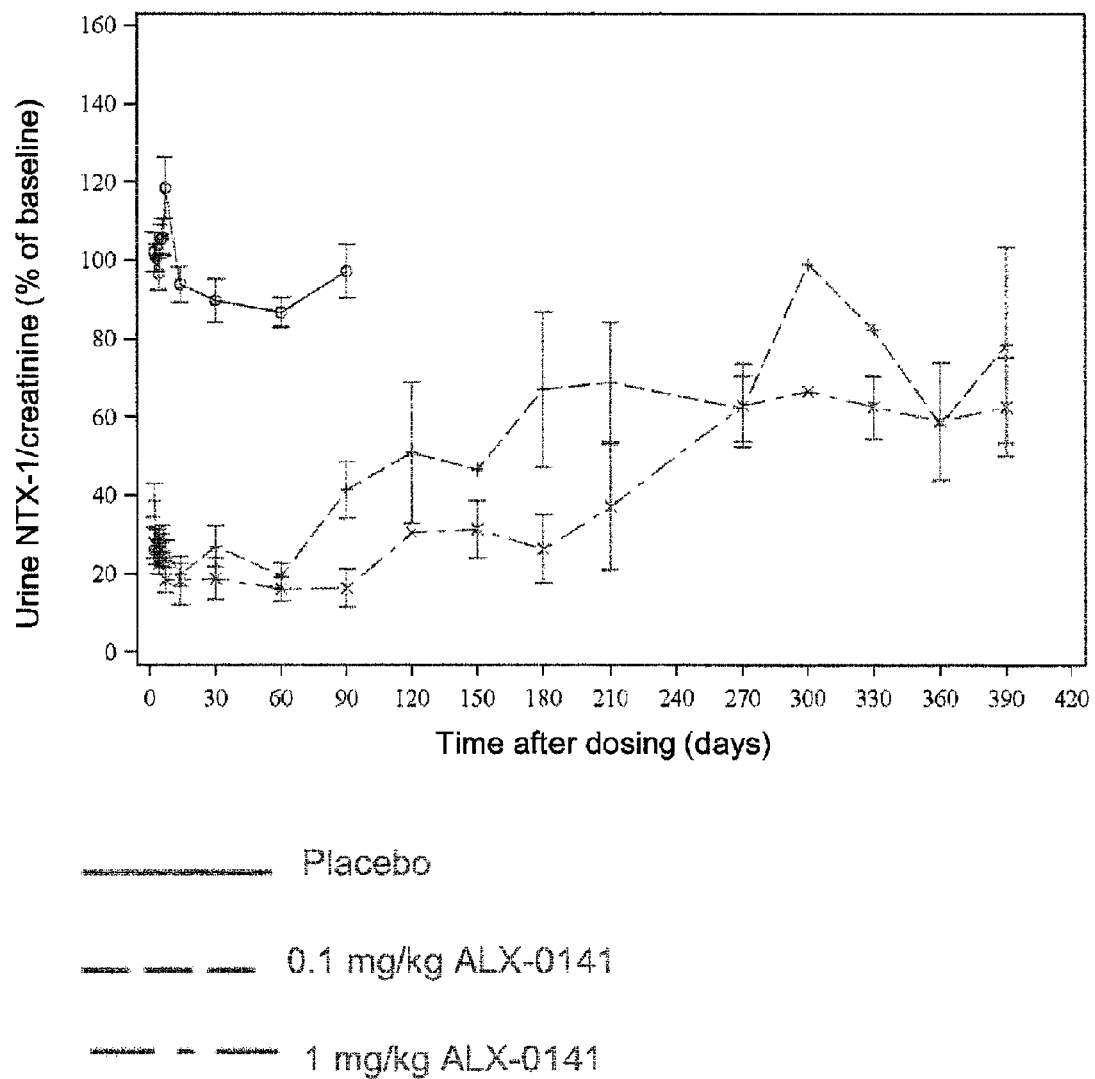
FIG. 5: Pharmacodynamics—changes in urine NTX-1/creatinine. A rapid decrease in urine NTX-1/creatinine level was observed within 8 hours post-dose in ALX-0141 treated subjects. A dose-dependent, long-lasting inhibitory effect of ALX-0141 on urine NTX-1/creatinine level (% of baseline) is shown. Values are mean±SEM, n=11 for placebo, n=6 for each ALX-0141 treatment group.
Figure 7:
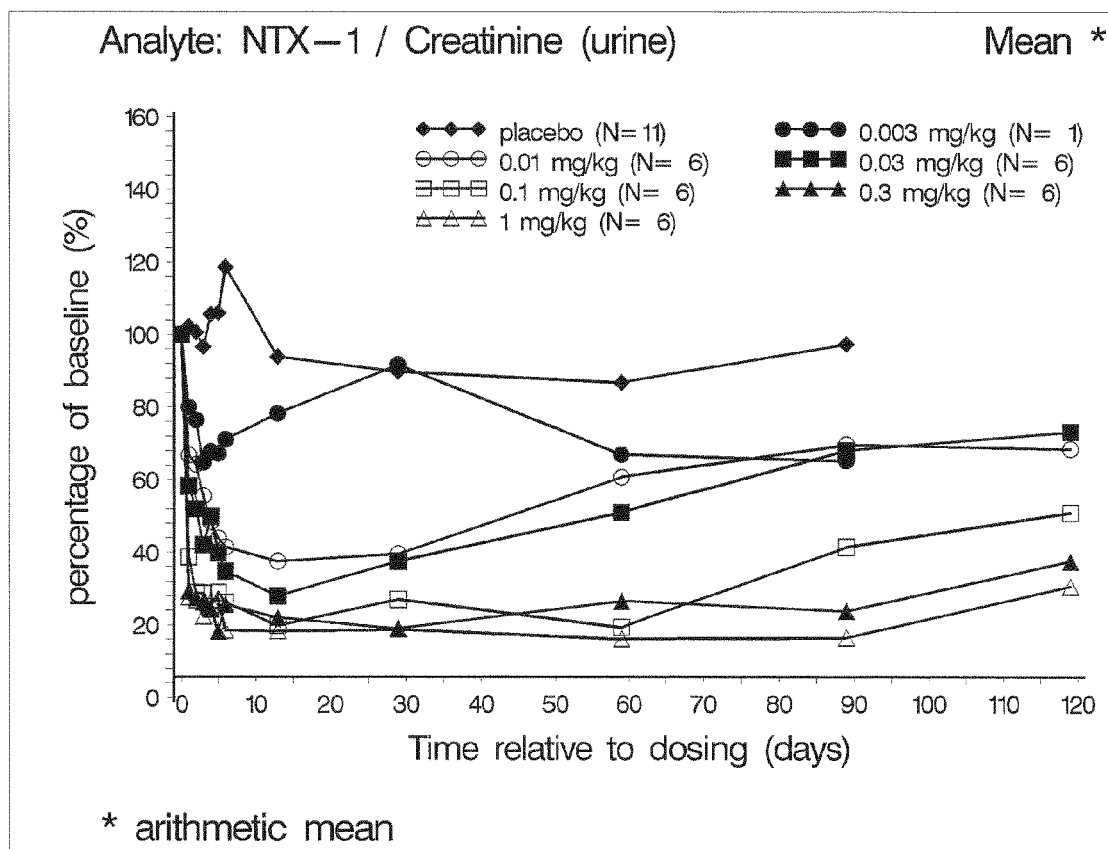
FIG. 7: Arithmetic mean NTX-1/Creatinine ratios in urine (% of baseline) after s.c. dosing with ALX-0141 or placebo in post menopausal healthy female volunteers.

NTX-1 is a degradation product of type I collagen, which is the organic major component of the extracellular matrix. Therefore NTX-1 is considered as a biomarker for bone resorption as a result of osteoclast activity. Since NTX-1 concentration in urine varies with urine volume, the ratio of NTX-1 to creatinine in urine was determined instead of the urine concentration of NTX-1, to correct for this variation. Mean urine NTX-1/creatinine concentration ratios (as % of baseline) after s.c. dosing with ALX-0141 or placebo in post-menopausal healthy female volunteers are shown in FIGS. 5 and 7. NTX-1/creatine ratio changes from baseline are shown in Table B-8.

Upon s.c. dosing with ALX-0141, a rapid decrease of NTX-1/creatinine concentration ratios was observed with a nadir on Day 4 (0.003 mg/kg, n=1), Day 6 (0.3 mg/kg, n=6), Day 14 (0.01 mg/kg [n=6] and 0.03 mg/kg [n=6]) and Day 60 (0.1 mg/kg [n=6] and 1 mg/kg [n=6]). The mean nadir values for urine NTX-1/creatinine ratios varied between 64.8% (0.003 mg/kg, n=1) and 16.1% (1 mg/kg, n=6) of baseline across the dose range studied and decreased with increasing doses. After treatment with 0.01 mg/kg and 0.03 mg/kg the mean NTX-1/creatinine concentration ratios remained low up to Day 30 and started to increase thereafter and were approximately 70% of baseline on Day 120. After treatment with 0.1 mg/kg, 0.3 mg/kg or 1 mg/kg the NTX-1/creatinine ratios in urine remained low up to Day 60 (0.1 mg/kg) or Day 90 (0.3 mg/kg and 1 mg/kg). Thereafter the NTX-1/creatinine levels started to increase again, but still remained far below baseline on Day 120. Twenty-two subjects had their NTX-1/creatinine ratios still below 80% of baseline at the time of their individual last follow-up. In the placebo-treated group, levels in NTX-1/creatinine ratios remained close to baseline (80-120%) throughout the period studied.

4.3.3 TRACP5b

Figure 8:
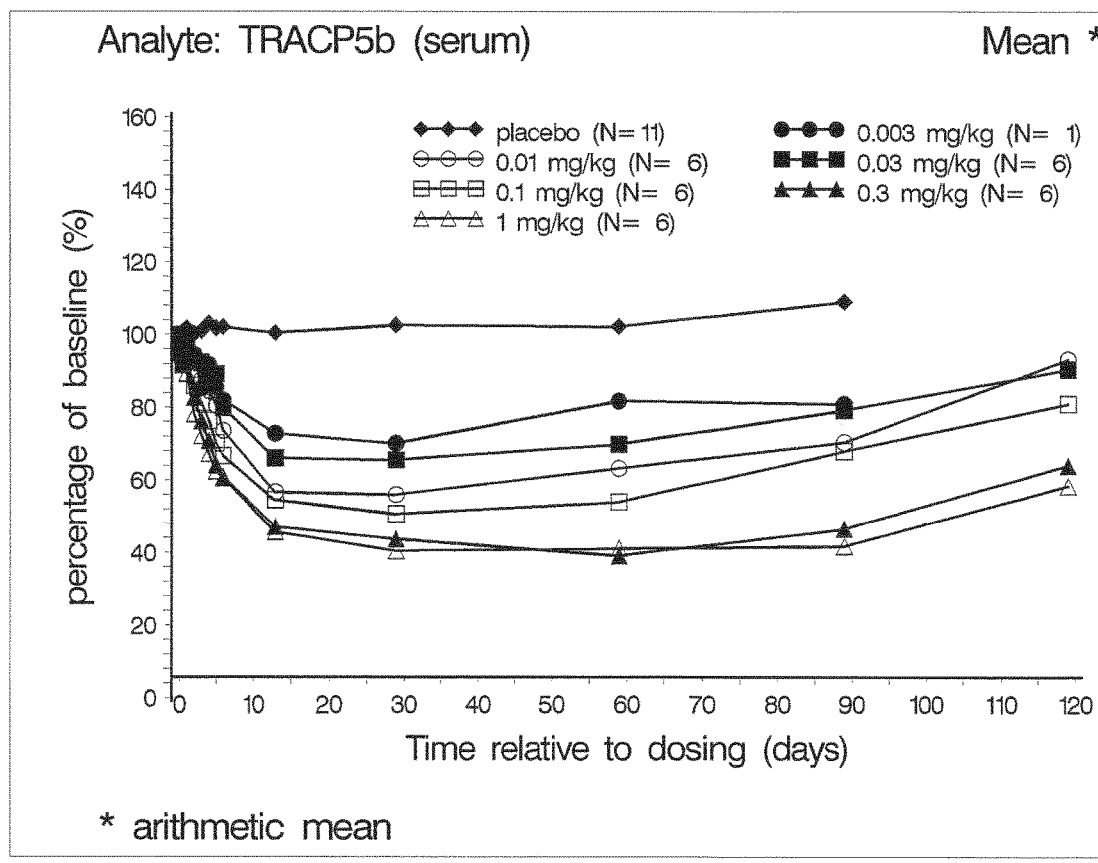
FIG. 8: Arithmetic mean TRACP5b serum concentration (% of baseline) after s.c. dosing with ALX-0141 or placebo in post-menopausal healthy female volunteers.

TRACP5b is an enzyme derived from osteoclasts and is a measure for osteoclast numbers, and therefore considered as a biomarker for bone resorption. Arithmetic mean serum concentration of TRACP5b (as percentage of baseline) after s.c. dosing with ALX-0141 or placebo in post-menopausal healthy female volunteers are shown in FIG. 8. TRACP5b serum concentrations showed a similar profile as CTX-1 serum levels.

Upon s.c. dosing with ALX-0141, the TRACP5b serum concentrations started to decrease within 2 to 4 days post-dose. An almost maximum effect was reached after approximately 14 days with a nadir reached on Day 30 (0.003 mg/kg, 0.01 mg/kg, 0.03 mg/kg, 0.1 mg/kg and 1 mg/kg) or on Day 60 (0.3 mg/kg). The mean nadir values for TRACP5b serum concentrations varied between 70.1% (0.003 mg/kg, n=1) and 39.1% (0.3 mg/kg, n=6) of baseline across the dose levels studied and decreased with increasing doses. Until Day 60 (0.003 mg/kg, 0.01 mg/kg, 0.03 mg/kg and 0.1 mg/kg) and Day 90 (0.3 mg/kg and 1 mg/kg), the TRACP5b serum concentrations hardly changed and were close to levels that were already reached on Day 14. Thereafter, the TRACP5b levels gradually increased and were back to at least 80% of baseline level at the time of last follow-up for all subjects (reason for using 80% is that within the placebo-treated subjects, lowest values hardly reach values below 80%; this indicates that decreases of 20% are within the normal variations over time). The strongest decrease in TRACP5b serum concentrations were reached with 0.3 mg/kg and 1 mg/kg ALX-0141. A decrease in TRACP5b levels was not observed in subjects treated with placebo. Although TRACP5b serum concentrations showed a similar profile compared to CTX-1 serum concentrations, based on comparison of individual TRACP5b and CTX-1 concentrations there was no indication that TRACP5b concentrations influenced directly the CTX-1 serum concentrations.

4.3.4 P1NP

Figure 9:
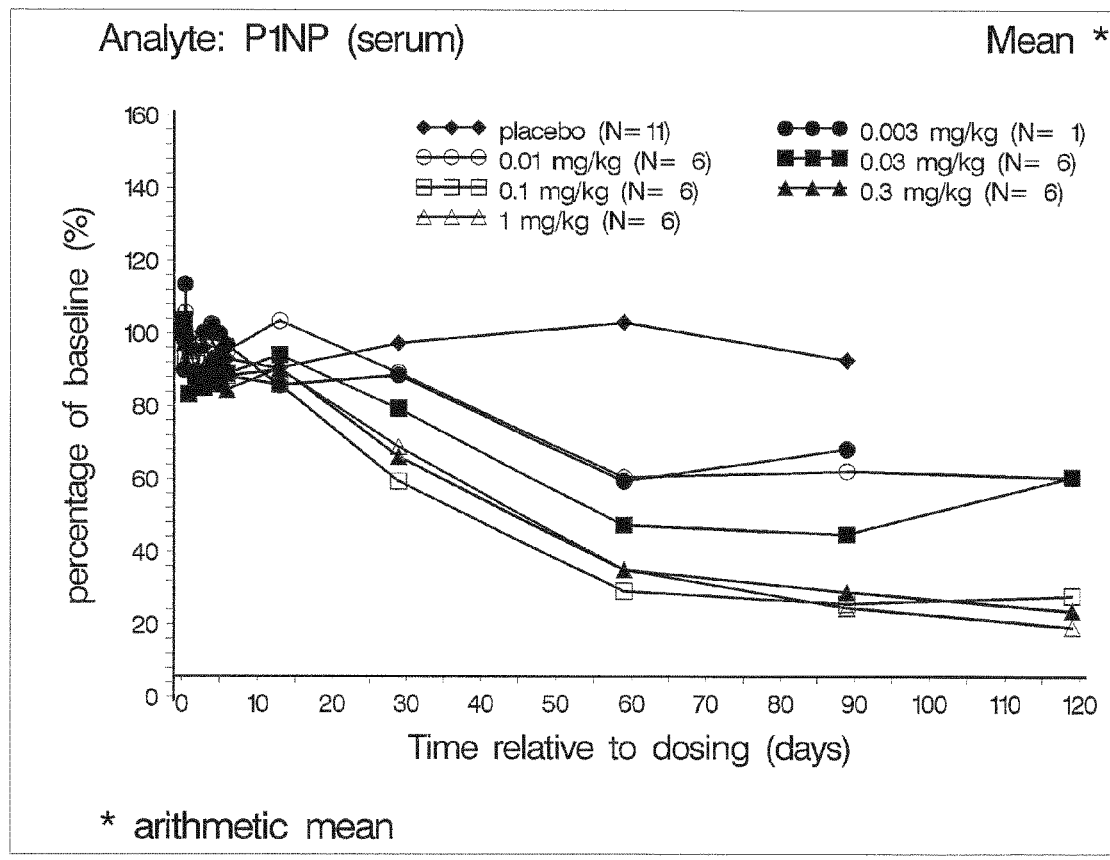
FIG. 9: Arithmetic mean P1NP serum concentration (% of baseline) after s.c. dosing with ALX-0141 or placebo in post-menopausal healthy female volunteers.

P1NP is released upon extracellular processing from newly synthesized pre procollagen prior to the incorporation of collagen into the bone and is considered as a biomarker for bone formation. Arithmetic mean serum concentration of P1NP (as percentage of baseline) after s.c. dosing with ALX-0141 or placebo in post-menopausal healthy female volunteers are shown in FIG. 9.

After s.c. administration of ALX-0141 the P1NP serum levels started to decrease between Day 14 and 30 onwards up to Day 60 across the dose range studied. Nadir values were reached between Day 60 and 150. In general, the higher the treatment dose, the stronger the decrease in P1NP plasma concentrations and the longer the period of decreased P1NP plasma concentrations. However, an almost maximum effect seemed to be reached at a dose level of 0.1 mg/kg ALX-0141. The mean nadir values for P1NP varied between 60.4% (0.01 mg/kg, n=6) and 21.2% (1 mg/kg, based on n=5) of baseline across the dose levels studied. Most subjects had their P1NP serum concentrations not returned to 80% of the baseline at their last follow-up visit (reason for using 80% is that within the placebo-treated subjects, lowest values hardly reach values below 80%; this indicates that decreases of ≤20% are within the normal variations over time). These data suggest that the effect on P1NP is strongly delayed compared to that on CTX-1 and TRACP5b. No effect on P1NP was observed in the placebo-treated subjects.

4.3.5 BAP

Figure 10:
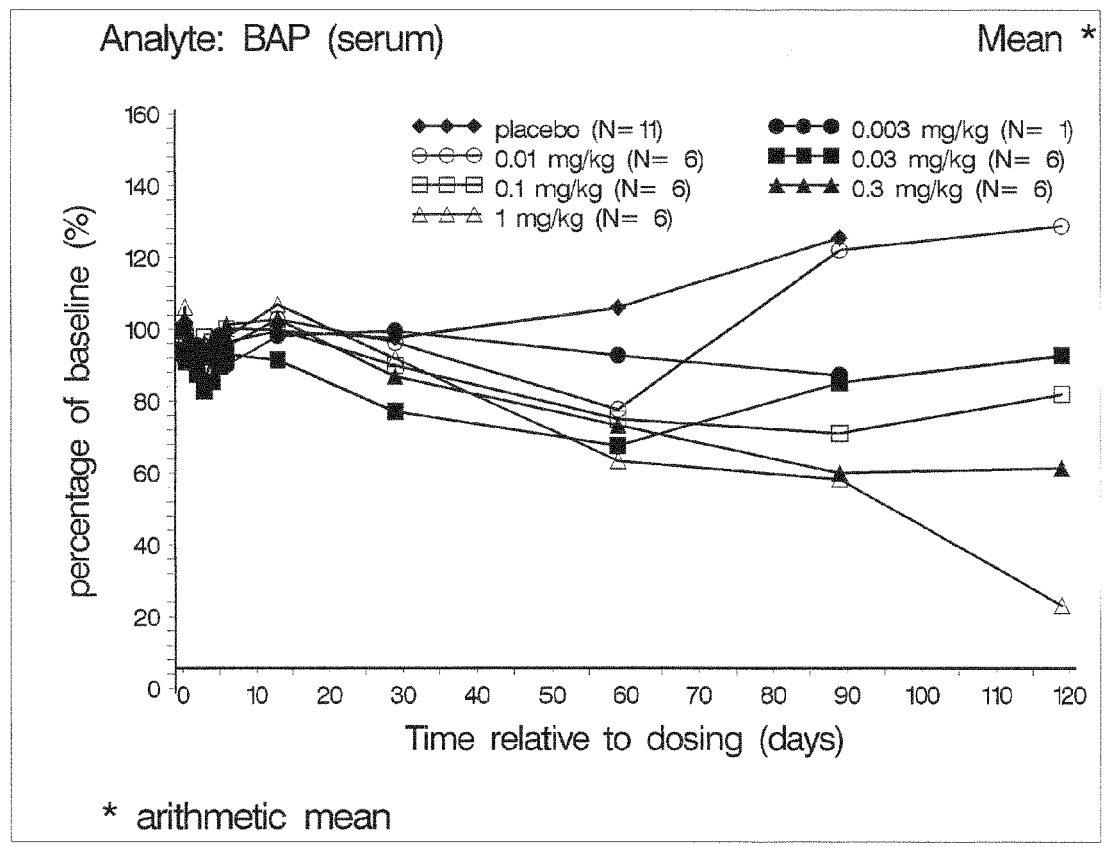
FIG. 10: Arithmetic mean BAP serum concentration (% of baseline) after s.c. dosing with ALX-0141 or placebo in post-menopausal healthy female volunteers.

BAP is an enzyme that serves as a biomarker for active bone formation. Arithmetic mean serum concentration of BAP (as percentage of baseline) after s.c. dosing with ALX-0141 or placebo in post-menopausal healthy female volunteers are shown in FIG. 10.

There was no clear change from baseline after treatment with 0.003 mg/kg ALX-0141 (n=1) and BAP serum concentrations tended to increase in placebo-treated subjects. After treatment with 0.01 mg/kg to 1 mg/kg ALX-0141, BAP serum concentrations tended to decrease from Day 30 onwards. This decrease in BAP serum levels was less pronounced than that of P1NP serum levels. A nadir was reached on Day 60 after treatment with 0.01 mg/kg and 0.03 mg/kg, and on Day 90 after treatment with 0.1 mg/kg, 0.3 mg/kg and 1 mg/kg. The mean nadir values for BAP varied between 85.3% (0.003 mg/kg, n=1) and 58.3% (1 mg/kg, n=6) of baseline across the dose range studied and decreased with increasing doses. After treatment with 0.01 mg/kg and 0.03 mg/kg ALX-0141, BAP serum concentrations tended to increase from Day 60 onwards, and were close to baseline levels on Day 90. After treatment with 0.1 mg/kg, 0.3 mg/kg and 1 mg/kg, BAP serum concentrations remained low (0.1 mg/kg and 0.3 mg/kg) or were still decreasing (1 mg/kg) on Day 120. The BAP serum concentrations at the last follow-up visits varied among the subjects, with most subjects showing BAP levels returned to at least 80% of baseline.

These data suggest that similar to P1NP, the effect on BAP is strongly delayed compared to that of CTX-1 and TRACP5b.

4.3.6 Conclusion

Single s.c. administrations of ALX-0141 at dose levels ranging from 0.003 mg/kg to 1 mg/kg resulted in a rapid decrease in CTX-1 and TRACP5b serum concentrations as well as in urine NTX-1/creatinine concentration ratios, which suggests a decrease in bone resorption. The inhibitory effect tended to be dose dependent and was long-lasting.

An (almost) maximal inhibitory effect appeared to be reached at 0.1 mg/kg ALX-0141 for CTX-1 and at 0.3 mg/kg ALX-0141 for TRACP5b serum concentrations and NTX-1/creatinine concentration ratios.

Single s.c. administrations of ALX-0141 at dose levels of 0.003 mg/kg to 1 mg/kg ALX-014 resulted in a gradual decrease in P1NP serum concentrations, which indicates a trend towards a decrease in bone formation. The inhibitory effect tended to be dose-dependent, with a nadir reached at approximately Day 90 to Day 150. A maximal inhibitory effect appeared to be reached at 0.3 mg/kg for P1NP serum concentrations.

Similar to the P1NP profile, but to a lesser extent, a trend towards a dose-dependent, gradual decrease in BAP serum concentrations seemed to occur upon the highest dose levels (0.1 mg/kg, 0.3 mg/kg and 1 mg/kg ALX-0141) tested.

Overall, the lowest dose administered (0.003 mg/kg) appeared to be biologically effective whereas the biological effect of 0.1 mg/kg seemed to be close to that of 0.3 mg/kg and 1 mg/kg. Therefore, the dose level of 0.003 mg/kg can be considered as the BED. In line with the expected effects of anti-resorptive agents, ALX-0141 exhibits a strong inhibitory effect on bone resorption markers and a modest effect in reduction of markers for bone formation.

4.3.7 Pharmacodynamic Analysis

An indirect PK/PD model of inhibition of the serum CTX-1 production captured the observed serum CTX-1 time profiles adequately.

In this indirect response model, the rate of change of CTX-1 (Response, R) is described by:

$$\frac{dR}{dt} = k_{in} \cdot \left[1 - \frac{I_{max} \cdot C^n}{IC_{50}^n + C^n}\right] - k_{out} \cdot R$$

With $k_{in}$, the zero-order synthesis rate; R, the serum CTX-1 level, $I_{max}$, the maximum inhibition ($1 < I_{max} < 0$); C, the concentration of ALX-0141; n, the concentration-response shape factor; and $k_{out}$, the first order elimination rate constant of serum CTX-1.

Overall all the structural parameters of the final PK/PD model were estimated with a precision of <88% (see Table B-9). The interindividual variability (IIV) was low to moderate for $I_{max}$ (6.4%), for baseline (22.1%) and for $k_{in}$ (46.4%). The residual variability was estimated to 32.1% with a good precision (12.1%).

ALX-0141 was determined to be a potent inhibitor of serum CTX-1 production, as evidence by its low $IC_{50}$-value of 0.674 ng/ml or 16.4 pM.

The dose level was identified as a determining covariate on the zero order production rate of the response (serum CTX-1).

The predictive performance of the models was confirmed by Visual Predictive Checks.

4.4 Discussion

Figure 11:
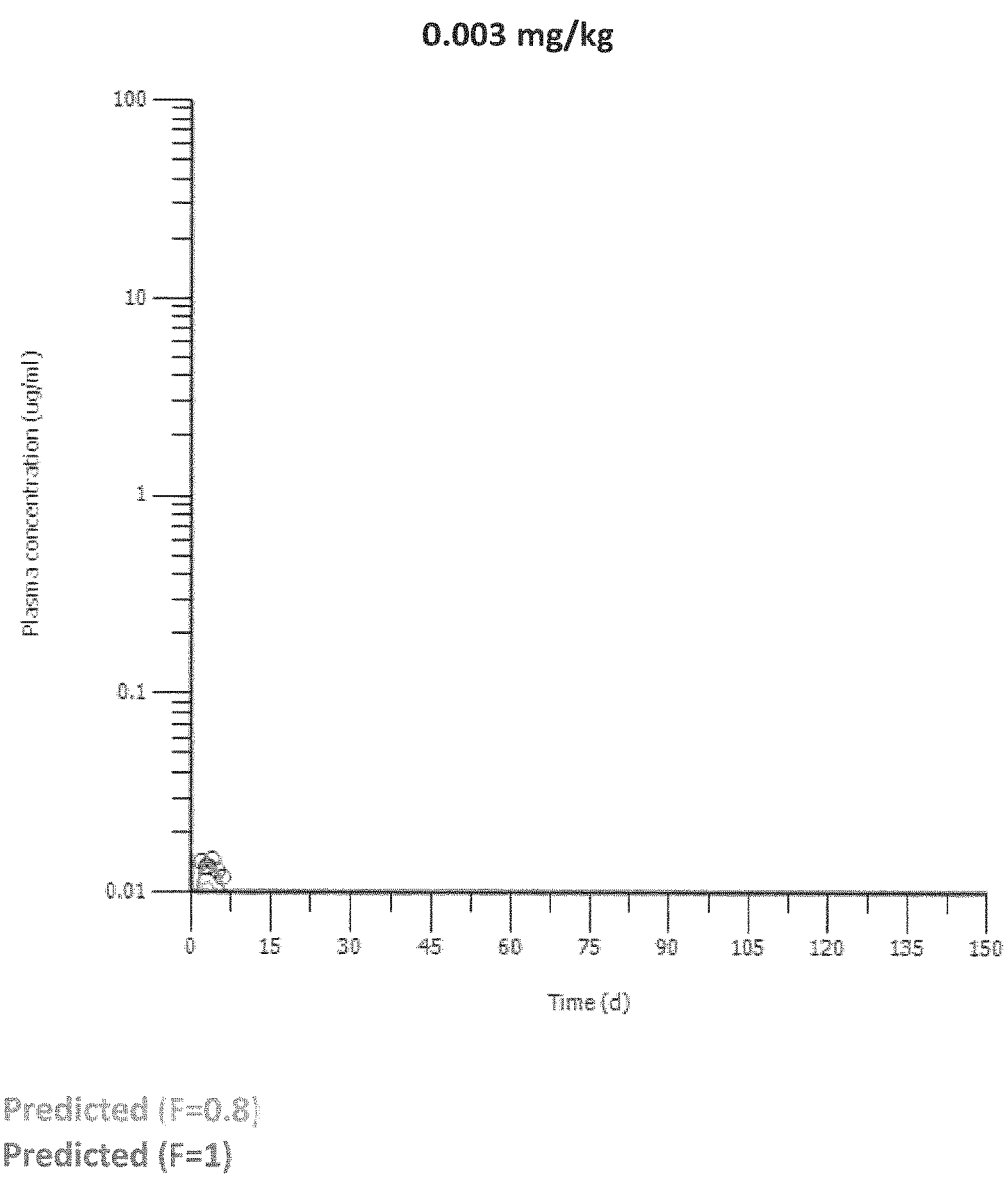
FIG. 11: Observed (lines with data points indicated) and model based simulations (lighter lines, no data points indicated) of ALX-0141 plasma concentration-time profiles in healthy post-menopausal women following a single s.c. dose with ALX-0141 at (a) 0.003, (b) 0.01, (c) 0.03, (d) 0.1, (e) 0.3, and (f) 1 mg/kg.
Figure 11:
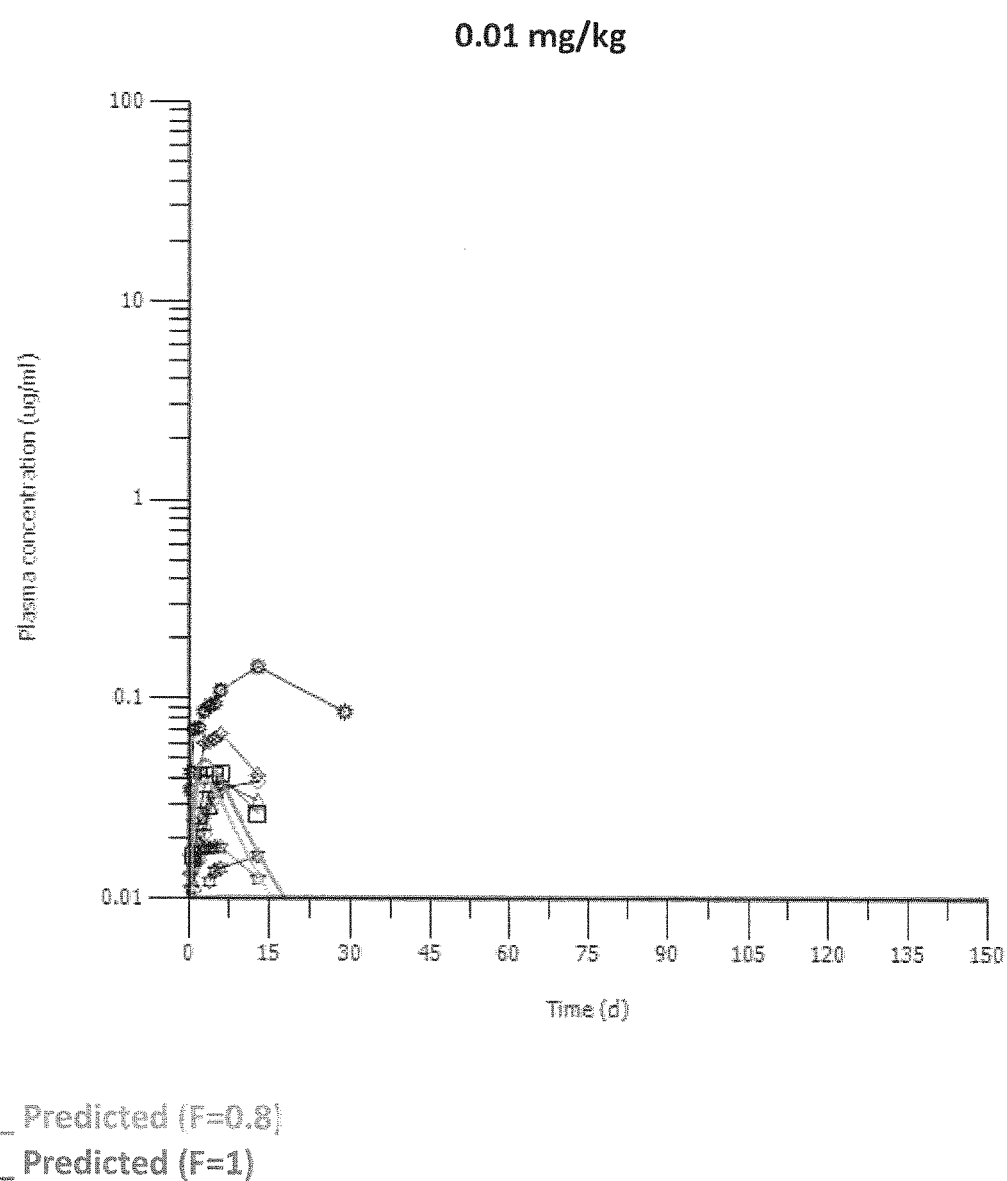
Figure 11:
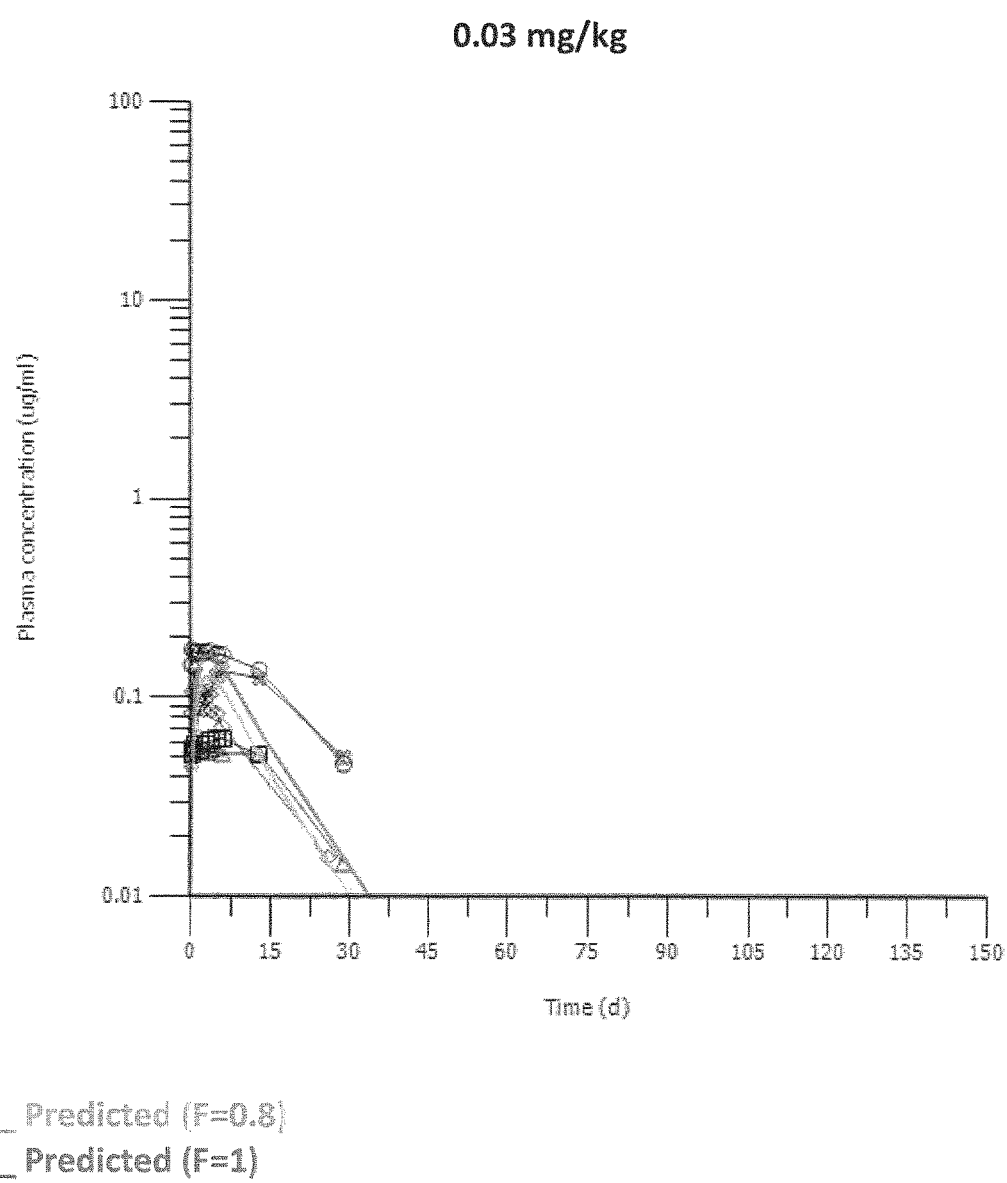
Figure 11:
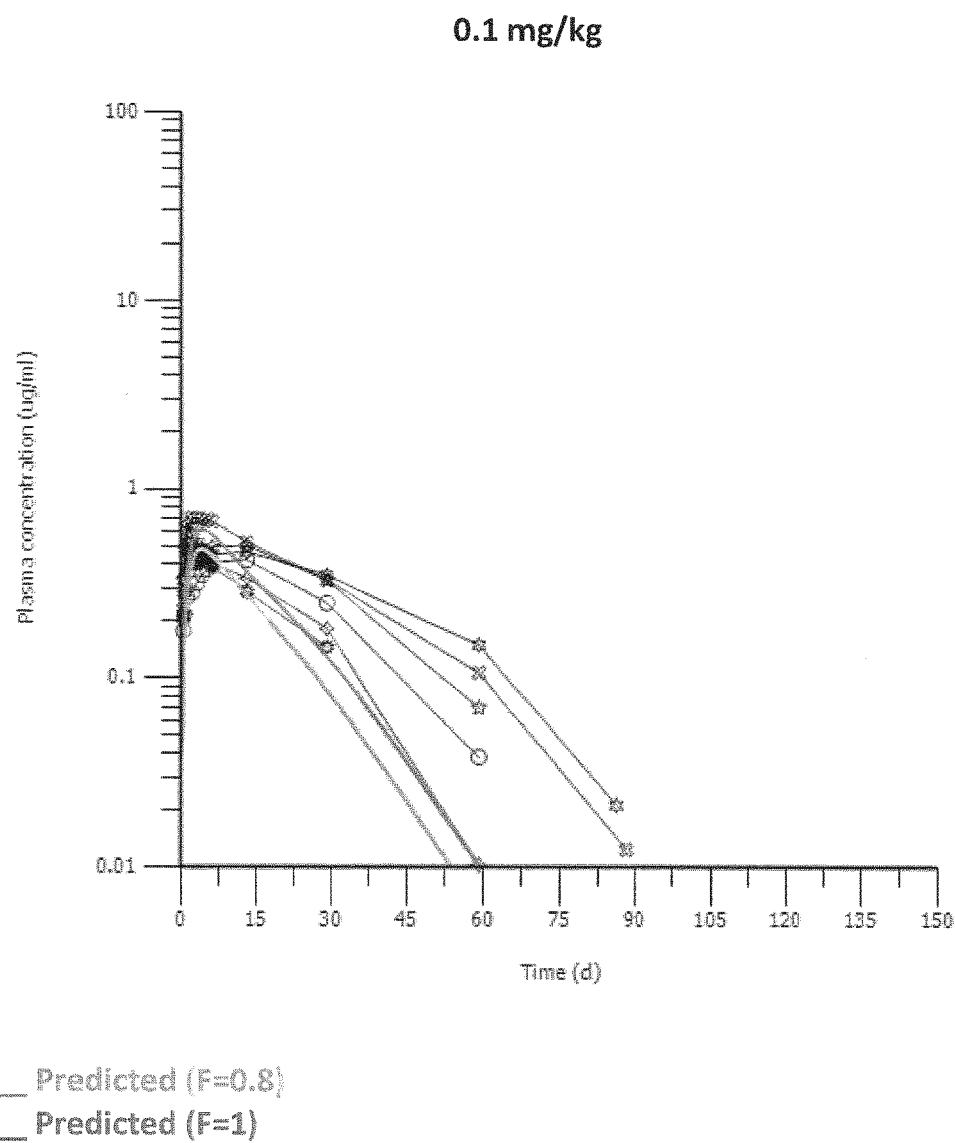
Figure 11:
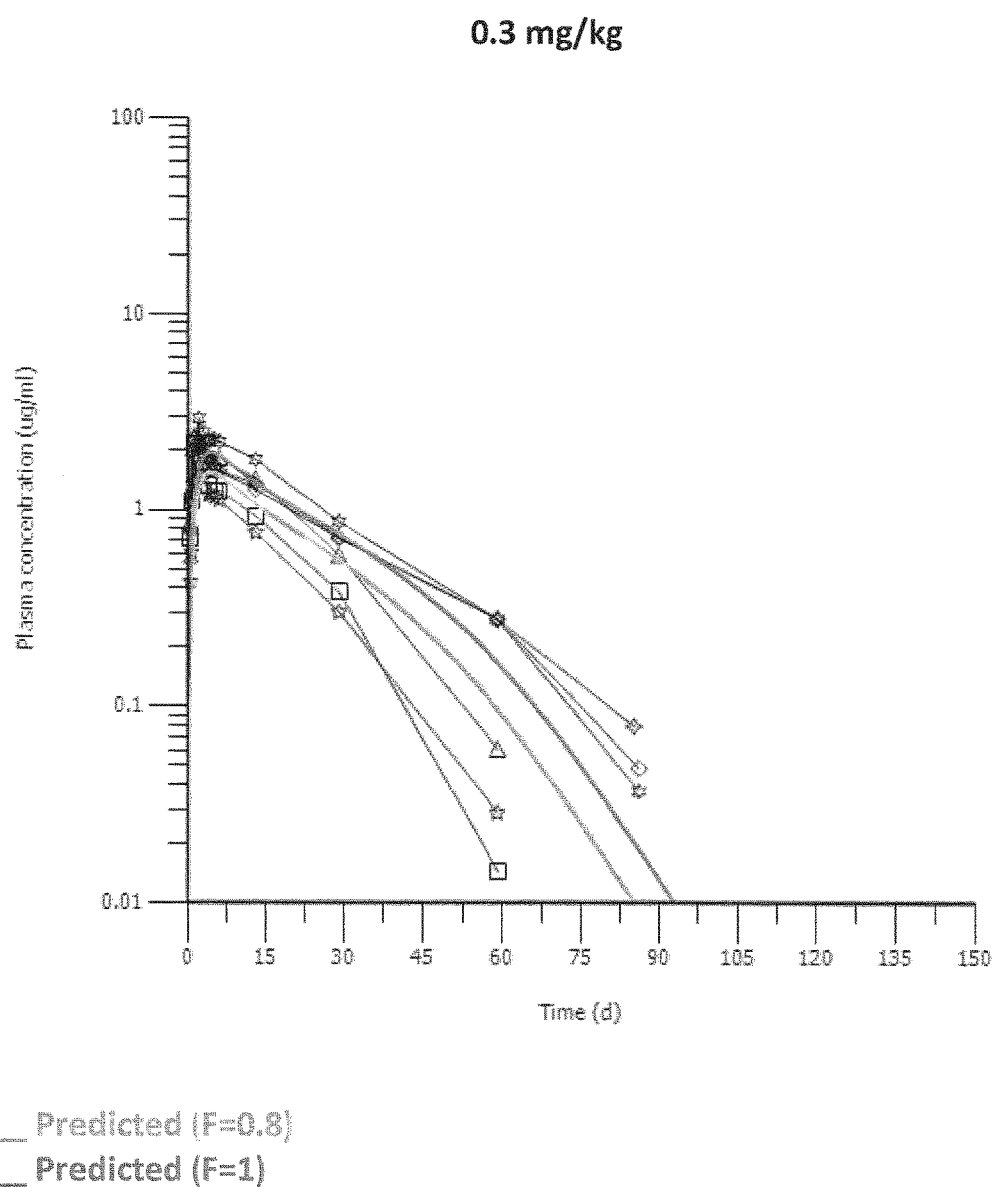
Figure 11:
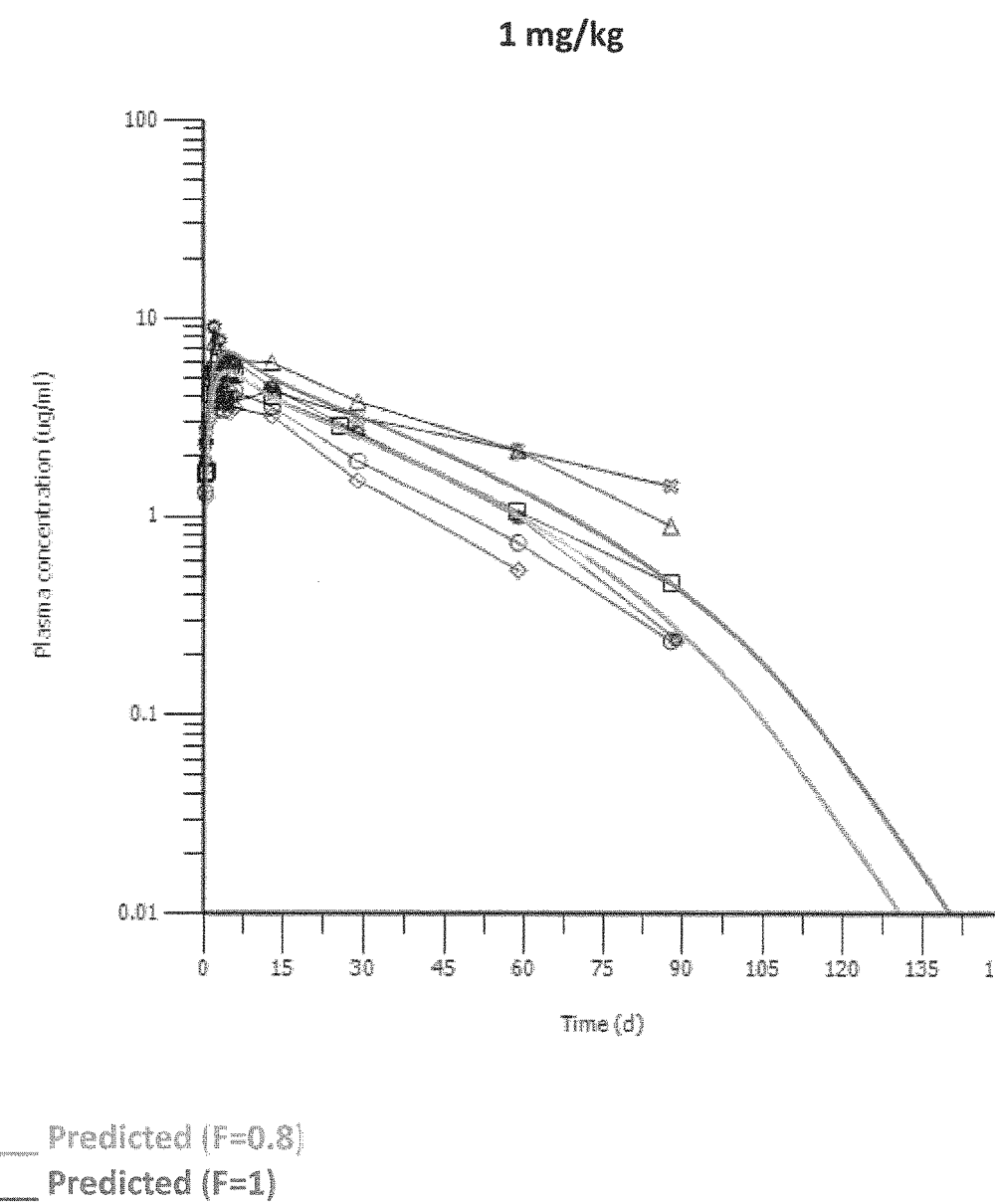

The clinical pharmacokinetics of ALX-0141 were fairly well predicted based on preclinical data from monkeys, allometrically scaled, and combined with reasonable assumptions regarding differences in bone remodelling (see FIG. 11).

Figure 12:
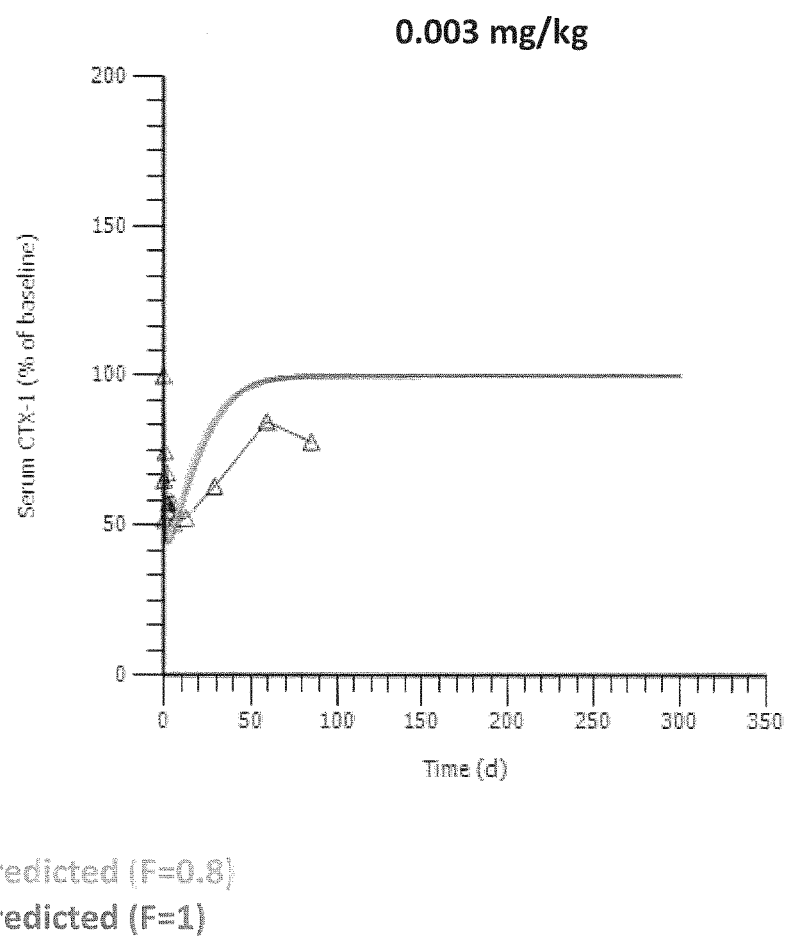
FIG. 12: Observed (lines with data points indicated) and model based simulations (lighter lines, no data points indicated) of serum CTX-1-time profiles in healthy post-menopausal women following a single s.c. dose with ALX-0141 at (a) 0.003, (b) 0.01, (c) 0.03, (d) 0.1, (e) 0.3, and (f) 1 mg/kg.
Figure 12:
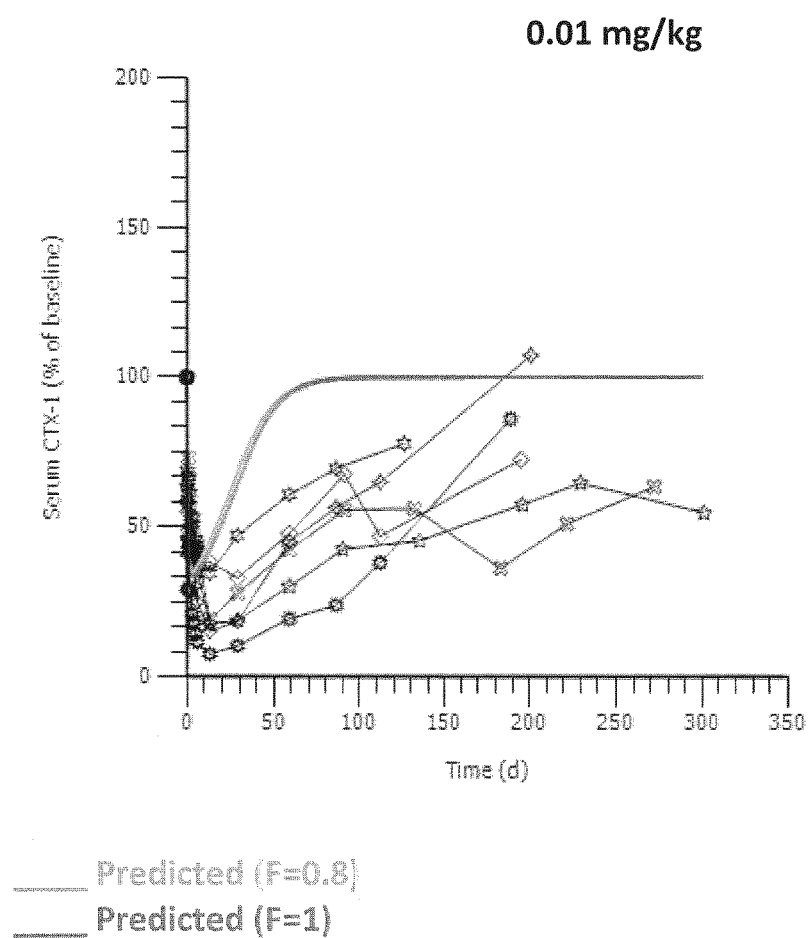
Figure 12:
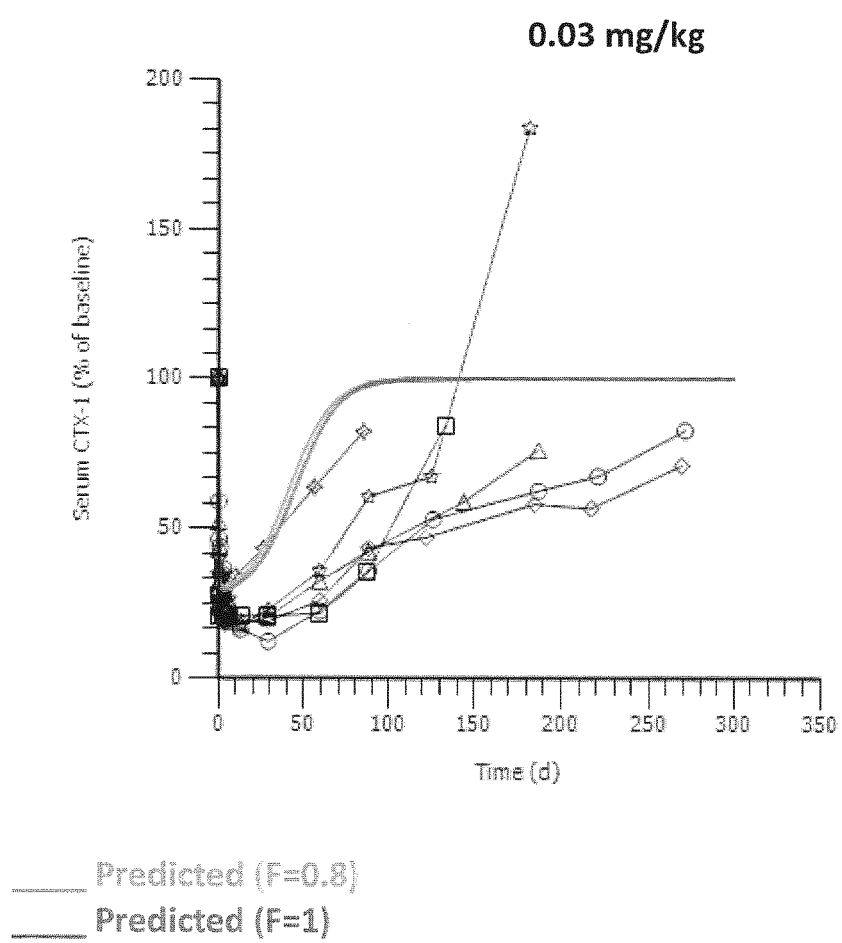
Figure 12:
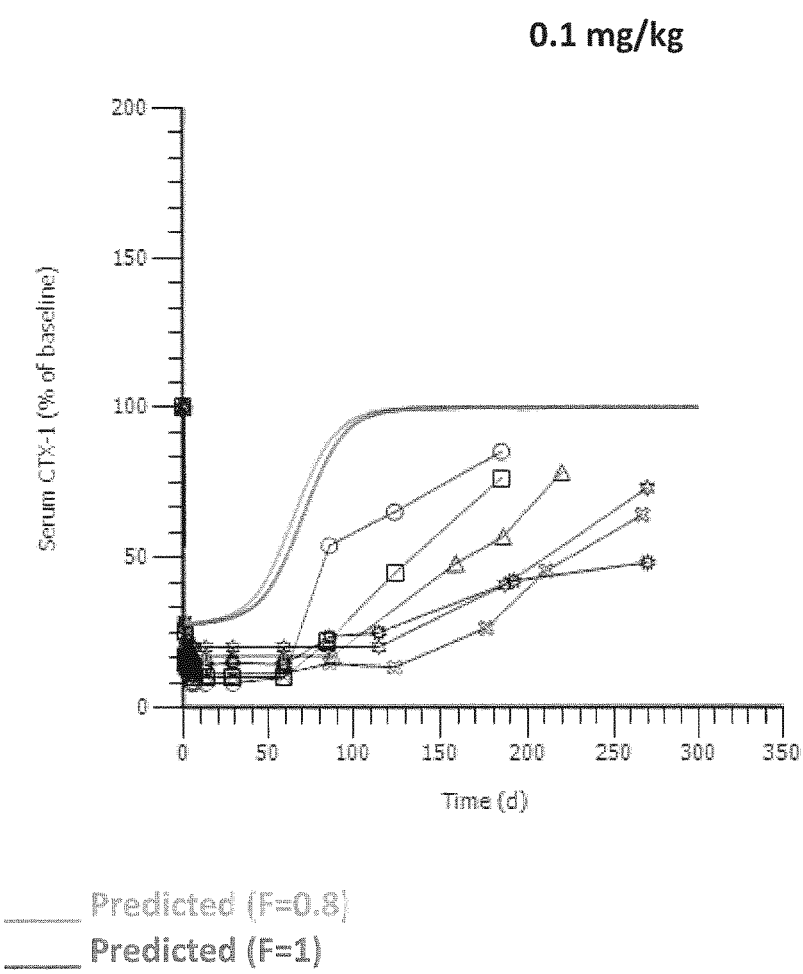
Figure 12:
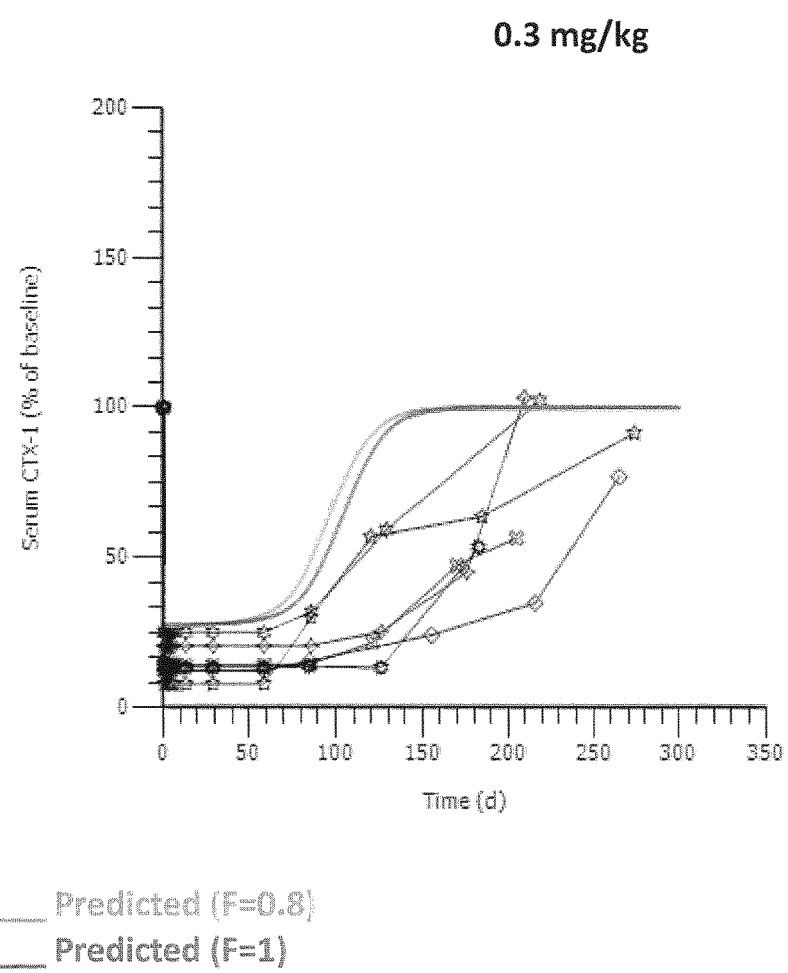
Figure 12:
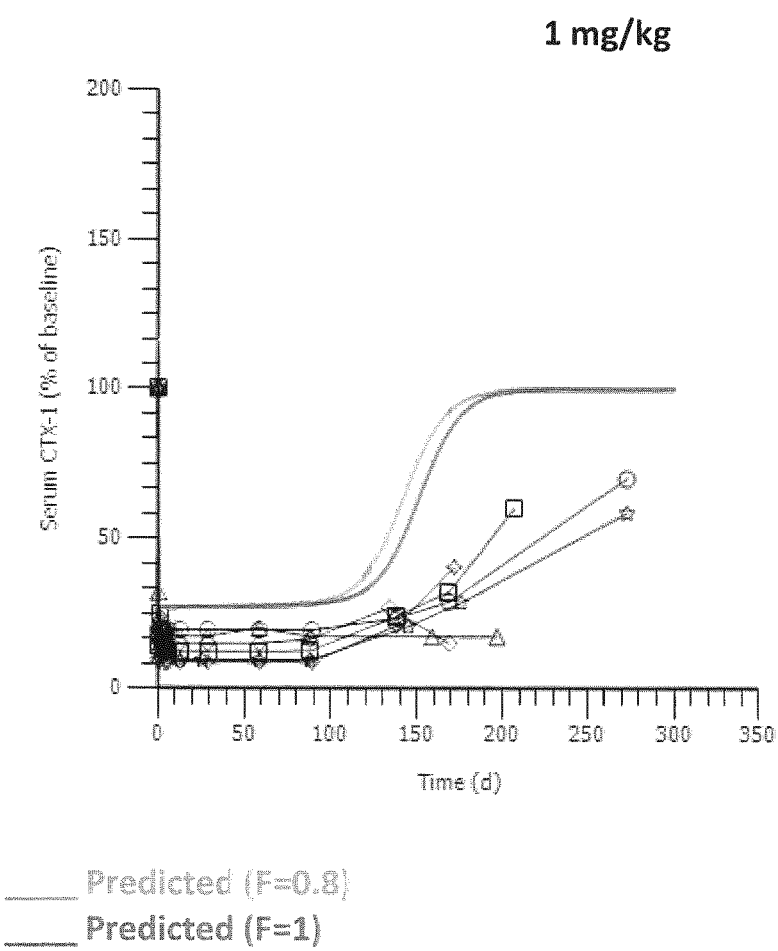

Unexpectedly, the observed serum CTX-1-time profiles in post-menopausal women turned out to be substantially more sustained in humans than what was predicted based on preclinical information (see FIG. 12).

This discrepancy between the observed and the model-based simulations of serum CTX-1-time profiles was attributed to an estimated 5.4-fold greater potency of ALX-0141 in vivo ($IC_{50}$ of 0.674 ng/ml or 16.4 pM) (see Table B-9) relative to that anticipated based on preclinical data (3.7 ng/ml or 89 pM) (see Table B-3).

4.5 Conclusion

Single s.c. administration of ALX-0141 up to 1 mg/kg was safe and well tolerated in healthy post-menopausal women. No deaths or treatment-related serious adverse events (SAEs) occurred and maximum tolerated dose (MTD) has not been reached.

A dose-dependent increase in exposure ($C_{max}$ and AUC) was observed. The PK model is non-linear, due to saturable target-dependent CL component. Serum half-life between 12.0 and 20.6 days was observed for 0.1-1 mg/kg cohorts.

ALX-0141 exhibits statistically significant suppression of serum CTX-1 and urine NTX-1/creatinine biomarkers for bone resorption. This effect is unexpectedly prolonged and sustained as compared to what was predicted based on preclinical information.

Duration of biomarker inhibition following single s.c. ALX-0141 injections increased with dose, reaching maximum duration of 360 days after 1 mg/kg dosing.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references disclosed herein are incorporated by reference, in particular for the teaching that is referenced hereinabove, including specific polypeptides and properties of polypeptides that are useful in the methods described herein.

Tables

TABLE B-1

Pharmacokinetic parameters of ALX-0141 in the cynomolgus monkey.

| Parameter | Estimate | CV % |
|---|---|---|
| $V_c$ (mL/kg) | 68.4 | 10. |
| $V_t$ (mL/kg) | 73.4 | 15. |
| $V_{dss}$ (mL/kg) | 142 | |
| $CL_{NON-RANKL}$ (mL/day/kg) | 8.57 | 5.7 |
| $CL_d$ (mL/day/kg) | 36.2 | 33. |
| $V_{max}$ (μg/day/kg) | 7.096 | 27 |
| $K_m$ (μg/mL) | 0.149 | 49. |
| $CL_{RANKL}$ (mL/day/kg) | 47.7 | |
| ka (day$^{-1}$) | 0.748 | 13. |
| Bioavailability (F) | 0.965 | 6.8 |

TABLE B-2

Allometrically scaled pharmacokinetic parameters of ALX-0141 in humans.

| Parameter | Units | Value |
|---|---|---|
| $V_c$ | (mL/kg) | 68 |
| $V_t$ | (mL/kg) | 73 |
| $V_{dss}$ | (mL/kg) | 72 |
| $CL_{NON-RANKL}$ | (mL/d*) | 3.22 |
| $CL_d$ | (mL/d*) | 14 |
| $V_{max}$ | (μg/d*) | 2.34 |
| $K_m$ | (μg/mL) | 0.149 |
| $CL_{RANKL}$ | (mL/d*) | 15.7 |
| ka | (1/d) | 0.331 |
| Bioavailability (F) | — | 0.80-1.0 |

TABLE B-3

Pharmacodynamic parameters of ALX-0141 in the PK/PD simulations of serum CTX-1 concentrations.

| Parameter | Units | Value |
|---|---|---|
| $k_{in}$ | (nM/d) | 0.732 |
| $k_{out}$ | (1/d) | 16.6 |
| $I_{max}$ | (%) | 0.729 |
| $IC_{50}$ | (ng/mL) | 3.7 |
| | (nM) | 0.089 |
| n | — | 0.88 |

TABLE B-4

ALX-0141 plasma PK parameters

| Dose (mg/kg) | n | $C_{max}$ (μg/mL) | $t_{max}$ (days) | $AUC_{0-last}$ (μg · d/mL) | $AUC_{0-inf}$ (μg · d/mL) | $t_{1/2}$ (d) |
|---|---|---|---|---|---|---|
| 0.003 | 1 | 0.0146$^a$ | 4.00$^a$ | 0.0612$^a$ | —$^b$ | —$^b$ |
| 0.01 | 6 | 0.0327 | 6.00 | 0.321 | —$^b$ | —$^b$ |
| 0.03 | 6 | 0.109 | 3.00 | 1.80 | 1.54$^a$ | 8.86$^a$ |
| 0.1 | 6 | 0.538 | 2.00 | 14.7 | 16.0$^c$ | 12.0$^c$ |
| 0.3 | 6 | 2.24 | 1.50 | 43.3 | 44.3 | 12.4 |
| 1 | 6 | 5.76 | 2.00 | 193 | 200 | 20.6 |

$^a$single observation
$^b$limited data, therefore no descriptive statistics are available
$^c$n = 2

TABLE B-5

PK parameter estimates in healthy post-menopausal women

| Parameter | Estimate [95% CI] | Precision (% CV)$^{(a)}$ |
|---|---|---|
| Absorption | | |
| $k_{a1}$ (1/d) | 1.43 [0.722-2.14] | 25.2 |
| $k_{a2}$ (1/d) | 0.648 [0.411-0.885] | 18.7 |
| F1 | 0.268 [0.194-0.342] | 14.1 |
| Distribution | | |
| V/F (L) | 10.9 [9.83-12.0] | 5.0 |
| WT/V | 1.08 [0.819-1.34] | 12.3 |
| Elimination | | |
| CL/F (L/d) | 0.326 [0.258-0.394] | 10.6 |
| $V_{max}$/F (mg/d) | 0.0422 [0.0355-0.0489] | 8.13 |
| $K_m$ (ng/mL) | 33.1 [11.3-54.9] | 11.1 |

TABLE B-5-continued

PK parameter estimates in healthy post-menopausal women

| Inter-Individual Variability (IIV) | Estimate (% CV)[b] | Precision (% CV)[a] |
|---|---|---|
| IIV in $k_{a1}$ | 169.7 | 37.8 |
| IIV in $k_{a2}$ | 144 | 19.3 |
| IIV in F1 | 0.364[c] | 78.2 |
| IIV in V/F | 22.2 | 26.1 |
| IIV in CL/F | 53.2 | 37.8 |
| IIV in $V_{max}$/F | — | — |
| IIV in $K_m$ | 135 | 57.5 |

| Residual variability in PK | Estimate (SD) | Precision (% CV)[a] |
|---|---|---|
|  | 0.11 | 13.7 |

[a]Precision was calculated as the s.e. divided by the parameter estimate × 100.
[b]The % CV for both inter-subject and residual variability is an approximation taken as the square root of the variance × 100.
[c]An additive random effect model was used for F1, therefore the estimated SD is reported.

TABLE B-6

Summary of PD parameters after single s.c. treatment with ALX-0141 in post-menopausal female subjects

| PD parameter | Treatment | N | Time of nadir$ | Nadir*,$ as percent of baseline (SD) | Nadir as absolute values#,$ (SD) |
|---|---|---|---|---|---|
| CTX-1 | Placebo | 11 | 12 h post-dose Day 1 | 66.7 (12.7) | 0.423 (0.094) |
|  | 0.003 mg/kg | 1 | Day 7 | 50.7 (—) | 0.296 (—) |
|  | 0.01 mg/kg | 5 | Day 14 | 23.7 (14.2) | 0.137 (0.073)†& |
|  | 0.03 mg/kg | 6 | Day 14 | 16.3 (9.5) | 0.085 (0.043) |
|  | 0.1 mg/kg | 6 | Day 14 and 30 | 8.8 (3.6) | 0.047 (0.000)†& |
|  | 0.3 mg/kg | 6 | 12 h post-dose on Day 1 and Day 5 to Day 60 | 7.8 (3.1) | 0.047 (0.000) |
|  | 1 mg/kg | 6 | Day 6 to Day 60 | 11.7 (4.7) | 0.047 (0.000)†‡ |
| TRACP5b | Placebo | 11 | NA | NA | NA |
|  | 0.003 mg/kg | 1 | Day 30 | 70.1 (—) | 2.59 |
|  | 0.01 mg/kg | 6 | Day 30 | 56.0 (10.8) | 2.10 (0.32) |
|  | 0.03 mg/kg | 6 | Day 30 | 65.5 (10.9) | 1.95 (0.38) |
|  | 0.1 mg/kg | 6 | Day 30 | 50.6 (11.7) | 1.62 (0.30) |
|  | 0.3 mg/kg | 6 | Day 60 | 39.1 (6.4) | 1.68 (0.30) |
|  | 1 mg/kg | 6 | Day 30 | 40.4 (6.5) | 1.52 (0.32) |
| P1NP | Placebo | 11 | NA | NA | NA |
|  | 0.003 mg/kg | 1 | Day 60 | 59.3 (—) | 36.6 |
|  | 0.01 mg/kg | 6 | Day 60 | 60.4 (9.1) | 36.0 (7.6) |
|  | 0.03 mg/kg | 6 | Day 90 | 44.9 (5.7) | 20.8 (4.9) |
|  | 0.1 mg/kg | 6 | Day 90 | 25.7 (5.5) | 17.1 (6.8) |
|  | 0.3 mg/kg | 5 | Day 120 | 23.8 (5.3) | 17.2 (9.3) |
|  | 1 mg/kg | 5 | Day 150 | 21.2 (3.9) | 12.1 (2.9) |
| BAP | Placebo | 11 | NA | NA | NA |
|  | 0.003 mg/kg | 1 | NA | NA | NA |
|  | 0.01 mg/kg | 6 | Day 60 | 77.7 (12.1) | 12.2 (1.3) |
|  | 0.03 mg/kg | 6 | Day 60 | 67.6 (11.3) | 12.6 (2.7) |
|  | 0.1 mg/kg | 6 | Day 90 | 71.1 (9.6) | 13.8 (0.8) |
|  | 0.3 mg/kg | 6 | Day 90 | 60.0 (11.3) | 13.8 (4.1) |
|  | 1 mg/kg | 6 | Day 90 | 58.3 (9.2) | 10.5 (2.5) |
| NTX-1 | Placebo | 11 | NA | NA | NA |
|  | 0.003 mg/kg | 1 | Day 4 | 64.8 (—) | 31.3 |
|  | 0.01 mg/kg | 6 | Day 14 | 37.5 (10.9) | 24.7 (7.5) |
|  | 0.03 mg/kg | 6 | Day 14 | 27.9 (13.5) | 12.4 (6.3) |
|  | 0.1 mg/kg | 6 | Day 60 | 19.4 (8.1) | 12.9 (4.4) |
|  | 0.3 mg/kg | 6 | Day 6 | 18.2 (4.0) | 12.8 (3.6) |
|  | 1 mg/kg | 6 | Day 60 | 16.1 (7.4) | 9.8 (4.8) |

For all data arithmetic mean (SD) are presented, except for the 0.003 mg/kg Cohort, since N = 1 for this cohort.
NA: not applicable
$Only given when nadir is below predefined threshold value: 70% of baseline for CTX-1, 80% of baseline for other PD parameters
*The lowest mean value compared to baseline. The results of the placebo-treated subjects of all treatment groups were pooled. Except for CTX-1 serum concentrations and the 0.003 mg/kg dose group, this table only presents mean nadir levels based on N ≥ 5.
CTX-1 levels: ng/mL; TRACP5b: mU/mL; P1NP and BAP: μg/L; NTX-1/creatinine ratios: μmol/mol

TABLE B-7

CTX-1 change from baseline (%)

| Timepoint (nominal) | Placebo (n = 11) | 0.1 mg/kg ALX-0141 (n = 6) | 1.0 mg/kg ALX-0141 (n = 6) |
|---|---|---|---|
| 1 month | −11.6 (4.4) | −84.8 (NA[3])*** | BLQ*** |
| 4 months | 2.5 (6.7) | −60.9 (9.1)*** | −76.7 (1.1)*** |
| 5 months[1] | 2.5 (4.7) | −45.2 (9.2)** | −67.3 (2.8)*** |
| 7 months[2] | 2.5 (3.8) | −31.6 (8.3)** | −40.4 (7.4)*** |
| 9 months | 2.5 (6.7) | −38.0 (7.3)* | −47.0 (7.0)** |

Values: mean (SE),
*p < 0.05,
**p < 0.01,
***p < 0.0001; Placebo values: Last Value Carried Forward
[1]150 d + 180 d,
[2]210 d + 270 d + 300 d,
[3]single observation,
[4]days 300-420

TABLE B-8

NTX-1/creatine change from baseline (%)

| Timepoint (nominal) | Placebo (n = 11) | 0.1 mg/kg ALX-0141 (n = 6) | 1 mg/kg ALX-0141 (n = 6) |
|---|---|---|---|
| 1 month | −5.0 (3.2) | −52.9 (10.6)** | −57.7 (13.6)*** |
| 3 months | −2.3 (4.5) | −39.0 (4.7)** | −58.9 (12.8)*** |
| 6 months | −2.8 (4.8) | −25.1 (12.8) | −55.5 (17.8)** |
| 9 months | −2.8 (4.8) | −24.5 (4.4) | −28.6 (11.9) |
| ≥10 months[4] | −2.8 (2.1) | −12.6 (6.1) | −33.2 (9.3)** |

Values: mean (SE),
*$p < 0.05$,
**$p < 0.01$,
***$p < 0.0001$; Placebo values: Last Value Carried Forward
[1]150 d + 180 d,
[2]210 d + 270 d + 300 d,
[3]single observation,
[4]days 300-420

TABLE B-9

PD parameter estimates in healthy post-menopausal women.

| Parameter | Estimate [95% CI] | Precision (% CV)[a] |
|---|---|---|
| $I_{max}$ | 0.743 [0.695-0.791] | 3.3 |
| $IC_{50}$ (ng/ml) | 0.674 [−0.494-1.842] | 88.4 |
| Baseline (ng/ml) | 0.492 [0.436-0.548] | 5.8 |
| $k_{in}$ (1/d) | 3.86 [0.254-7.466] | 47.7 |
| N | 1[c] | — |
| Lkin[d] | 0.0434 [0.000-0.087] | 51.2 |

| Interindividual Variability (IIV) | Estimate (% CV)[b] | Precision (% CV)[a] |
|---|---|---|
| IIV in $I_{max}$ | 6.4 | 128.9 |
| IIV in $IC_{50}$ | — | — |
| IIV in Base | 22.1 | 39.4 |
| IIV in $k_{in}$ | 46.4 | 76.3 |
| Residual variability in PD | 32.1 | 12.1 |

[a]precision was calculated as the s.e. divided by the parameter estimate × 100.
[b]the % CV for both inter-subject and residual variability is an approximation taken as the square root of the variance × 100.
[c]fixed to unity.
[d]typical fractional dose effect on $k_{in}$ at the lower doses (0.003 and 0.01 mg/kg).

Aspects of the Invention

Aspect A-1: A method for inhibiting bone resorption or osteoclast activity in a subject comprising administering to the subject a polypeptide that specifically binds Receptor Activator of Nuclear Factor kappa B Ligand (RANKL), wherein the amount of the polypeptide administered is effective to change one or more markers of bone metabolism and/or bone homeostasis for at least 30 days after administration.

Aspect A-2: The method according to Aspect A-1, wherein the polypeptide is administered in an amount from about 0.01 mg/kg to about 10 mg/kg.

Aspect A-3: The method according to any of Aspects A-1 and A-2, wherein the markers of bone metabolism are selected from cross-linking telopeptide of type I collagen (CTX-1), N-terminal telopeptide of type I collagen (NTX-1), tartrate-resistant acid phosphatase isoform 5b (TRACP5b), N-terminal propeptide of type I procollagen (P1NP) and bone-specific alkaline phosphatase (BAP).

Aspect A-4: The method according to Aspect A-3, wherein one or more of the CTX-1, NTX-1, TRACP5b, P1NP and BAP is/are measured using an ELISA assay specific for CTX-1, NTX-1, or TRACP5b; a radioimmunoassay specific for P1NP, or an immunoenzymetric assay specific for BAP, respectively.

Aspect A-5: The method according to any of Aspects A-1 to A-4, wherein the polypeptide comprises one or more immunoglobulin single variable domains that specifically bind RANKL.

Aspect A-6: The method according to any of Aspects A-1 to A-5, wherein the polypeptide has an apparent $K_D$ for binding to recombinant soluble RANKL (sRANKL) of 0.01-0.05 nM, preferably about 0.04 nM, as determined by Biacore.

Aspect A-7: The method according to any of Aspects A-1 to A-6, wherein the immunoglobulin single variable domain(s) comprise(s) or consist(s) of one or more VHH domains, one or more humanized VHH domains and/or one or more camelized VH domains.

Aspect A-8: The method according to any of Aspects A-1 to A-7, wherein the polypeptide comprises one or more domain antibodies that specifically bind RANKL, one or more amino acid sequences that specifically bind RANKL that are suitable for use as a domain antibody, one or more single domain antibodies that specifically bind RANKL, one or more amino acid sequences that specifically bind RANKL that are suitable for use as a single domain antibody, or one or more "dAb"s that specifically bind RANKL.

Aspect A-9: The method according to any of Aspects A-1 to A-8, wherein the polypeptide is a multivalent construct comprising two or more immunoglobulin single variable domains that specifically bind RANKL.

Aspect A-10: The method according to Aspect A-9, wherein the multivalent construct comprises two immunoglobulin single variable domains that specifically bind RANKL.

Aspect A-11: The method according to any of Aspects A-5 to A-10, wherein the immunoglobulin single variable domain essentially consists of 4 framework regions (FR1 to FR4, respectively) and 3 complementarity determining regions (CDR1 to CDR3, respectively), in which CDR1 is chosen from SEQ ID NO: 1, CDR2 is chosen from SEQ ID NO: 2, and CDR3 is chosen from SEQ ID NO: 3.

Aspect A-12: The method according to any of Aspects A-5 to A-11, wherein the multivalent construct comprises or consists of SEQ ID NO: 10 or SEQ ID NO: 12.

Aspect A-13: The method according to any of Aspects A-5 to A-12, wherein the multivalent construct further comprises at least one half-life extension moiety.

Aspect A-14: The method according to Aspect A-13, wherein the at least one half-life extension moiety specifically binds a serum protein.

Aspect A-15: The method according to Aspect A-14, wherein the serum protein is serum albumin, and in particular human serum albumin, thyroxine-binding protein, (human) transferrin, fibrinogen, an immunoglobulin such as IgG, IgE or IgM, or one of the serum proteins listed in WO 04/003019.

Aspect A-16: The method according to any of Aspects A-13 to A-15, wherein at least one half-life extension moiety comprises or consists of an immunoglobulin single variable domain.

Aspect A-17: The method according to Aspect A-16, wherein the immunoglobulin single variable domain comprises or consists of a VHH domain, a humanized VHH domain or a camelized VH domain.

Aspect A-18: The method according to any of Aspects A-16 or A-17, wherein the immunoglobulin single variable domain comprises or consists of SEQ ID NO: 14.

Aspect A-19: The method according to any of Aspects A-13 to A-16, wherein the at least one half-life extension moiety comprises a domain antibody, an amino acid sequence that is suitable for use as a domain antibody, a single domain antibody, an amino acid sequence that is suitable for use as a single domain antibody, or a "dAb".

Aspect A-20: The method according to Aspect A-13, wherein the at least one half-life extension moiety comprises one or more polyethylene glycol molecules.

Aspect A-21: The method according to any of Aspects A-5 to A-11, wherein the polypeptide cross-blocks the binding of SEQ ID NO: 10 or SEQ ID NO: 12 to RANKL.

Aspect A-22: The method according to any of Aspects A-5 to A-11, wherein the polypeptide is cross-blocked from binding RANKL by SEQ ID NO: 10 or SEQ ID NO: 12.

Aspect A-23: The method according to any of Aspects A-1 to A-22, wherein the polypeptide is administered as a single dose.

Aspect A-24: The method according to any of Aspects A-1 to A-23, wherein the polypeptide is administered subcutaneously.

Aspect A-25: The method according to any of Aspects A-1 to A-24, wherein the subject has osteoporosis.

Aspect B-1: The method according to any of Aspects A-1 to A-25, wherein the marker of bone metabolism is cross-linking telopeptide of type I collagen (CTX-1).

Aspect B-2: The method according to Aspect B-1, wherein the amount of the polypeptide administered is effective to reduce serum levels of CTX-1 by at least 30%, compared to pre-treatment or normal levels, for at least about 30, 60, 90, 120, 150, 180, 210, or 270 days after administration.

Aspect B-3: The method according to Aspect B-2, wherein the polypeptide is administered in an amount from about 0.003 mg/kg to about 0.03 mg/kg.

Aspect B-4: The method according to Aspects B-3, wherein the serum levels of CTX-1 are reduced by at least 30%, compared to pre-treatment or normal levels, for at least about 30 days after administration.

Aspect B-5: The method according to Aspect B-2, wherein the polypeptide is administered in an amount from about 0.01 mg/kg to about 0.1 mg/kg.

Aspect B-6: The method according to Aspects B-5, wherein the serum levels of CTX-1 are reduced by at least 30%, compared to pre-treatment or normal levels, for at least about 60 days after administration.

Aspect B-7: The method according to Aspect B-6, wherein the serum levels of CTX-1 are reduced by at least 30%, compared to pre-treatment or normal levels, for at least about 90 days after administration.

Aspect B-8: The method according to Aspect B-7, wherein the serum levels of CTX-1 are reduced by at least 30%, compared to pre-treatment or normal levels, for at least about 120 days after administration.

Aspect B-9: The method according to Aspect B-2, wherein the polypeptide is administered in an amount from about 0.1 mg/kg to about 1 mg/kg.

Aspect B-10: The method according to Aspect B-9, wherein the serum levels of CTX-1 are reduced by at least 30%, compared to pre-treatment or normal levels, for at least about 150 days after administration.

Aspect B-11: The method according to Aspect B-10, wherein the serum levels of CTX-1 are reduced by at least 30%, compared to pre-treatment or normal levels, for at least about 180 days after administration.

Aspect B-12: The method according to Aspect B-11, wherein the serum levels of CTX-1 are reduced by at least 30%, compared to pre-treatment or normal levels, for at least about 210 days after administration.

Aspect B-13: The method according to Aspect B-12, wherein the serum levels of CTX-1 are reduced by at least 30%, compared to pre-treatment or normal levels, for at least about 270 days after administration.

Aspect B-14: The method according to Aspect B-1, wherein the amount of the polypeptide administered is effective to reduce serum level of cross-linking telopeptide of type I collagen (CTX-1) by at least 45%, compared to pre-treatment or normal levels, for at least about 30, 60, 90, 120, 150, or 180 days, and/or 30 days to 3 months, 3 months to 6 months, or 6 months to 1 year after administration.

Aspect B-15: The method according to Aspect B-14, wherein the polypeptide is administered in an amount of less than or equal to 0.03 mg/kg.

Aspect B-16: The method according to Aspect B-14, wherein the polypeptide is administered in an amount from about 0.01 mg/kg to about 3 mg/kg.

Aspect B-17: The method according to Aspect B-16, wherein the polypeptide is administered in an amount from about 0.01 mg/kg to about 0.1 mg/kg.

Aspect B-18: The method according to any of Aspects B-15 to B-17, wherein the serum levels of CTX-1 are reduced by at least 45%, compared to pre-treatment or normal levels, for at least about 30 days after administration.

Aspect B-19: The method according to any of Aspects B-16 and B-17, wherein the serum levels of CTX-1 are reduced by at least 45%, compared to pre-treatment or normal levels, for at least about 60 days after administration.

Aspect B-20: The method according to Aspect B-14, wherein the polypeptide is administered in an amount from about 0.03 mg/kg to about 0.3 mg/kg.

Aspect B-21: The method according to Aspect B-14, wherein the polypeptide is administered in an amount from about 0.01 mg/kg to about 0.3 mg/kg.

Aspect B-22: The method according to any of Aspects B-20 and B-21, wherein the serum levels of CTX-1 are reduced by at least 45%, compared to pre-treatment or normal levels, for at least about 90 days after administration.

Aspect B-23: The method according to any of Aspects B-20 and B-21, wherein the CTX-1 is reduced by at least 45%, compared to pre-treatment or normal levels, for about 30 days to 3 months after administration.

Aspect B-24: The method according to Aspect B-14, wherein the polypeptide is administered in an amount from about 0.1 mg/kg to about 1 mg/kg.

Aspect B-25: The method according to Aspect B-24, wherein the serum levels of CTX-1 are reduced by at least 45%, compared to pre-treatment or normal levels, for at least about 120 days after administration.

Aspect B-26: The method according to Aspect B-14, wherein the polypeptide is administered in an amount from about 0.3 mg/kg to about 1 mg/kg.

Aspect B-27: The method according to Aspect B-14, wherein the polypeptide is administered in an amount of less than or equal to 0.3 mg/kg.

Aspect B-28: The method according to any of Aspects B-26 and B-27, wherein the CTX-1 is reduced by at least 45%, compared to pre-treatment or normal levels, for about 3 months to 6 months after administration.

Aspect B-29: The method according to Aspect B-14, wherein the polypeptide is administered in an amount from about 1 mg/kg to about 10 mg/kg.

Aspect B-30: The method according to Aspect B-14, wherein the polypeptide is administered in an amount from about 1 mg/kg to about 3 mg/kg.

Aspect B-31: The method according to Aspect B-14, wherein the polypeptide is administered in an amount of less than or equal to 1 mg/kg.

Aspect B-32: The method according to any of Aspects B-29, B-30 and B-31, wherein the serum levels of CTX-1 are reduced by at least 45%, compared to pre-treatment or normal levels, for at least about 150 days after administration.

Aspect B-33: The method according to Aspect B-32, wherein the serum levels of CTX-1 are reduced by at least 45%, compared to pre-treatment or normal levels, for at least about 180 days (or 6 months) after administration.

Aspect B-34: The method according to any of Aspects B-29, B-30 and B-31, wherein the CTX-1 is reduced by at least 45%, compared to pre-treatment or normal levels, for at least 6 months to 1 year after administration.

Aspect B-35: The method according to Aspect B-1, wherein the amount of the polypeptide administered is effective to reduce serum levels of CTX-1 by at least 70%, compared to pre-treatment or normal levels, for at least about 30, 60, 90, or 120 days after administration.

Aspect B-36: The method according to Aspect B-35, wherein the polypeptide is administered in an amount from about 0.03 mg/kg to about 0.3 mg/kg.

Aspect B-37: The method according to Aspect B-36, wherein the serum levels of CTX-1 are reduced by at least 70%, compared to pre-treatment or normal levels, for at least about 30 days after administration.

Aspect B-38: The method according to Aspect B-35, wherein the polypeptide is administered in an amount from about 0.1 mg/kg to about 1 mg/kg.

Aspect B-39: The method according to Aspect B-38, wherein the serum levels of CTX-1 are reduced by at least 70%, compared to pre-treatment or normal levels, for at least about 60 days after administration.

Aspect B-40: The method according to Aspect B-39, wherein the serum levels of CTX-1 are reduced by at least 70%, compared to pre-treatment or normal levels, for at least about 90 days after administration.

Aspect B-41: The method according to Aspect B-40, wherein the serum levels of CTX-1 are reduced by at least 70%, compared to pre-treatment or normal levels, for at least about 120 days after administration.

Aspect B-42: The method according to Aspect B-1, wherein the amount of the polypeptide administered is effective to reduce serum levels of CTX-1 by at least 80%, compared to pre-treatment or normal levels, for at least about 30, 60, or 90 days after administration.

Aspect B-43: The method according to Aspect B-42, wherein the polypeptide is administered in an amount from about 0.1 mg/kg to about 1 mg/kg.

Aspect B-44: The method according to Aspect B-42, wherein the polypeptide is administered in an amount from about 0.3 mg/kg to about 1 mg/kg.

Aspect B-45: The method according to any of Aspects B-43 and B-44, wherein the serum levels of CTX-1 are reduced by at least 80%, compared to pre-treatment or normal levels, for at least about 60 days after administration.

Aspect B-46: The method according to Aspect B-45 wherein the serum levels of CTX-1 are reduced by at least 80%, compared to pre-treatment or normal levels, for at least about 90 days after administration.

Aspect B-47: The method according to any of Aspects B-1 to B-46, wherein the amount of the polypeptide administered is effective to reduce serum levels of cross-linking telopeptide of type I collagen (CTX-1) by at least 45% by 8 hours after administration.

Aspect B-48: The method according to any of Aspects B-1 to B-47, wherein bone resorption is inhibited in the subject as determined by ELISA assay for CTX-1.

Aspect B-49: The method according to any of Aspects B-1 to B-48, wherein the CTX-1 is reduced by at least 50%, compared to pre-treatment or normal levels, for at least 30 days after administration.

Aspect B-50: The method according to any of Aspects B-1 to B-49, wherein the CTX-1 is reduced by at least 50%, compared to pre-treatment or normal levels, for at least 60 days after administration.

Aspect B-51: The method according to any of Aspects B-1 to B-50, wherein the CTX-1 is reduced by at least 50%, compared to pre-treatment or normal levels, for at least 90 days after administration.

Aspect B-52: The method according to any of Aspects B-1 to B-51, wherein the CTX-1 is reduced by at least 50%, compared to pre-treatment or normal levels, for at least 120 days after administration.

Aspect B-53: The method according to any of Aspects B-1 to B-52, wherein the CTX-1 is reduced by at least 50%, compared to pre-treatment or normal levels, for at least 150 days after administration.

Aspect B-54: The method according to any of Aspects B-1 to B-53, wherein the CTX-1 is reduced by at least 50%, compared to pre-treatment or normal levels, for at least 180 days after administration.

Aspect B-55: The method according to any of Aspects B-1 to B-54, wherein the CTX-1 is reduced by at least 60%, compared to pre-treatment or normal levels, for at least 30 days after administration.

Aspect B-56: The method according to any of Aspects B-1 to B-55, wherein the CTX-1 is reduced by at least 60%, compared to pre-treatment or normal levels, for at least 60 days after administration.

Aspect B-57: The method according to any of Aspects B-1 to B-56, wherein the CTX-1 is reduced by at least 60%, compared to pre-treatment or normal levels, for at least 90 days after administration.

Aspect B-58: The method according to any of Aspects B-1 to B-57, wherein the CTX-1 is reduced by at least 60%, compared to pre-treatment or normal levels, for at least 120 days after administration.

Aspect B-59: The method according to any of Aspects B-1 to B-58, wherein the CTX-1 is reduced by at least 60%, compared to pre-treatment or normal levels, for at least 150 days after administration.

Aspect B-60: The method according to any of Aspects B-1 to B-59, wherein the CTX-1 is reduced by at least 70%, compared to pre-treatment or normal levels, for at least 30 days after administration.

Aspect B-61: The method according to any of Aspects B-1 to B-60, wherein the CTX-1 is reduced by at least 70%, compared to pre-treatment or normal levels, for at least 60 days after administration.

Aspect B-62: The method according to any of Aspects B-1 to B-61, wherein the CTX-1 is reduced by at least 70%, compared to pre-treatment or normal levels, for at least 90 days after administration.

Aspect B-63: The method according to any of Aspects B-1 to B-62, wherein the CTX-1 is reduced by at least 70%, compared to pre-treatment or normal levels, for at least 120 days after administration.

Aspect B-64: The method according to any of Aspects B-1 to B-63, wherein the CTX-1 is reduced by at least 80%, compared to pre-treatment or normal levels, for at least 30 days after administration.

Aspect B-65: The method according to any of Aspects B-1 to B-64, wherein the CTX-1 is reduced by at least 80%, compared to pre-treatment or normal levels, for at least 60 days after administration.

Aspect B-66: The method according to any of Aspects B-1 to B-65, wherein the CTX-1 is reduced by at least 80%, compared to pre-treatment or normal levels, for at least 90 days after administration.

Aspect C-1: The method of any of Aspects A-1 to A-25, wherein the marker of bone metabolism is N-terminal telopeptide of type I collagen (NTX-1).

Aspect C-2: The method according to Aspect C-1, wherein the amount of the polypeptide administered is effective to reduce NTX-1 by at least 30%, determined as ratio of NTX-1 to creatinine in urine, compared to pre-treatment or normal levels, for at least 30, 60, 90, 120, or 180 days, and/or at least 10 months or at least 12 months after administration.

Aspect C-3: The method according to Aspect C-2, wherein the polypeptide is administered in an amount from about 0.01 mg/kg to about 0.1 mg/kg.

Aspect C-4: The method according to Aspect C-3, wherein the levels of NTX-1 are reduced by at least 30%, compared to pre-treatment or normal levels, for at least about 30 days after administration.

Aspect C-5: The method according to Aspect C-4, wherein the levels of NTX-1 are reduced by at least 30%, compared to pre-treatment or normal levels, for at least about 60 days after administration.

Aspect C-6: The method according to Aspect C-2, wherein the polypeptide is administered in an amount from about 0.03 mg/kg to about 0.3 mg/kg.

Aspect C-7: The method according to Aspect C-6, wherein the levels of NTX-1 are reduced by at least 30%, compared to pre-treatment or normal levels, for at least about 90 days after administration.

Aspect C-8: The method according to Aspect C-2, wherein the polypeptide is administered in an amount from about 0.1 mg/kg to about 1 mg/kg.

Aspect C-9: The method according to Aspect C-8, wherein the levels of NTX-1 are reduced by at least 30%, compared to pre-treatment or normal levels, for at least about 120 days after administration.

Aspect C-10: The method according to Aspect C-2, wherein the polypeptide is administered in an amount from about 1 mg/kg to about 10 mg/kg.

Aspect C-11: The method according to Aspect C-10, wherein the levels of NTX-1 are reduced by at least 30%, compared to pre-treatment or normal levels, for at least about 180 days (or 6 months) after administration.

Aspect C-12: The method according to Aspect C-10, wherein the levels of NTX-1 are reduced by at least 30%, compared to pre-treatment or normal levels, for at least about 10 months after administration.

Aspect C-13: The method according to Aspect C-10, wherein the levels of NTX-1 are reduced by at least 30%, compared to pre-treatment or normal levels, for at least about 1 year (12 months; 360 days) after administration.

Aspect C-14: The method according to Aspect C-1, wherein the amount of the polypeptide administered is effective to reduce NTX-1 by at least 45%, determined as ratio of NTX-1 to creatinine in urine, compared to pre-treatment or normal levels, for at least 30, 60, 90, 120, 180, or 210 days and/or 30 days to 3 months, 3 months to 6 months, or 6 months to 1 year after administration.

Aspect C-15: The method according to Aspect C-14, wherein the polypeptide is administered in an amount from about 0.01 mg/kg to about 3 mg/kg.

Aspect C-16: The method according to Aspect C-15, wherein the polypeptide is administered in an amount from about 0.01 mg/kg to about 0.1 mg/kg.

Aspect C-17: The method according to any of Aspects C-15 and C-16, wherein the levels of NTX-1 are reduced by at least 45%, compared to pre-treatment or normal levels, for at least about 60 days after administration.

Aspect C-18: The method according to Aspect C-14, wherein the polypeptide is administered in an amount from about 0.03 mg/kg to about 0.3 mg/kg.

Aspect C-19: The method according to Aspect C-18, wherein the levels of NTX-1 are reduced by at least 45%, compared to pre-treatment or normal levels, for at least about 60 days after administration.

Aspect C-20: The method according to Aspect C-14, wherein the polypeptide is administered in an amount from about 0.01 mg/kg to about 3 mg/kg.

Aspect C-21: The method according to Aspect C-14, wherein the polypeptide is administered in an amount from about 0.01 mg/kg to about 0.3 mg/kg.

Aspect C-22: The method according to Aspect C-14, wherein the polypeptide is administered in an amount from about 0.03 mg/kg to about 0.3 mg/kg.

Aspect C-23: The method according to Aspect C-14, wherein the polypeptide is administered in an amount of less than or equal to 0.03 mg/kg.

Aspect C-24: The method according to any of Aspects C-20, C-21, C-22 and C-23, wherein the levels of NTX-1 are reduced by at least 45%, compared to pre-treatment or normal levels, for at least about 30 days to 3 months after administration.

Aspect C-25: The method according to Aspect C-14, wherein the polypeptide is administered in an amount from about 0.1 mg/kg to about 1 mg/kg.

Aspect C-26: The method according to Aspect C-25, wherein the levels of NTX-1 are reduced by at least 45%, compared to pre-treatment or normal levels, for at least about 90 days after administration.

Aspect C-27: The method according to Aspect C-26, wherein the levels of NTX-1 are reduced by at least 45%, compared to pre-treatment or normal levels, for at least about 120 days after administration.

Aspect C-28: The method according to Aspect C-27, wherein the levels of NTX-1 are reduced by at least 45%, compared to pre-treatment or normal levels, for at least about 150 days after administration.

Aspect C-29: The method according to Aspect C-14, wherein the polypeptide is administered in an amount from about 0.01 mg/kg to about 3 mg/kg.

Aspect C-30: The method according to Aspect C-14, wherein the polypeptide is administered in an amount from about 0.3 mg/kg to about 1 mg/kg.

Aspect C-31: The method according to Aspect C-14, wherein the polypeptide is administered in an amount of less than or equal to 0.3 mg/kg.

Aspect C-32: The method of any of Aspects C-29, C-30 and C-31, wherein the NTX-1 is reduced by at least 45%, compared to pre-treatment or normal levels, for about 3 months to 6 months after administration.

Aspect C-33: The method according to Aspect C-14, wherein the polypeptide is administered in an amount from about 1 mg/kg to about 10 mg/kg.

Aspect C-34: The method according to Aspect C-14, wherein the polypeptide is administered in an amount from about 1 mg/kg to about 3 mg/kg.

Aspect C-35: The method according to Aspect C-14, wherein the polypeptide is administered in an amount of less than or equal to 1 mg/kg.

Aspect C-36: The method according to any of Aspects C-33, C-34 and C-35, wherein the levels of NTX-1 are reduced by at least 45%, compared to pre-treatment or normal levels, for at least about 180 days (or 6 months) after administration.

Aspect C-37: The method according to any of Aspects C-33, C-34 and C-35, wherein the levels of NTX-1 are reduced by at least 45%, compared to pre-treatment or normal levels, for at least about 210 days after administration.

Aspect C-38: The method according to any of Aspects C-33, C-34 and C-35, wherein the levels of NTX-1 are reduced by at least 45%, compared to pre-treatment or normal levels, for at least about 6 months to 1 year after administration.

Aspect C-39: The method according to Aspect C-1, wherein the amount of the polypeptide administered is effective to reduce levels of NTX-1 by at least 70%, compared to pre-treatment or normal levels, for at least about 30, 60, 90, or 120 days after administration.

Aspect C-40: The method according to Aspect C-39, wherein the polypeptide is administered in an amount from about 0.1 mg/kg to about 1 mg/kg.

Aspect C-41: The method according to Aspect C-40, wherein the levels of NTX-1 are reduced by at least 70%, compared to pre-treatment or normal levels, for at least about 30 days after administration.

Aspect C-42: The method according to Aspect C-39, wherein the polypeptide is administered in an amount from about 0.3 mg/kg to about 3 mg/kg.

Aspect C-43: The method according to Aspect C-42, wherein the levels of NTX-1 are reduced by at least 70%, compared to pre-treatment or normal levels, for at least about 60 days after administration.

Aspect C-44: The method according to Aspect C-43, wherein the levels of NTX-1 are reduced by at least 70%, compared to pre-treatment or normal levels, for at least about 90 days after administration.

Aspect C-45: The method according to Aspect C-39, wherein the polypeptide is administered in an amount from about 1 mg/kg to about 10 mg/kg.

Aspect C-46: The method according to Aspect C-45, wherein the levels of NTX-1 are reduced by at least 70%, compared to pre-treatment or normal levels, for at least about 120 days after administration.

Aspect C-47: The method according to Aspect C-1, wherein the amount of the polypeptide administered is effective to reduce levels of NTX-1 by at least 80%, compared to pre-treatment or normal levels, for at least about 30, 60, or 90 days after administration.

Aspect C-48: The method according to Aspect C-47, wherein the polypeptide is administered in an amount from about 0.3 mg/kg to about 3 mg/kg.

Aspect C-49: The method according to Aspect C-47, wherein the polypeptide is administered in an amount from about 0.3 mg/kg to about 1 mg/kg.

Aspect C-50: The method according to Aspect C-47, wherein the polypeptide is administered in an amount from about 0.1 mg/kg to about 1 mg/kg.

Aspect C-51: The method according to any of Aspects C-48 and C-49, wherein the levels of NTX-1 are reduced by at least 80%, compared to pre-treatment or normal levels, for at least about 30 days after administration.

Aspect C-52: The method according to any of Aspects C-49 and C-50, wherein the levels of NTX-1 are reduced by at least 80%, compared to pre-treatment or normal levels, for at least about 30 days to 3 months after administration.

Aspect C-53: The method according to Aspect C-47, wherein the polypeptide is administered in an amount from about 1 mg/kg to about 10 mg/kg.

Aspect C-54: The method according to Aspect C-53, wherein the levels of NTX-1 are reduced by at least 80%, compared to pre-treatment or normal levels, for at least about 60 days after administration.

Aspect C-55: The method according to Aspect C-54, wherein the levels of NTX-1 are reduced by at least 80%, compared to pre-treatment or normal levels, for at least about 90 days after administration.

Aspect C-56: The method according to any of Aspects C-1 to C-55, wherein the NTX-1 is reduced by at least 20%, compared to pre-treatment or normal levels, for at least 90 days after administration.

Aspect C-57: The method according to any of Aspects C-1 to C-56, wherein the NTX-1 is reduced by at least 20%, compared to pre-treatment or normal levels, for at least 120 days after administration.

Aspect C-58: The method according to any of Aspects C-1 to C-57, wherein the NTX-1 is reduced by at least 20%, compared to pre-treatment or normal levels, for at least 150 days after administration.

Aspect C-59: The method according to any of Aspects C-1 to C-58, wherein the NTX-1 is reduced by at least 20%, compared to pre-treatment or normal levels, for at least 180 days after administration.

Aspect C-60: The method according to any of Aspects C-1 to C-59, wherein the amount of the polypeptide administered is effective to reduce urine levels of NTX-1 by at least 45% by 8 hours after administration.

Aspect C-61: The method according to any of Aspects C-1 to C-60, wherein the ratio of NTX-1 to creatinine in urine in the subject is determined by ELISA assay for NTX-1.

The method according to aspects C-1 to C-61 may in particular be a method according to any of the Aspects B-1 to B-66.

Aspect D-1: The method of any of Aspects A-1 to A-25, wherein the marker of bone metabolism is tartrate-resistant acid phosphatase isoform 5b (TRACP5b).

Aspect D-2: The method according to Aspect D-1, wherein the amount of the polypeptide administered is effective to reduce serum levels of TRACP5b by at least 30%, compared to pre-treatment or normal levels, for at least about 30, 60, 90 or 120 days after administration.

Aspect D-3: The method according to Aspect D-2, wherein the polypeptide is administered in an amount from about 0.03 mg/kg to about 0.3 mg/kg.

Aspect D-4: The method according to Aspect D-3, wherein the serum levels of TRACP5b are reduced by at least 30%, compared to pre-treatment or normal levels, for at least about 30 days after administration.

Aspect D-5: The method according to Aspect D-4, wherein the serum levels of TRACP5b are reduced by at least 30%, compared to pre-treatment or normal levels, for at least about 60 days after administration.

Aspect D-6: The method according to Aspect D-2, wherein the polypeptide is administered in an amount from about 0.1 mg/kg to about 1 mg/kg.

Aspect D-7: The method according to Aspect D-6, wherein the serum levels of TRACP5b are reduced by at least 30%, compared to pre-treatment or normal levels, for at least about 90 days after administration.

Aspect D-8: The method according to Aspect D-2, wherein the polypeptide is administered in an amount from about 0.3 mg/kg to about 3 mg/kg.

Aspect D-9: The method according to Aspect D-8, wherein the serum levels of TRACP5b are reduced by at least 30%, compared to pre-treatment or normal levels, for at least about 120 days after administration.

Aspect D-10: The method according to Aspect D-1, wherein the amount of the polypeptide administered is effective to reduce serum level of TRACP5b by at least 45%, compared to pre-treatment or normal levels, for at least about 30, 60, or 90 days after administration.

Aspect D-11: The method according to Aspect D-10, wherein the polypeptide is administered in an amount from about 0.1 mg/kg to about 1 mg/kg.

Aspect D-12: The method according to Aspect D-11, wherein the serum levels of TRACP5b are reduced by at least 45%, compared to pre-treatment or normal levels, for at least about 30 days after administration.

Aspect D-13: The method according to Aspect D-10, wherein the polypeptide is administered in an amount from about 0.3 mg/kg to about 3 mg/kg.

Aspect D-14: The method according to Aspect D-13, wherein the serum levels of TRACP5b are reduced by at least 45%, compared to pre-treatment or normal levels, for at least about 60 days after administration.

Aspect D-15: The method according to Aspect D-14, wherein the serum levels of TRACP5b are reduced by at least 45%, compared to pre-treatment or normal levels, for at least about 90 days after administration.

The method according to aspects D-1 to D-15 may in particular be a method according to any of the Aspects B-1 to B-66 and/or C-1 to C-61.

Aspect E-1: The method of any of Aspects A-1 to A-25, wherein the marker of bone metabolism is N-terminal propeptide of type I procollagen (P1NP).

Aspect E-2: The method according to Aspect E-1, wherein the amount of the polypeptide administered is effective to reduce serum levels of P1NP by at least 30%, compared to pre-treatment or normal levels, for at least about 30, 60, 90, or 120 days after administration.

Aspect E-3: The method according to Aspect E-2, wherein the polypeptide is administered in an amount from about 0.003 mg/kg to about 0.03 mg/kg.

Aspect E-4: The method according to Aspect E-3, wherein the serum levels of P1NP are reduced by at least 30%, compared to pre-treatment or normal levels, for at least about 30 days after administration.

Aspect E-5: The method according to Aspect E-4, wherein the serum levels of P1NP are reduced by at least 30%, compared to pre-treatment or normal levels, for at least about 60 days after administration.

Aspect E-6: The method according to Aspect E-5, wherein the serum levels of P1NP are reduced by at least 30%, compared to pre-treatment or normal levels, for at least about 90 days after administration.

Aspect E-7: The method according to Aspect E-2, wherein the polypeptide is administered in an amount from about 0.01 mg/kg to about 0.1 mg/kg.

Aspect E-8: The method according to Aspect E-7, wherein the serum levels of P1NP 1 are reduced by at least 30%, compared to pre-treatment or normal levels, for at least about 120 days after administration.

Aspect E-9: The method according to Aspect E-1, wherein the amount of the polypeptide administered is effective to reduce serum level of P1NP by at least 45%, compared to pre-treatment or normal levels, for at least about 30, 60, or 90 days after administration.

Aspect E-10: The method according to Aspect E-9, wherein the polypeptide is administered in an amount from about 0.03 mg/kg to about 0.3 mg/kg.

Aspect E-11: The method according to Aspect E-10, wherein the serum levels of P1NP are reduced by at least 45%, compared to pre-treatment or normal levels, for at least about 30 days after administration.

Aspect E-12: The method according to Aspect E-11, wherein the serum levels of P1NP are reduced by at least 45%, compared to pre-treatment or normal levels, for at least about 60 days after administration.

Aspect E-13: The method according to according to Aspect E-12, wherein the serum levels of P1NP are reduced by at least 45%, compared to pre-treatment or normal levels, for at least about 90 days after administration.

Aspect E-14: The method according to Aspect E-1, wherein the amount of the polypeptide administered is effective to reduce serum levels of P1NP by at least 70%, compared to pre-treatment or normal levels, for at least about 30, 60, or 90 days after administration.

Aspect E-15: The method according to Aspect E-14, wherein the polypeptide is administered in an amount from about 0.1 mg/kg to about 1 mg/kg.

Aspect E-16: The method according to Aspect E-15, wherein the serum levels of P1NP are reduced by at least 70%, compared to pre-treatment or normal levels, for at least about 30 days after administration.

Aspect E-17: The method according to Aspect E-16, wherein the serum levels of P1NP are reduced by at least 70%, compared to pre-treatment or normal levels, for at least about 60 days after administration.

Aspect E-18: The method according to Aspect E-17, wherein the serum levels of P1NP are reduced by at least 70%, compared to pre-treatment or normal levels, for at least about 90 days after administration.

The method according to aspects E-1 to e-18 may in particular be a method according to any of the Aspects B-1 to B-66, C-1 to C-61 and/or D-1 to D-15.

The invention claimed is:

1. A method for treatment of bone diseases and/or disorders characterized by insufficient bone formation and/or excessive bone resorption in a post-menopausal female human subject, by inhibiting bone resorption or osteoclast activity comprising administering a polypeptide that specifically binds Receptor Activator of Nuclear Factor kappa B Ligand (RANKL) to the post-menopausal female human subject, wherein the amount of the polypeptide administered is effective to change one or more markers of bone metabolism and/or bone homeostasis selected from cross-linking telopeptide of type I collagen (CTX-1), N-terminal telopeptide of type I collagen (NTX-1), for at least 30 days after administration, wherein the polypeptide comprises two or more immunoglobulin single variable domains that specifically bind RANKL and that essentially consist of 4 framework regions (FR1 to FR4, respectively) and 3 complementarity determining regions (CDR1 to CDR3, respectively), in which CDR1 is SEQ ID NO: 1, CDR2 is SEQ ID NO: 2, and CDR3 is SEQ ID NO: 3, and wherein the polypeptide is administered in an amount from about 0.003 mg/kg to about 0.01 mg/kg every month and the serum levels of CTX-1 are reduced by at least 30% compared to pre-treatment or normal levels, and the serum levels of CTX-1 are maintained throughout the treatment period at a level that is reduced by at least 30% compared to pre-treatment or normal levels;

the polypeptide is administered in an amount from about 0.01 mg/kg to about 0.03 mg/kg every two months and the serum levels of CTX-1 are reduced by at least 30% compared to pre-treatment or normal levels, and the serum levels of CTX-1 are maintained throughout the treatment period at a level that is reduced by at least 30% compared to pre-treatment or normal levels;

the polypeptide is administered in an amount from about 0.01 mg/kg to about 0.03 mg/kg every three months and the serum levels of CTX-1 are reduced by at least 30% compared to pre-treatment or normal levels, and the serum levels of CTX-1 are maintained throughout the treatment period at a level that is reduced by at least 30% compared to pre-treatment or normal levels;

the polypeptide is administered in an amount from about 0.01 mg/kg to about 0.03 mg/kg every four months and the serum levels of CTX-1 are reduced by at least 30% compared to pre-treatment or normal levels, and the serum levels of CTX-1 are maintained throughout the treatment period at a level that is reduced by at least 30% compared to pre-treatment or normal levels;

the polypeptide is administered in an amount from about 0.01 mg/kg to about 0.03 mg/kg every month and the serum levels of CTX-1 are reduced by at least 45% compared to pre-treatment or normal levels, and the serum levels of CTX-1 are maintained throughout the treatment period at a level that is reduced by at least 45% compared to pre-treatment or normal levels;

the polypeptide is administered in an amount from about 0.01 mg/kg to about 0.03 mg/kg every two months and the serum levels of CTX-1 are reduced by at least 45% compared to pre-treatment or normal levels, and the serum levels of CTX-1 are maintained throughout the treatment period at a level that is reduced by at least 45% compared to pre-treatment or normal levels;

the polypeptide is administered in an amount from about 0.03 mg/kg to about 0.1 mg/kg every three months and the serum levels of CTX-1 are reduced by at least 45% compared to pre-treatment or normal levels, and the serum levels of CTX-1 are maintained throughout the treatment period at a level that is reduced by at least 45% compared to pre-treatment or normal levels;

the polypeptide is administered in an amount from about 0.1 mg/kg to about 0.3 mg/kg every four months and the CTX-1 is reduced by at least 45% compared to pre-treatment or normal levels, and the serum levels of CTX-1 are maintained throughout the treatment period at a level that is reduced by at least 45% compared to pre-treatment or normal levels;

the polypeptide is administered in an amount from about 0.03 mg/kg to about 0.1 mg/kg every month and the serum levels of CTX-1 are reduced by at least 70% compared to pre-treatment or normal levels, and the serum levels of CTX-1 are maintained throughout the treatment period at a level that is reduced by at least 70% compared to pre-treatment or normal levels;

the polypeptide is administered in an amount from about 0.1 mg/kg to about 0.3 mg/kg every two months and the serum levels of CTX-1 are reduced by at least 70% compared to pre-treatment or normal levels, and the serum levels of CTX-1 are maintained throughout the treatment period at a level that is reduced by at least 70% compared to pre-treatment or normal levels;

the polypeptide is administered in an amount from about 0.1 mg/kg to about 0.3 mg/kg every three months and the serum levels of CTX-1 are reduced by at least 70% compared to pre-treatment or normal levels, and the serum levels of CTX-1 are maintained throughout the treatment period at a level that is reduced by at least 70% compared to pre-treatment or normal levels;

the polypeptide is administered in an amount from about 0.1 mg/kg to about 0.3 mg/kg every four months and the serum levels of CTX-1 are reduced by at least 70% compared to pre-treatment or normal levels, and the serum levels of CTX-1 are maintained throughout the treatment period at a level that is reduced by at least 70% compared to pre-treatment or normal levels;

the polypeptide is administered in an amount from about 0.01 mg/kg to about 0.03 mg/kg every month and the levels of NTX-1 are reduced by at least 30% compared to pre-treatment or normal levels, and the serum levels of NTX-1 are maintained throughout the treatment period at a level that is reduced by at least 30% compared to pre-treatment or normal levels;

the polypeptide is administered in an amount from about 0.03 mg/kg to about 0.1 mg/kg every two months and the levels of NTX-1 are reduced by at least 30% compared to pre-treatment or normal levels, and the serum levels of NTX-1 are maintained throughout the treatment period at a level that is reduced by at least 30% compared to pre-treatment or normal levels;

the polypeptide is administered in an amount from about 0.03 mg/kg to about 0.1 mg/kg every three months and the levels of NTX-1 are reduced by at least 30% compared to pre-treatment or normal levels, and the serum levels of NTX-1 are maintained throughout the treatment period at a level that is reduced by at least 30% compared to pre-treatment or normal levels;

the polypeptide is administered in an amount from about 0.03 mg/kg to about 0.1 mg/kg every four months and the levels of NTX-1 are reduced by at least 30% compared to pre-treatment or normal levels, and the serum levels of NTX-1 are maintained throughout the treatment period at a level that is reduced by at least 30% compared to pre-treatment or normal levels;

the polypeptide is administered in an amount from about 0.01 mg/kg to about 0.03 mg/kg every month and the levels of NTX-1 are reduced by at least 45% compared to pre-treatment or normal levels, and the serum levels of NTX-1 are maintained throughout the treatment period at a level that is reduced by at least 45% compared to pre-treatment or normal levels;

the polypeptide is administered in an amount from about 0.03 mg/kg to about 0.1 mg/kg every two months and the levels of NTX-1 are reduced by at least 45% for at least about 60 days after administration compared to pre-treatment or normal levels, and the serum levels of NTX-1 are maintained throughout the treatment period at a level that is reduced by at least 45% compared to pre-treatment or normal levels;

the polypeptide is administered in an amount from about 0.1 mg/kg to about 0.3 mg/kg every three months and the levels of NTX-1 are reduced by at least 45% for at least about 30 days to 3 months after administration compared to pre-treatment or normal levels, and the serum levels of NTX-1 are maintained throughout the treatment period at a level that is reduced by at least 45% compared to pre-treatment or normal levels;

the polypeptide is administered in an amount from about 0.1 mg/kg to about 0.3 mg/kg every four months and the levels of NTX-1 are reduced by at least 45%, compared to pre-treatment or normal levels, and the serum levels of NTX-1 are maintained throughout the treatment period at a level that is reduced by at least 45% compared to pre-treatment or normal levels;

the polypeptide is administered in an amount from about 0.1 mg/kg to about 0.3 mg/kg every month and the levels of NTX-1 are reduced by at least 70% compared to pre-treatment or normal levels, and the serum levels of NTX-1 are maintained throughout the treatment period at a level that is reduced by at least 70% compared to pre-treatment or normal levels;

the polypeptide is administered in an amount from about 0.3 mg/kg to about 1 mg/kg every two months and the levels of NTX-1 are reduced by at least 70% compared to pre-treatment or normal levels, and the serum levels of NTX-1 are maintained throughout the treatment period at a level that is reduced by at least 70% compared to pre-treatment or normal levels;

the polypeptide is administered in an amount from about 0.3 mg/kg to about 1 mg/kg every three months and the levels of NTX-1 are reduced by at least 70% compared to pre-treatment or normal levels, and the serum levels of NTX-1 are maintained throughout the treatment period at a level that is reduced by at least 70% compared to pre-treatment or normal levels; or the polypeptide is administered in an amount from about 1 mg/kg to about 3 mg/kg every four months and the levels of NTX-1 are reduced by at least 70% compared to pre-treatment or normal levels, and the serum levels of NTX-1 are maintained throughout the treatment period at a level that is reduced by at least 70% compared to pre-treatment or normal levels.

2. The method according to claim 1, wherein the polypeptide comprises or consists of SEQ ID NO: 10 or SEQ ID NO: 12.

3. The method according to claim 1, wherein the polypeptide is administered subcutaneously.

4. The method according to claim 1, wherein the postmenopausal female human subject has osteoporosis.

5. The method according to claim 2, wherein the polypeptide is administered subcutaneously.

6. The method according to claim 2, wherein the postmenopausal female human subject has osteoporosis.

7. The method according to claim 3, wherein the postmenopausal female human subject has osteoporosis.

8. The method according to claim 5, wherein the postmenopausal female human subject has osteoporosis.

* * * * *

SEQUENCE LISTING

<160> NUMBER OF SEQ ID NOS: 31

<210> SEQ ID NO 1
<211> LENGTH: 5
<212> TYPE: PRT
<213> ORGANISM: Artificial Sequence
<220> FEATURE:
<223> OTHER INFORMATION: CDR sequence

<400> SEQUENCE: 1

```
Ser Tyr Pro Met Gly
1               5

<210> SEQ ID NO 2
<211> LENGTH: 17
<212> TYPE: PRT
<213> ORGANISM: Artificial Sequence
<220> FEATURE:
<223> OTHER INFORMATION: CDR sequence

<400> SEQUENCE: 2

Ser Ile Thr Gly Ser Gly Gly Ser Thr Tyr Tyr Ala Asp Ser Val Lys
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: CDR sequence

<400> SEQUENCE: 3

Tyr Ile Arg Pro Asp Thr Tyr Leu Ser Arg Asp Tyr Arg Lys Tyr
1               5                   10                  15

<210> SEQ ID NO 4
<211> LENGTH: 126
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Arg Ser Tyr
            20                  25                  30

Pro Met Gly Trp Phe Arg Gln Ala Pro Gly Lys Glu Arg Glu Phe Val
        35                  40                  45

Ala Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Pro Glu Asp Thr Ala Val Tyr Ser Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Gln Val Thr Val Ser Ser
        115                 120                 125

<210> SEQ ID NO 5
<211> LENGTH: 126
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Arg Thr Phe Arg Ser Tyr
            20                  25                  30

Pro Met Gly Trp Phe Arg Gln Ala Pro Gly Lys Gly Arg Glu Phe Val
        35                  40                  45

Ala Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Ser Cys
                85                  90                  95

Ala Ala Tyr Ile Arg Pro Asp Thr Tyr Leu Ser Arg Asp Tyr Arg Lys
                100                 105                 110

Tyr Asp Tyr Trp Gly Gln Gly Thr Leu Val Thr Val Ser Ser
            115                 120                 125

<210> SEQ ID NO 6
<211> LENGTH: 126
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Pro Met Gly Trp Phe Arg Gln Ala Pro Gly Lys Gly Arg Glu Phe Val
        35                  40                  45

Ala Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Ser Cys
                85                  90                  95

Ala Ala Tyr Ile Arg Pro Asp Thr Tyr Leu Ser Arg Asp Tyr Arg Lys
                100                 105                 110

Tyr Asp Tyr Trp Gly Gln Gly Thr Leu Val Thr Val Ser Ser
            115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Pro Met Gly Trp Phe Arg Gln Ala Pro Gly Lys Gly Arg Glu Phe Val
        35                  40                  45

Ala Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

```
Leu Gln Met Asn Ser Leu Arg Pro Glu Asp Thr Ala Val Tyr Ser Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser
        115                 120                 125

<210> SEQ ID NO 8
<211> LENGTH: 126
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Ser Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser
        115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Arg Ser Tyr
            20                  25                  30

Pro Met Gly Trp Phe Arg Gln Ala Pro Gly Lys Gly Arg Glu Phe Val
        35                  40                  45

Ala Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser
        115                 120                 125
```

```
<210> SEQ ID NO 10
<211> LENGTH: 126
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser
        115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Gly Ser Thr Tyr Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
            100                 105                 110

Tyr Asp Tyr Trp Gly Gln Gly Thr Leu Val Thr Val Ser Ser
        115                 120                 125

<210> SEQ ID NO 12
<211> LENGTH: 385
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Pro Met Gly Trp Phe Arg Gln Ala Pro Gly Lys Gly Arg Glu Phe Val
        35                  40                  45

Ser Ser Ile Thr Gly Ser Gly Ser Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                85                  90                  95

Ala Ala Tyr Ile Arg Pro Asp Thr Tyr Leu Ser Arg Asp Tyr Arg Lys
                100                 105                 110

Tyr Asp Tyr Trp Gly Gln Gly Thr Leu Val Thr Val Ser Ser Gly Gly
            115                 120                 125

Gly Gly Ser Gly Gly Gly Ser Glu Val Gln Leu Val Glu Ser Gly Gly
    130                 135                 140

Gly Leu Val Gln Pro Gly Asn Ser Leu Arg Leu Ser Cys Ala Ala Ser
145                 150                 155                 160

Gly Phe Thr Phe Ser Ser Phe Gly Met Ser Trp Val Arg Gln Ala Pro
                165                 170                 175

Gly Lys Gly Leu Glu Trp Val Ser Ser Ile Ser Gly Ser Gly Ser Asp
            180                 185                 190

Thr Leu Tyr Ala Asp Ser Val Lys Gly Arg Phe Thr Ile Ser Arg Asp
        195                 200                 205

Asn Ala Lys Thr Thr Leu Tyr Leu Gln Met Asn Ser Leu Arg Pro Glu
    210                 215                 220

Asp Thr Ala Val Tyr Tyr Cys Thr Ile Gly Gly Ser Leu Ser Arg Ser
225                 230                 235                 240

Ser Gln Gly Thr Leu Val Thr Val Ser Ser Gly Gly Gly Gly Ser Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Thr Phe
        275                 280                 285

Ser Ser Tyr Pro Met Gly Trp Phe Arg Gln Ala Pro Gly Lys Gly Arg
    290                 295                 300

Glu Phe Val Ser Ser Ile Thr Gly Ser Gly Ser Thr Tyr Tyr Ala
305                 310                 315                 320

Asp Ser Val Lys Gly Arg Phe Thr Ile Ser Arg Asp Asn Ala Lys Asn
                325                 330                 335

Thr Leu Tyr Leu Gln Met Asn Ser Leu Arg Pro Glu Asp Thr Ala Val
            340                 345                 350

Tyr Tyr Cys Ala Ala Tyr Ile Arg Pro Asp Thr Tyr Leu Ser Arg Asp
        355                 360                 365

Tyr Arg Lys Tyr Asp Tyr Trp Gly Gln Gly Thr Leu Val Thr Val Ser
    370                 375                 380

Ser
385

<210> SEQ ID NO 13
<211> LENGTH: 115
<212> TYPE: PRT
<213> ORGANISM: Artificial Sequence
<220> FEATURE:
```

<223> OTHER INFORMATION: Nanobody sequence

<400> SEQUENCE: 13

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: Nanobody sequence

<400> SEQUENCE: 15

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
            20                  25                  30

Leu Met Gly Trp Tyr Arg Gln Gly Pro Gly Asn Glu Arg Glu Leu Val

```
            35                  40                  45
Ala Thr Cys Ile Thr Val Gly Asp Ser Thr Asn Tyr Ala Asp Ser Val
         50                  55                  60
Lys Gly Arg Phe Thr Ile Ser Met Asp Tyr Lys Gln Thr Val Tyr
 65                  70                  75                  80
Leu His Met Asn Ser Leu Arg Pro Glu Asp Thr Gly Leu Tyr Tyr Cys
                 85                  90                  95
Lys Ile Arg Arg Thr Trp His Ser Glu Leu Trp Gly Gln Gly Thr Gln
                100                 105                 110
Val Thr Val Ser Ser
        115

<210> SEQ ID NO 16
<211> LENGTH: 5
<212> TYPE: PRT
<213> ORGANISM: Artificial Sequence
<220> FEATURE:
<223> OTHER INFORMATION: Linker sequence

<400> SEQUENCE: 16

Gly Gly Gly Gly Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Linker sequence

<400> SEQUENCE: 17

Ser Gly Gly Ser Gly Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Linker sequence

<400> SEQUENCE: 18

Gly Gly Gly Gly Ser Gly Gly Gly Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Linker sequence

<400> SEQUENCE: 19

Gly Gly Gly Gly Ser Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Linker sequence

<400> SEQUENCE: 20
```

```
Gly Gly Gly Gly Ser Gly Gly Gly Gly Ser
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Linker sequence

<400> SEQUENCE: 21

Gly Gly Gly Gly Ser Gly Gly Gly Gly Ser Gly Gly Gly Gly Ser
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Linker sequence

<400> SEQUENCE: 22

Gly Gly Gly Gly Ser Gly Gly Gly Gly Ser Gly Gly Gly Gly Gly
1               5                   10                  15

Gly Ser

<210> SEQ ID NO 23
<211> LENGTH: 20
<212> TYPE: PRT
<213> ORGANISM: Artificial Sequence
<220> FEATURE:
<223> OTHER INFORMATION: Linker sequence

<400> SEQUENCE: 23

Gly Gly Gly Gly Ser Gly Gly Gly Gly Ser Gly Gly Gly Gly Ser Gly
1               5                   10                  15

Gly Gly Gly Ser
            20

<210> SEQ ID NO 24
<211> LENGTH: 25
<212> TYPE: PRT
<213> ORGANISM: Artificial Sequence
<220> FEATURE:
<223> OTHER INFORMATION: Linker sequence

<400> SEQUENCE: 24

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 25
<211> LENGTH: 30
<212> TYPE: PRT
<213> ORGANISM: Artificial Sequence
<220> FEATURE:
<223> OTHER INFORMATION: Linker sequence

<400> SEQUENCE: 25

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser
            20                  25                  30
```

<210> SEQ ID NO 26
<211> LENGTH: 35
<212> TYPE: PRT
<213> ORGANISM: Artificial Sequence
<220> FEATURE:
<223> OTHER INFORMATION: Linker sequence

<400> SEQUENCE: 26

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser
        35

<210> SEQ ID NO 27
<211> LENGTH: 15
<212> TYPE: PRT
<213> ORGANISM: Artificial Sequence
<220> FEATURE:
<223> OTHER INFORMATION: Linker sequence

<400> SEQUENCE: 27

Glu Pro Lys Ser Cys Asp Lys Thr His Thr Cys Pro Pro Cys Pro
1               5                   10                  15

<210> SEQ ID NO 28
<211> LENGTH: 24
<212> TYPE: PRT
<213> ORGANISM: Artificial Sequence
<220> FEATURE:
<223> OTHER INFORMATION: Linker sequence

<400> SEQUENCE: 28

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 29
<211> LENGTH: 12
<212> TYPE: PRT
<213> ORGANISM: Artificial Sequence
<220> FEATURE:
<223> OTHER INFORMATION: Linker sequence

<400> SEQUENCE: 29

Glu Pro Lys Thr Pro Lys Pro Gln Pro Ala Ala Ala
1               5                   10

<210> SEQ ID NO 30
<211> LENGTH: 62
<212> TYPE: PRT
<213> ORGANISM: Artificial Sequence
<220> FEATURE:
<223> OTHER INFORMATION: Linker sequence

<400> SEQUENCE: 30

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

```
Pro Lys Ser Cys Asp Thr Pro Pro Pro Cys Pro Arg Cys Pro
    50                  55                  60

<210> SEQ ID NO 31
<211> LENGTH: 3
<212> TYPE: PRT
<213> ORGANISM: Artificial Sequence
<220> FEATURE:
<223> OTHER INFORMATION: Linker sequence

<400> SEQUENCE: 31

Ala Ala Ala
1
```